US008142454B2

(12) United States Patent
Harrison et al.

(10) Patent No.: US 8,142,454 B2
(45) Date of Patent: Mar. 27, 2012

(54) APPARATUS AND METHOD FOR MAGNETIC ALTERATION OF ANATOMICAL FEATURES

(75) Inventors: Michael R. Harrison, San Francisco, CA (US); Richard J. Fechter, San Rafael, CA (US); Arthur Moran, San Bruno, CA (US); Darrell Christensen, Petaluma, CA (US)

(73) Assignee: The Regents of the University of California, San Francisco, Oakland, CA (US)

( * ) Notice: Subject to any disclaimer, the term of this patent is extended or adjusted under 35 U.S.C. 154(b) by 0 days.

(21) Appl. No.: 12/189,330

(22) Filed: Aug. 11, 2008

(65) Prior Publication Data

US 2009/0048618 A1    Feb. 19, 2009

Related U.S. Application Data

(63) Continuation-in-part of application No. 11/677,700, filed on Feb. 22, 2007, which is a continuation-in-part of application No. 11/431,416, filed on May 9, 2006, now abandoned, which is a continuation-in-part of application No. 10/954,995, filed on Sep. 29, 2004, now Pat. No. 8,043,290.

(51) Int. Cl.
 *A61B 17/08*   (2006.01)
(52) U.S. Cl. ....................................... 606/153
(58) Field of Classification Search .......... 606/112, 606/151, 153, 155, 156, 167, 171, 180; 335/285, 335/302–306; 600/36, 12; 604/22; 403/DIG. 1; 30/74; 24/308
See application file for complete search history.

(56) References Cited

U.S. PATENT DOCUMENTS

| | | | |
|---|---|---|---|
| 2,990,615 A * | 7/1961 | Ohler | 30/316 |
| 3,005,458 A | 10/1961 | Brook et al. | |
| 3,372,443 A * | 3/1968 | Daddona, Jr. | 24/303 |
| 3,512,519 A * | 5/1970 | Hall | 600/567 |
| 3,890,953 A | 6/1975 | Kraus et al. | |
| 3,939,821 A | 2/1976 | Roth | |
| 3,986,493 A | 10/1976 | Hendren, III | |
| 4,029,091 A | 6/1977 | Von Bezold et al. | |
| 4,063,561 A | 12/1977 | McKenna | |
| 4,266,533 A | 5/1981 | Ryaby et al. | |
| 4,340,038 A | 7/1982 | McKean | |
| 4,552,134 A | 11/1985 | Binard | |
| 4,596,073 A * | 6/1986 | Ewald | 30/113.1 |
| 4,896,668 A | 1/1990 | Popoff et al. | |

(Continued)

OTHER PUBLICATIONS

Obora et al., "Magnetic Ring Nonsuture Microvascular Anastomosis using Magnetic Rings", 1980, Neurol Med Chir (Tokyo) 20, pp. 497-505.*

(Continued)

*Primary Examiner* — Ryan Severson
*Assistant Examiner* — David Eastwood
(74) *Attorney, Agent, or Firm* — Lumen Patent Firm

(57) ABSTRACT

A system for auto-anastomosing a region of the body using magnetic members that may be individually delivered to different locations in the body. The magnetic members have a polar alignment that generates an attractive force to compress tissue in the region between them. The tissue in the region necroses as a result of the compressive force such that tissue surrounding the necrosed tissue heals together to form an anastomosis. A cutting member may be coupled to either the first or second magnetic member to create a temporary opening in the tissue.

8 Claims, 42 Drawing Sheets

U.S. PATENT DOCUMENTS

| | | | |
|---|---|---|---|
| 4,931,057 A * | 6/1990 | Cummings et al. | 606/153 |
| 4,932,951 A | 6/1990 | Liboff et al. | |
| 5,014,699 A | 5/1991 | Pollack et al. | |
| 5,458,558 A | 10/1995 | Liboff et al. | |
| 5,595,562 A * | 1/1997 | Grier | 600/12 |
| 5,595,563 A | 1/1997 | Moisdon | |
| 5,690,656 A * | 11/1997 | Cope et al. | 606/153 |
| 6,006,756 A | 12/1999 | Shadduck | |
| 6,024,759 A | 2/2000 | Nuss et al. | |
| 6,063,037 A * | 5/2000 | Mittermeier et al. | 600/567 |
| 6,099,542 A | 8/2000 | Cohn et al. | |
| 6,113,620 A * | 9/2000 | Chung | 606/189 |
| 6,190,353 B1 * | 2/2001 | Makower et al. | 604/95.01 |
| 6,292,680 B1 | 9/2001 | Somigyi et al. | |
| 6,306,075 B1 | 10/2001 | Shadduck | |
| 6,352,543 B1 | 3/2002 | Cole | |
| 6,387,096 B1 | 5/2002 | Hyde, Jr. | |
| 6,569,166 B2 | 5/2003 | Gonzalez | |
| 6,652,540 B1 | 11/2003 | Cole et al. | |
| 6,656,194 B1 | 12/2003 | Gannoe et al. | |
| 6,669,709 B1 | 12/2003 | Cohn et al. | |
| 6,719,768 B1 | 4/2004 | Cole et al. | |
| 6,802,847 B1 | 10/2004 | Carson et al. | |
| 7,001,402 B2 | 2/2006 | Yencho | |
| 7,135,022 B2 | 11/2006 | Kosashvili et al. | |
| 7,374,567 B2 * | 5/2008 | Heuser | 606/185 |
| 2002/0072758 A1 * | 6/2002 | Reo et al. | 606/153 |
| 2002/0103495 A1 | 8/2002 | Cole | |
| 2003/0078610 A1 * | 4/2003 | Yedlowski | 606/179 |
| 2003/0144682 A1 | 7/2003 | Qureshi et al. | |
| 2004/0030395 A1 | 2/2004 | Blunn et al. | |
| 2004/0078038 A1 * | 4/2004 | Desinger et al. | 606/50 |
| 2004/0078039 A1 * | 4/2004 | Michelson | 606/61 |
| 2004/0116945 A1 | 6/2004 | Sharkawy et al. | |
| 2004/0122334 A1 | 6/2004 | Yamashiro | |
| 2004/0215214 A1 | 10/2004 | Crews et al. | |
| 2005/0021059 A1 | 1/2005 | Cole et al. | |
| 2005/0080439 A1 | 4/2005 | Carson et al. | |
| 2005/0228412 A1 | 10/2005 | Surti | |
| 2006/0036267 A1 | 2/2006 | Saadat et al. | |
| 2006/0282106 A1 | 12/2006 | Cole et al. | |
| 2007/0010834 A1 | 1/2007 | Sharkawy et al. | |
| 2007/0156055 A1 | 7/2007 | Royalty | |
| 2007/0250162 A1 | 10/2007 | Royalty | |
| 2008/0114384 A1 * | 5/2008 | Chang et al. | 606/153 |

OTHER PUBLICATIONS

M.R. Harrison et al. "Magnetic Mini-Mover Procedure for Pectus Excavatum: I. DEvelopment, design, and simulations for feasibility and safety", J. Pediatr. Surg. vol. 42, No. 1, pp. 81-85 (2007), discussion pp. 85-86.

T. Pittman et al. Cranial Vault Moulding by the Transcutaneous Activation of Implanted Magnets: Pediatric Neurosurg. 1997, vol. 27, pp. 78-83.

A. Leonard. "Surgical Corrective Procedure for Pectus Excavatum and Pectus Carinatum", http://pectusdeformity.com, downloaded from internet May 8, 2004, pp. 1-5.

* cited by examiner

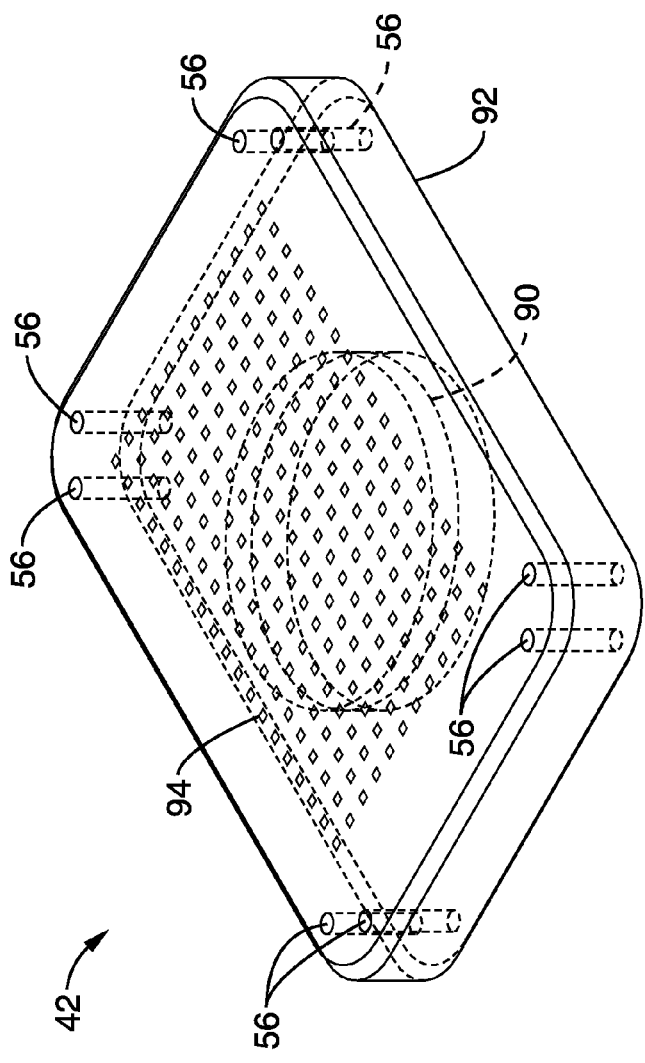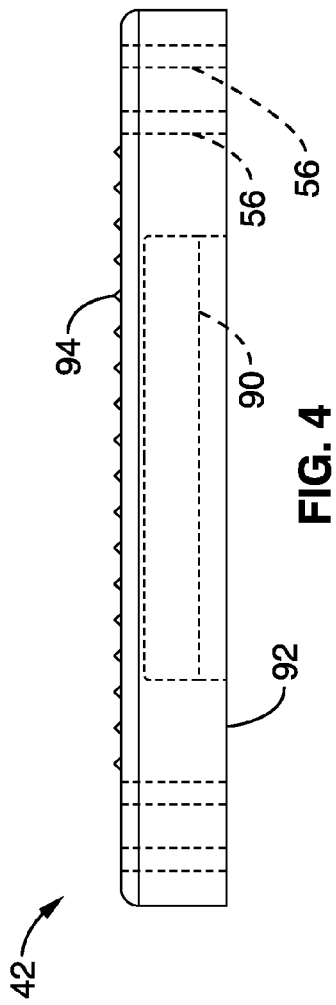

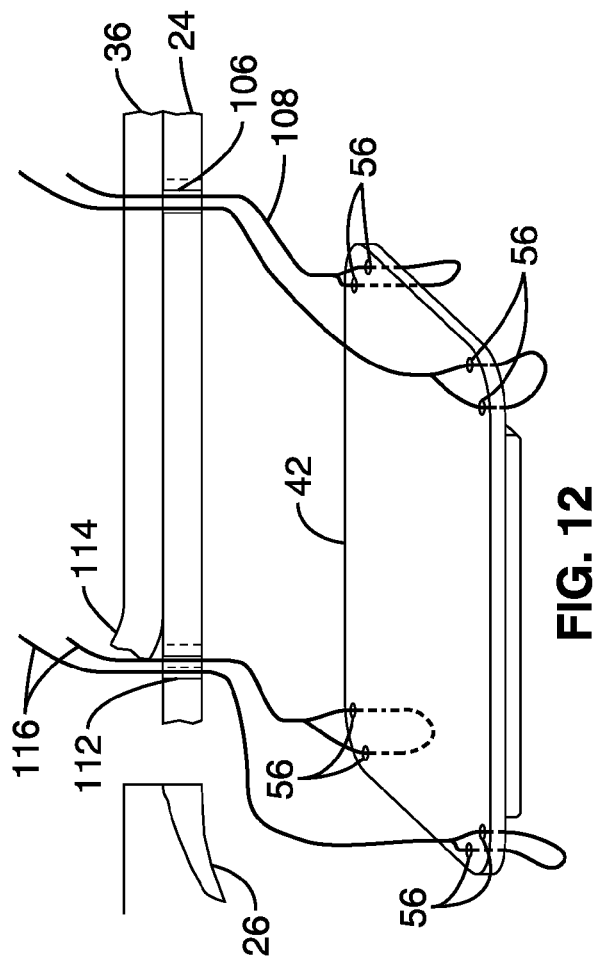
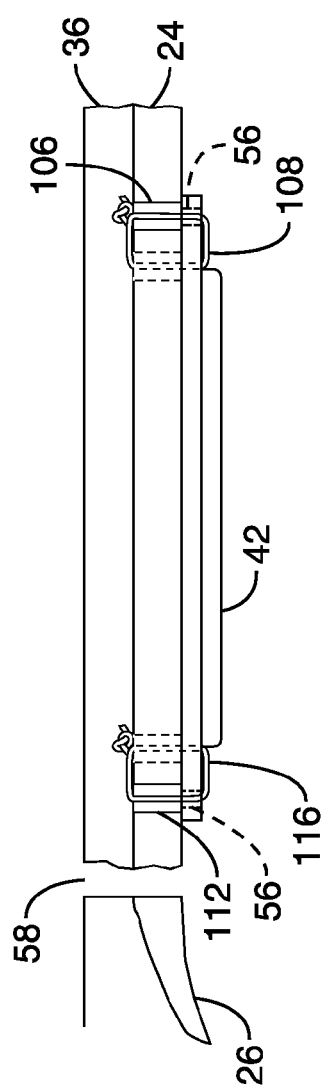

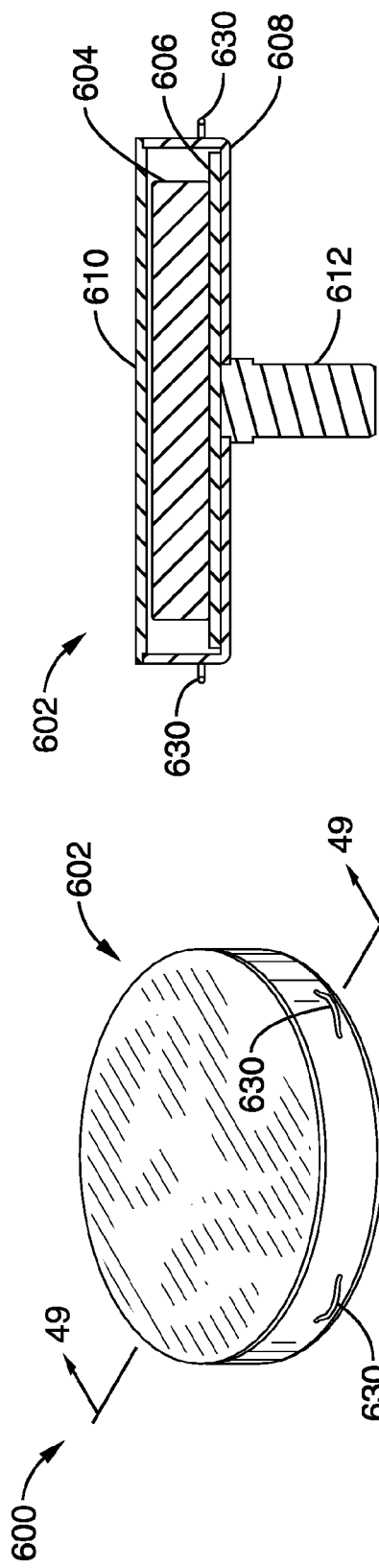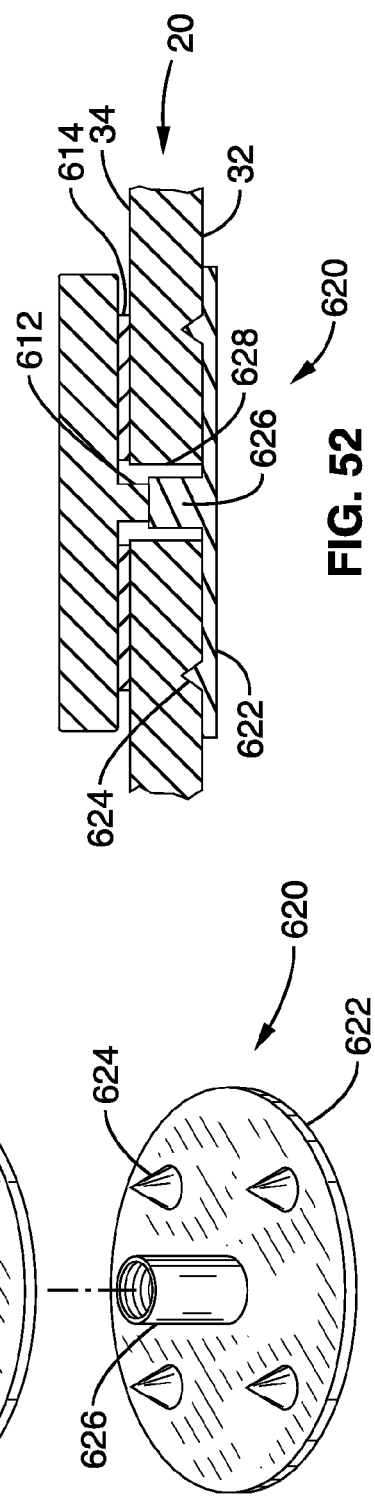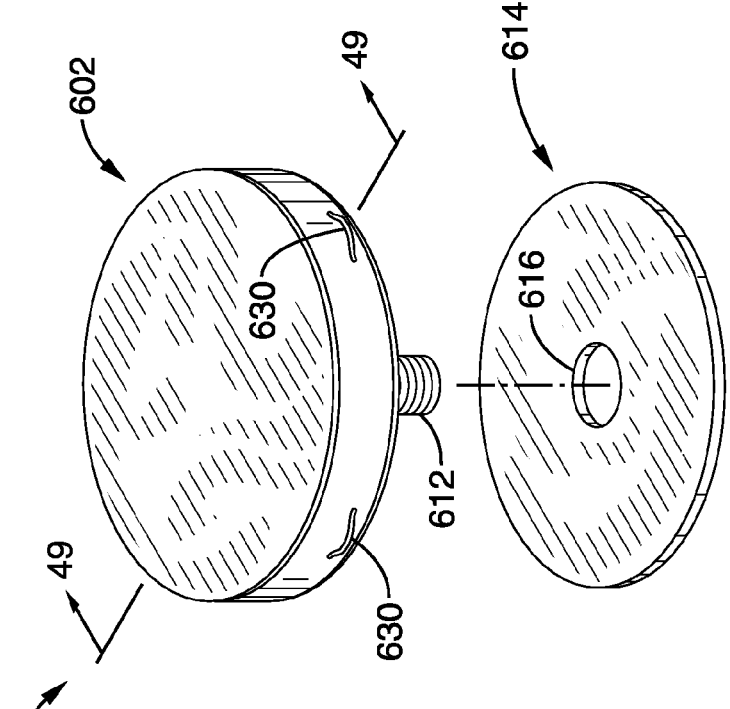

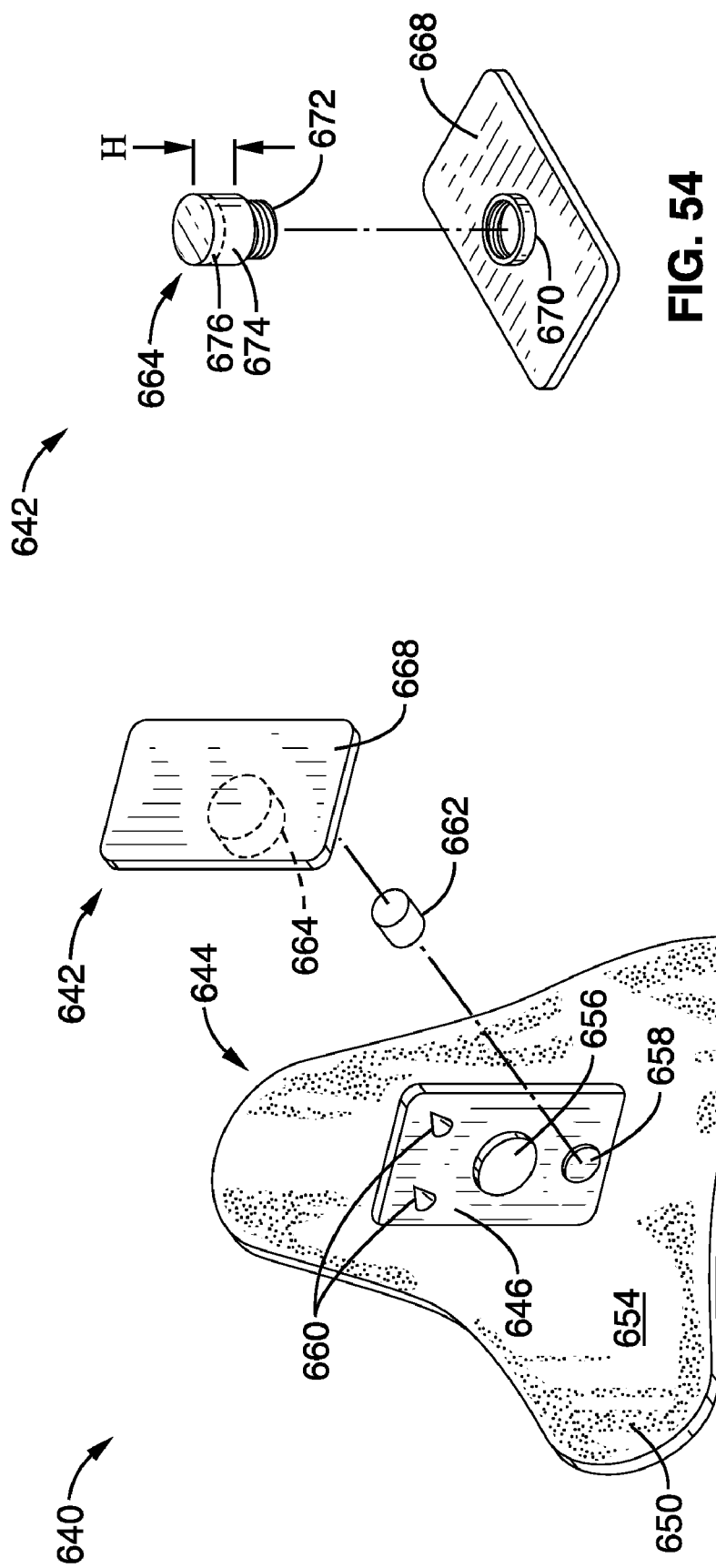

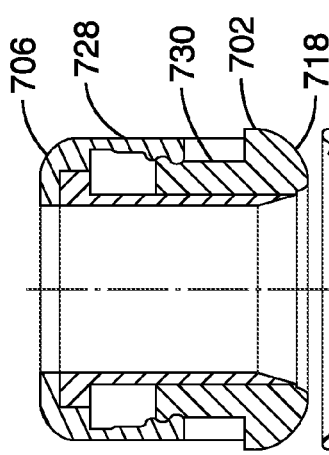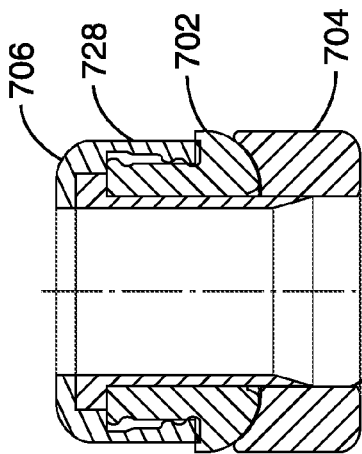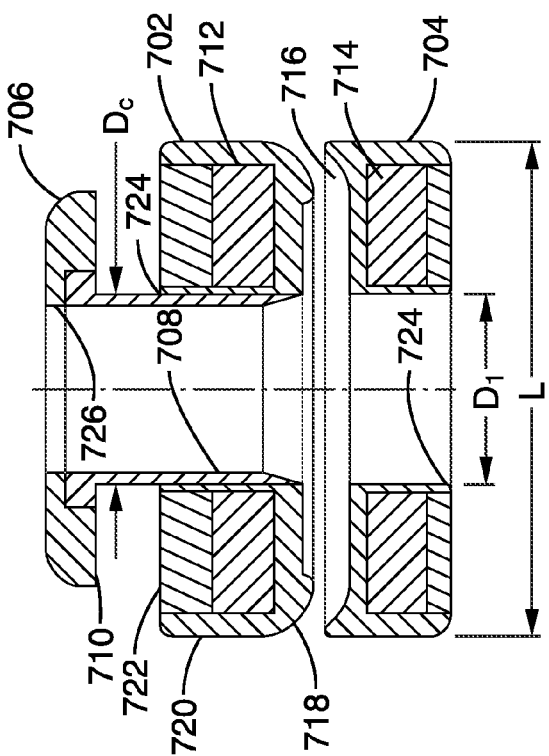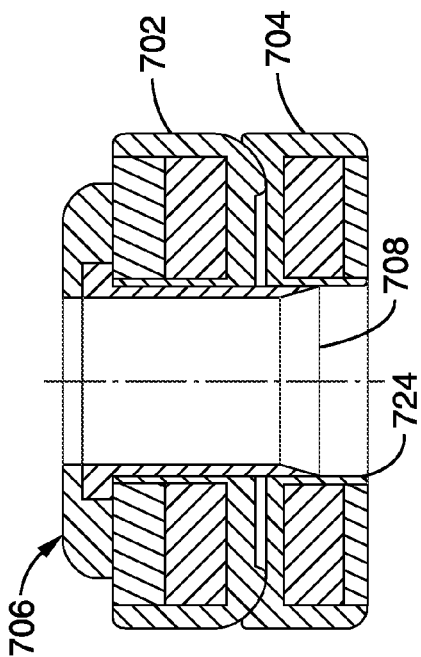

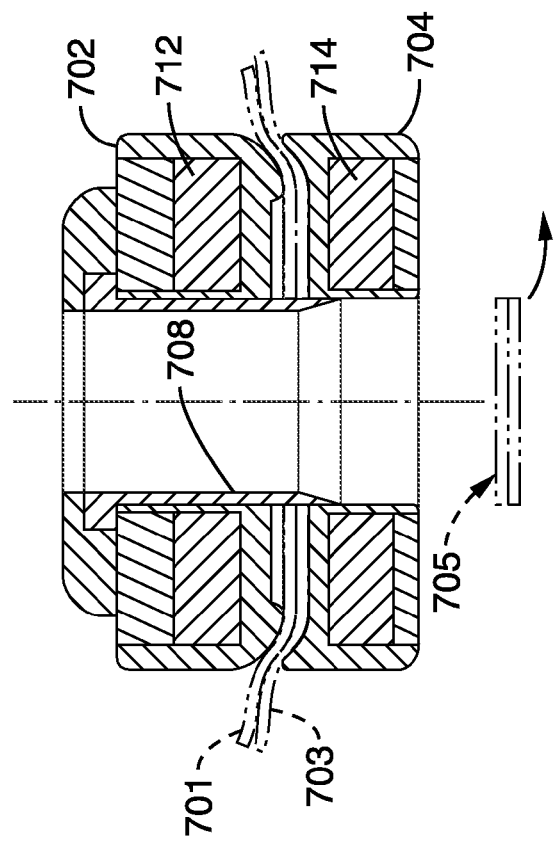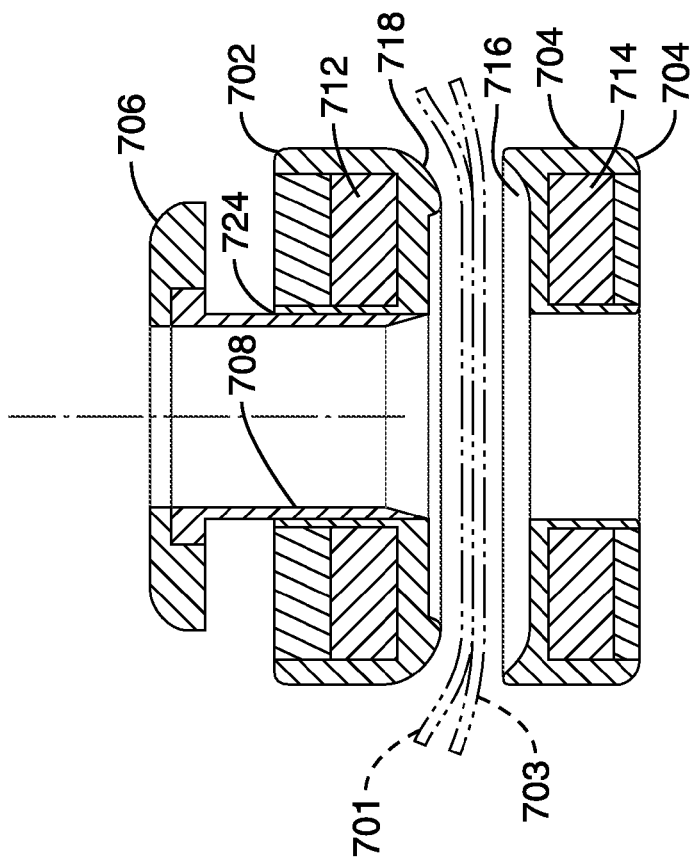

APPARATUS AND METHOD FOR MAGNETIC ALTERATION OF ANATOMICAL FEATURES

CROSS-REFERENCE TO RELATED APPLICATIONS

This application is a continuation-in-part of copending application Ser. No. 11/677,700, filed on Feb. 22, 2007, incorporated herein by reference in its entirety, which is a continuation-in-part of copending application Ser. No. 11/431,416, filed on May 9, 2006, incorporated herein by reference in its entirety, which is a continuation-in-part of copending application Ser. No. 10/954,995, filed on Sep. 29, 2004, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to apparatus and methods for magnetically manipulating body structures and more particularly to performing corrective procedures on a patient via incremental magnetic loading.

2. Description of Related Art

Anatomical deformities occur in the general populous in a number of different forms and from a variety of causes. Examples of skeletal deformities include pectus excavatum, scoliosis, club feet, and numerous forms of skeletal dysplasia. These conditions are treated in a variety of different manners from braces to surgery, with sometimes minimal efficacy.

The defect known as pectus excavatum, or funnel chest, is a congenital anomaly of the anterior chest wall. The excavatum defect is characterized by a deep depression of the sternum, usually involving the lower half or two thirds of the sternum, with the most recessed or deepest area at the junction of the chest and the abdomen. The lower 4-6 costal or rib cartilages dip backward abnormally to increase the deformity or depression and push the sternum posterior or backward toward the spine. Also, in many of these deformities, the sternum is asymmetric or it courses to the right or left in this depression. In many instances, the depression is on the right side.

Pectus excavatum with significant deformity occurs in approximately 1 out of every 2000 births. The deformity may be present at birth but is often noted after several years of age and usually worsens during rapid growth around puberty. Because of the pressure of the sternum and cartilages, defect also pushes the midline structures so that the lungs are compressed from side to side and the heart (right ventricle) is compressed. Severe lesions have a major effect on thoracic volume and pulmonary function but the principal motivation for repair is the deformity itself. It does occur in families and thus, is inherited in many instances. Other problems, especially in the muscle and skeletal system, also may accompany this defect. In approximately ⅕ of the patients, scoliosis is present. The regression or any improvement in this defect rarely occurs because of the fixation of the cartilages and the ligaments. When one takes a deep breath or inspires, the defect is usually accentuated.

Pectus excavatum can be repaired surgically using an open approach in which the malformed costal cartilages are resected and the sternum forcibly held in place with a metal strut. In another approach, described in U.S. Pat. No. 6,024,759, the sternum is forced into a corrected position often under great tension, and held in place with a metal strut. Both can achieve good results but at the cost of considerable morbidity: an operation under general anesthesia followed by a 4-7 day hospital stay required for pain control usually by continuous epidural analgesia. Several more weeks of moderate to severe discomfort are typical and complications from the sternum held forcibly against the metal strut are not infrequent. It is necessary to leave the bar in place for a year or more before it is removed in another procedure. Total cost usually reimbursed by third party payers averages more than $30,000.

The problem with all currently available pectus excavatum surgical repairs is that they attempt to achieve immediate total correction and fixation often under considerable tension. A better approach would be the gradual step-by-step correction of the deformity by applying a smaller force over a longer period of time.

Another skeletal deformity, scoliosis, is a condition in which an individual has an abnormal spine curvature. Generally, some curvature in the neck, upper trunk and lower trunk is normal. However, when there are abnormal side-to-side (lateral) curves in the spinal column, the patient is generally diagnosed as having as scoliosis.

Orthopedic braces are typically used to prevent further spinal deformity in children with curve magnitudes within the range of 25 to 40 degrees. If these children already have curvatures of these magnitudes and still have a substantial amount of skeletal growth left, then bracing is a viable option. The intent of bracing, however, is to prevent further deformity, and is generally not used to correct the existing curvature or to make the curve disappear.

Surgery is an option used primarily for severe scoliosis (curves greater than 45 degrees) or for curves that do not respond to bracing. The two primary goals for surgery are to stop a curve from progressing during adult life and to diminish spinal deformity.

Although there are different techniques and methods used today for scoliosis surgery, all of them involve fairly invasive procedures with considerable patient morbidity. One frequently performed surgery involves posterior spinal fusion with instrumentation and bone grafting, which is performed through the patient's back. During this surgery, the surgeon attaches a metal rod to each side of the patient's spine by anchors attached to the vertebral bodies. The spine is then fused with a bone graft. The operation usually takes several hours and the patient is typically hospitalized for a week or more. Most patients are not able to return to school or for several weeks after the surgery and cannot perform some pre-operative activities for up to four to six months.

Another surgery option for scoliosis is an anterior approach, wherein the surgery is conducted through the chest walls instead of entering through the patient's back. During this procedure, the surgeon makes incisions in the patient's side, deflates the lung and removes a rib in order to reach the spine. The anterior spinal approach generally has quicker patient rehabilitation, but usually requires bracing for several months after this surgery.

Yet another medical practice in need of improvement is anastomosis of organs, i.e. creating an opening between two normally separate anatomical regions or organs. Anastomosing hollow organs together is a mainstay of surgery: vascular anastomosis, intestinal anastomosis, urinary tract anastomosis are common procedures in the medical practice. Restoring continuity to hollow viscera has been a fertile realm for surgeons, and numerous techniques have evolved in attempt to make these connections work. The most commonly used are suture anastomosis or stapled anastomosis. However, these techniques tend to be highly invasive and result in significant morbidity.

For these reasons, it would be desirable to provide improved apparatus and methods for repositioning bone structures, by applying a corrective force to the bone structure, which could be gradually adjusted much like orthodontic tooth braces.

It would be further desirable to provide a device that applies a corrective force to reposition a body member without a mechanical force that requires piercing of the skin, thereby limiting the specter of infection and wound problems.

In addition, it would be desirable to provide a device for repositioning bones structures having tension-sensing technology to allow measurement of the force applied to correct all types of asymmetric deformities and allow protection of skin against pressure damage.

It would further be desirable to provide improved devices and methods for minimally invasively treating pectus excavatum.

In addition, it would be desirable to provide improved devices and methods for minimally invasively treating scoliosis.

At least some of these objectives will be met with the inventions described hereinafter.

BRIEF SUMMARY OF THE INVENTION

The present invention comprises apparatus and methods for altering the position, orientation, growth or development of body parts and organs by magnetic forces to apply a steady sustained force over time. The invention uses magnetic force fields that may be used to correct a number of anatomic deformities, including, but not limited to: pectum excavetum, pectus carinatum, scoliosis, club feet, cranial/facial anomalies or defects, skeletal dysplasias, cartilaginous deformities/dysphasia, joint deformities/dysphasia, and generating an anastomosis or stoma to a visceral wall. The invention may also be used to incrementally lengthen bone or apply bone compression to promote healing.

One aspect is a system for auto-anastomosing a region of the body. The system includes a first magnetic member configured to be delivered to a location in the body adjacent the region, and a second magnetic member configured to be located adjacent the region opposite from the first magnetic member such that the region is disposed in between the first magnetic member and the second magnetic member. The first and second magnetic members have first and second bores running through the length of the members, e.g. axially down cylindrical or elliptical members. The first and second magnetic members have a polar alignment that generates an attractive force to compress tissue in the region between them. A cutting member may be coupled to either the first or second magnetic member. The cutting member may be disposed in the first bore or second bore, and is configured to cut the tissue to create a temporary opening in the tissue. The tissue in the region necroses as a result of the compressive force such that tissue surrounding the necrosed tissue heals together to form an anastomosis.

In a preferred embodiment, the region comprises tissue occupied by first and second viscera segments in the body. The first magnetic member is shaped and sized to be delivered into the first viscera segment, and the second magnetic member is configured to be delivered to the second viscera segment at a location in proximity to the first magnet to generate the compressive force in the tissue between first and second viscera segments. The first and second bores are located to line up substantially concentric when the first and second magnetic members are positioned at the region, wherein the cutting member reciprocates in the first bore to cut said tissue, thereby generating a temporary opening in the tissue for fluid communication between the first and second viscera segments.

The viscera may be any hollow organ or lumen where anastomosis is desired. In a preferred embodiment, the method is performed on an organ or lumen, or plurality of organs or lumens, in the gastrointestinal or urinary tracts, such as the small intestines, stomach, colon, ureters, renal pelvis, bladder, urethra, etc.

In a preferred embodiment, the first and second magnetic members and cutter member are configured to pass as a unit along with the necrosed tissue through one of the first or second viscera segments and out the body.

Generally, the first and second magnetic members comprise magnets housed in biocompatible casings.

In another embodiment, the first and second magnetic members comprise first and second mating surfaces that compress the tissue to generate a non-uniform compressive force distribution across the tissue. For example, the first and second mating surfaces may be structured such that the compressive force increases radially inward from the periphery of the surfaces. The first and second mating surfaces may comprise at least one curvilinear surface.

In one mode, the first mating surface comprises a planar surface and the second mating surface comprises a curvilinear surface. In another mode, the first mating surface comprises a concave curvilinear surface having a first radius and the second magnetic member comprises a convex curvilinear surface having a second radius. The first may be larger than the second radius such that a non-uniform compressive force is distributed across the region of compressed tissue. The concave spherical surface and the convex spherical surface may be configured such the compressive force increases radially inward from the periphery of the surfaces. The compressive force may necrose tissue radially inward with respect to the surfaces, wherein the compressive force at the periphery is configured to promote growth and fuse the tissue at the periphery.

In a preferred embodiment, the cutting member comprises a blade shaped to slideably mate with the first bore so that the cutting member slides along the bore to cut the tissue located between the first and second magnets. The cutting member may have a through-hole to allow fluid communication through the first and second magnetic members and between the first viscera segment and the second viscera segment.

The blade may terminate at a tab to limit motion of the blade within the bore, wherein the tab also retains the blade within the bores of the first and second magnetic members. The magnetic force of the magnets may also hold the blade in place.

In one embodiment, the first and second magnetic members have an oblong shape to promote transport within the first and second viscera.

Another aspect is a method for auto-anastomosing a region of the body. The method includes the steps of delivering a first magnetic member to a first location in the body adjacent the region, locating a second magnetic member adjacent the region opposite from the first magnetic member such that the region is disposed in between the first magnetic member and the second magnetic member, generating an attractive force between the first magnetic member and the second magnetic member to compress tissue in the region between the first magnetic member and the second magnetic member, and cutting the tissue to generate a temporary opening at the region. The temporary opening provides fluid communication between the first magnetic member and the second magnetic member while necrosing the tissue in the region around said opening occurs as a result of the compressive force. Finally, the tissue surrounding the necrosed tissue heals together to form an anastomosis.

In one embodiment of the current aspect, the region comprises tissue occupied by first and second viscera segments in the body. The first magnetic member is delivered into the first viscera segment, and the second magnetic member is delivered to the second viscera segment at a location in proximity to the first magnet to generate a compressive force in the tissue in between first and second viscera segments; The first and second magnetic members comprise first and second bores;

The tissue may be cut by reciprocating the first magnetic member in the first bore to cut the tissue, thereby generating the temporary opening in the tissue. The first bore is in fluid communication with the second bore to allow fluid communication between the first and second viscera segments through the temporary opening. Preferably, the first and second magnetic members line up substantially concentric when positioned at the region, so that tissue is cut by sliding a blade along the first bore and into the tissue. The blade may have a through-hole to allow fluid communication through the first and second magnetic members and between the first viscera segment and the second viscera segment.

Another aspect is an apparatus for auto-anastomosing a region of the body comprising first and second adjacent visceral walls. The apparatus includes a first magnetic member configured to be delivered to a first location at the first visceral wall and adjacent the region, and a second magnetic member configured to be positioned at a second location along the second visceral wall opposite from the first magnetic member such that the region of the first and second visceral walls is disposed in between the first magnetic member and the second magnetic member. The first and second magnetic members have bores there though that line up with respect to each other when the first and second members are positioned at the region and a cutting member slideably disposed in the bore of the first magnetic member. The cutting member has a blade configured to cut the tissue to create a temporary opening in the tissue of the first and second visceral walls. The first and second magnetic members, when positioned at the region, generate an attractive force to compress the tissue of the visceral walls surrounding the temporary opening, wherein the compressive force fuses the visceral walls to form a fistula between the first and second visceral walls.

In one embodiment, the first and second magnetic members comprise first and second mating surfaces having at least one curvilinear surface.

Preferably, the blade has a through-hole to allow fluid communication through the first and second magnetic members and between the first and second visceral walls.

Another aspect is a system for auto-anastomosing a region of the body having first and second adjacent visceral walls. The system includes a first magnetic member configured to be delivered to a first location at the first visceral wall and adjacent the region, and a second magnetic member configured to be positioned at a second location along the second visceral wall opposite from the first magnetic member such that the region of the first and second visceral walls is disposed in between the first magnetic member and the second magnetic member. The first and second magnetic members comprise first and second mating surfaces having at least one curvilinear surface. The first and second magnetic members, when positioned at the region, generate an attractive force to compress the tissue of the visceral walls, wherein the compressive force fuses the visceral walls to form a fistula between the first and second visceral walls.

The mating surfaces, e.g. the surfaces that contact the tissue to generate the compressive force, may be structured to generate a non-uniform compressive force across the region of compressed tissue.

The first and second magnetic members may have bores there though that line up with respect to each other, e.g. concentrically, when the first and second members are positioned at the region. The bores allow access to the tissue to cut a temporary opening in the tissue of the first and second visceral walls. A cutting member may be slideably disposed in the bore of one of the magnetic members, wherein the cutting member has a blade configured to cut temporary opening.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only, and where like reference numbers denote like elements:

FIG. 3 shows an embodiment of the implant of the present invention.

FIG. 4 is a side view of the implant of FIG. 3.

Figure 5:
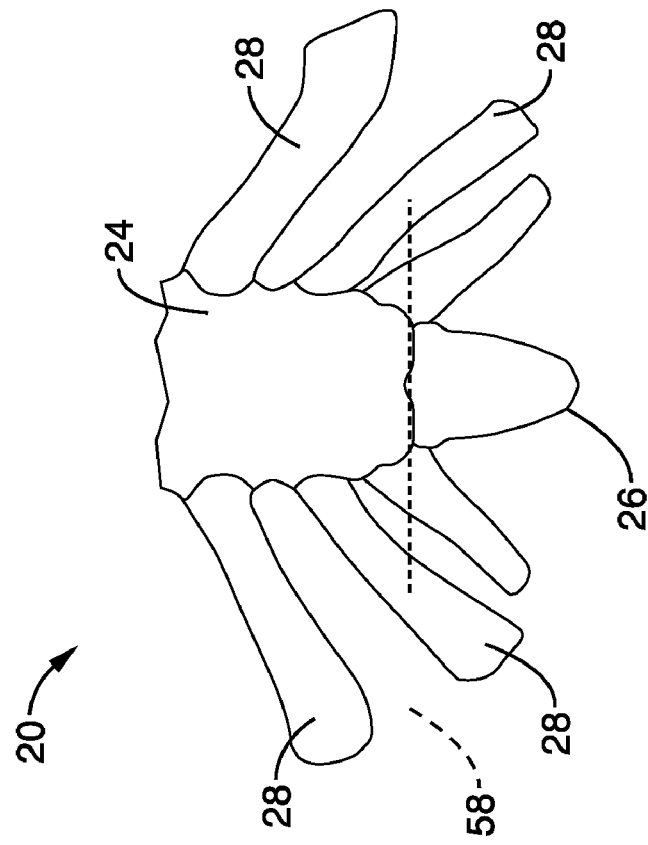

FIG. 5. is a schematic view of a sternum.

Figure 6:
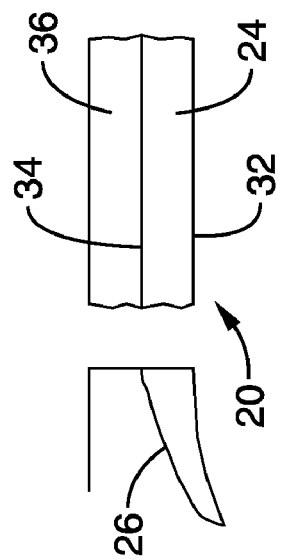

FIG. 6. is a cross-sectional view of a sternum with the xiphoid separated from the sternum body.

Figure 7:
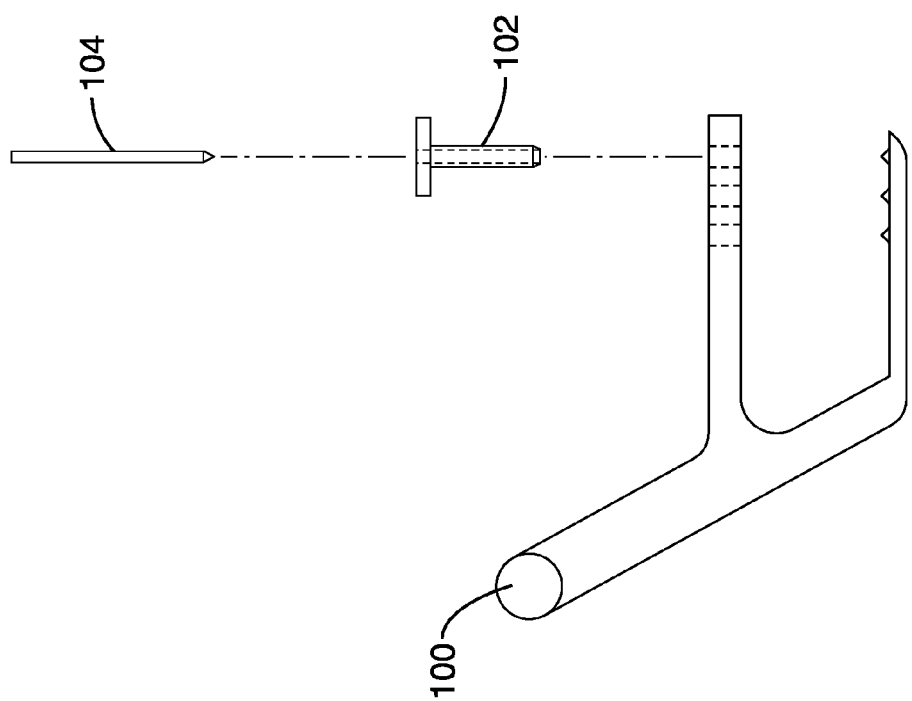

FIG. 7 is an implant drill guide according to the present invention.

Figure 8:
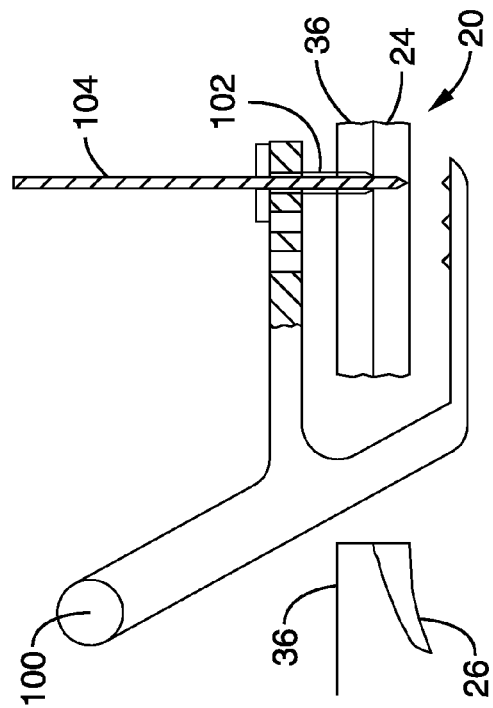

FIG. 8 shows the drill guide of FIG. 7 installed over the sternum.

Figure 9:
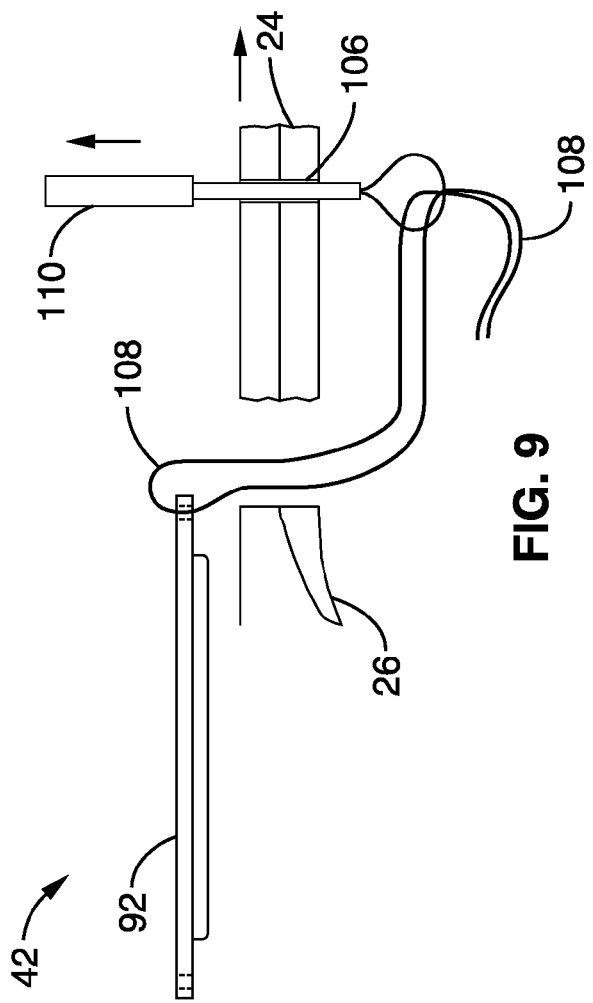

FIG. 9 illustrates a preferred method for installing a portion of the implant to the posterior surface of the sternum.

Figure 10:
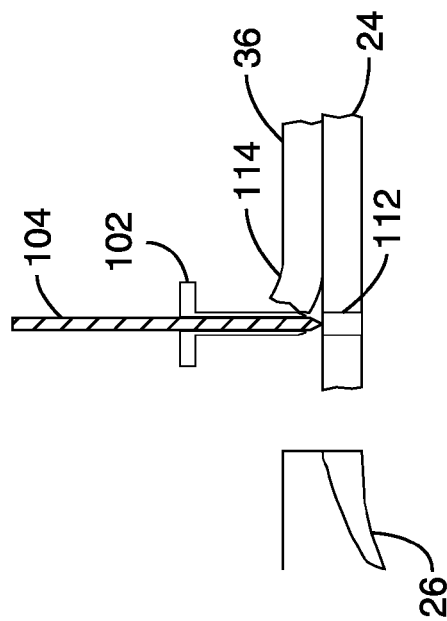

FIG. 10 illustrates a portion of the drill guide of FIG. 7 positioned over a second location on the sternum.

Figure 11:
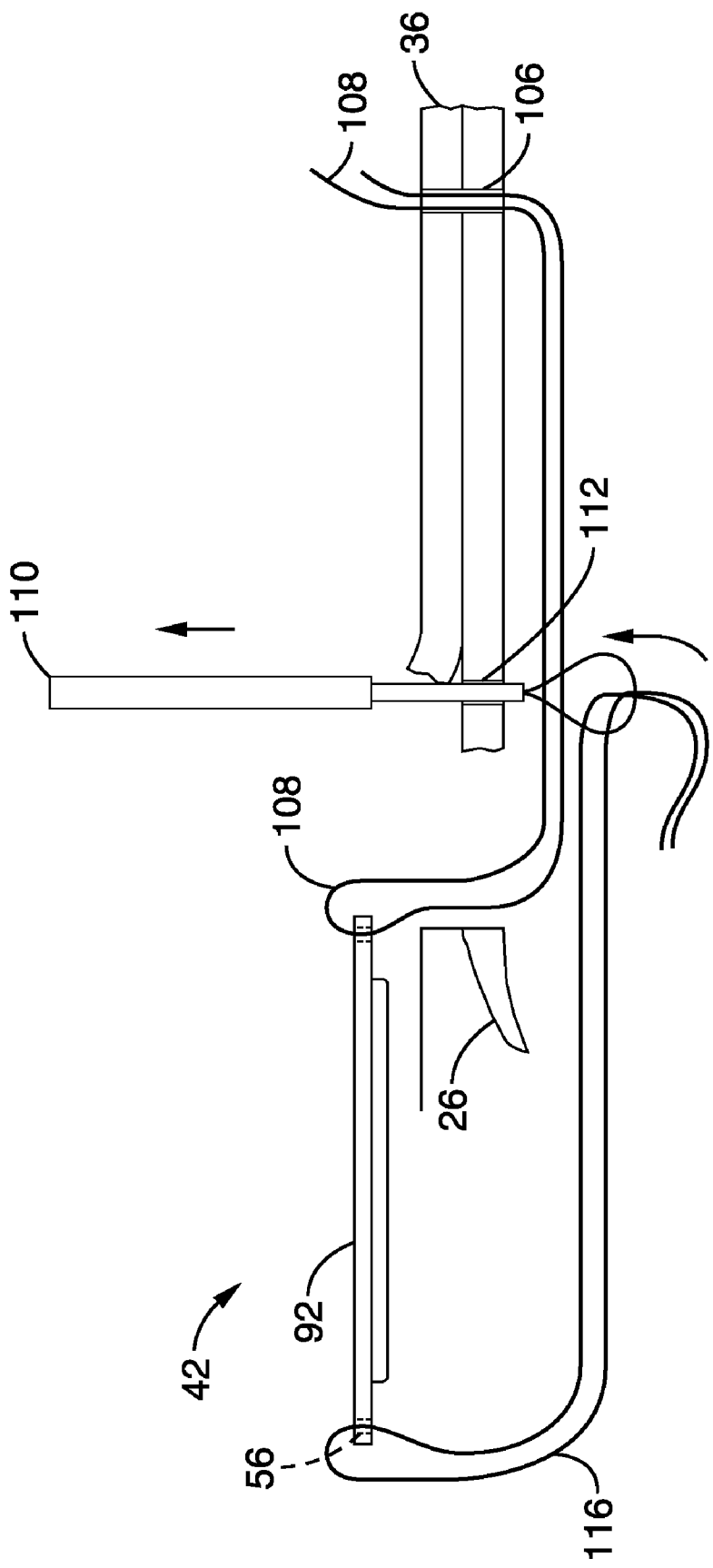

FIG. 11 illustrates a preferred method for installing a second portion of the implant to the posterior surface of the sternum.

FIG. 12 is another view of the method of FIG. 11.

FIG. 13 shows the implant according to the present invention installed on the posterior surface of the sternum.

Figure 14:
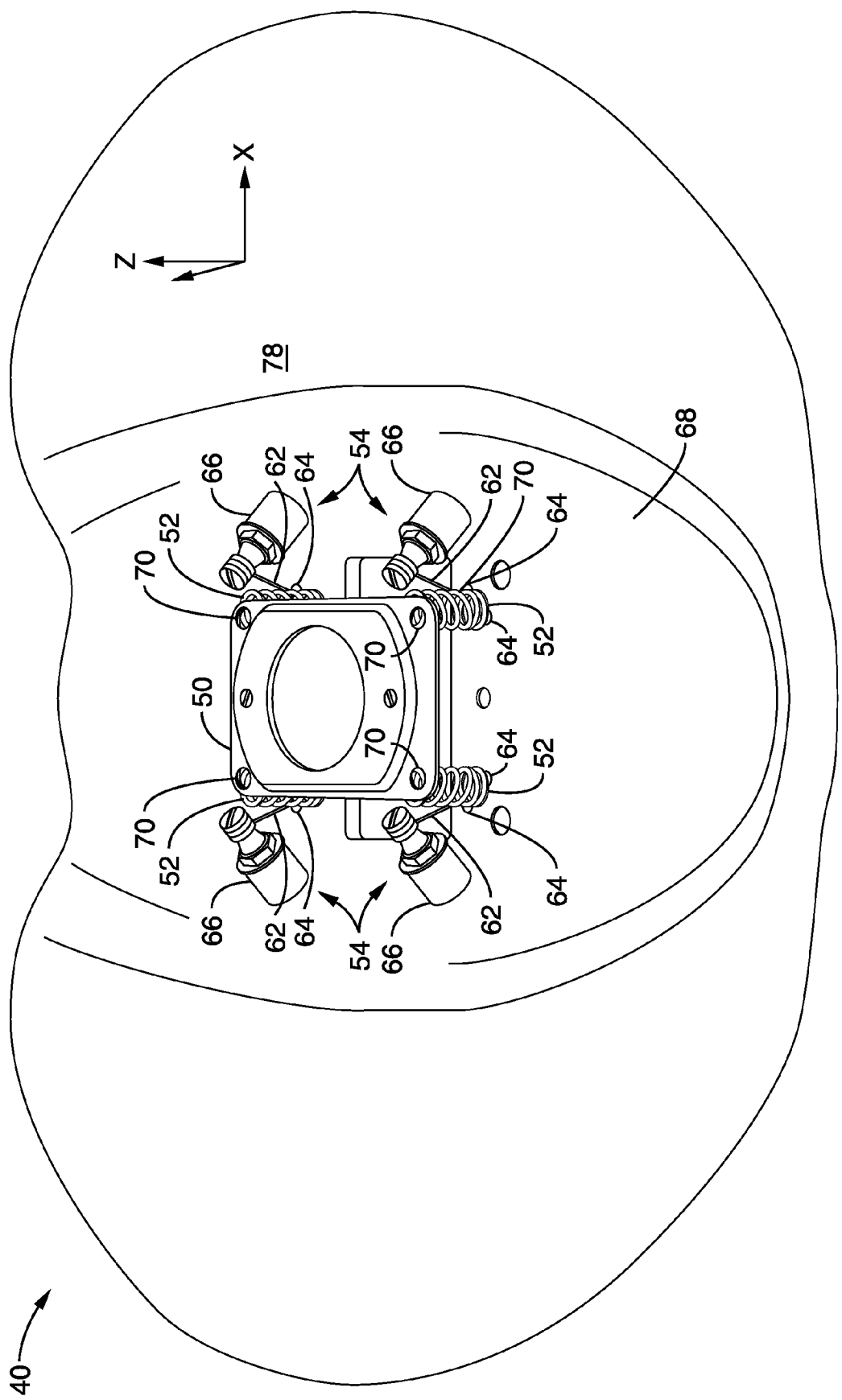

FIG. 14 is a view of the underside of an embodiment of the platform according to the present invention.

Figure 15:
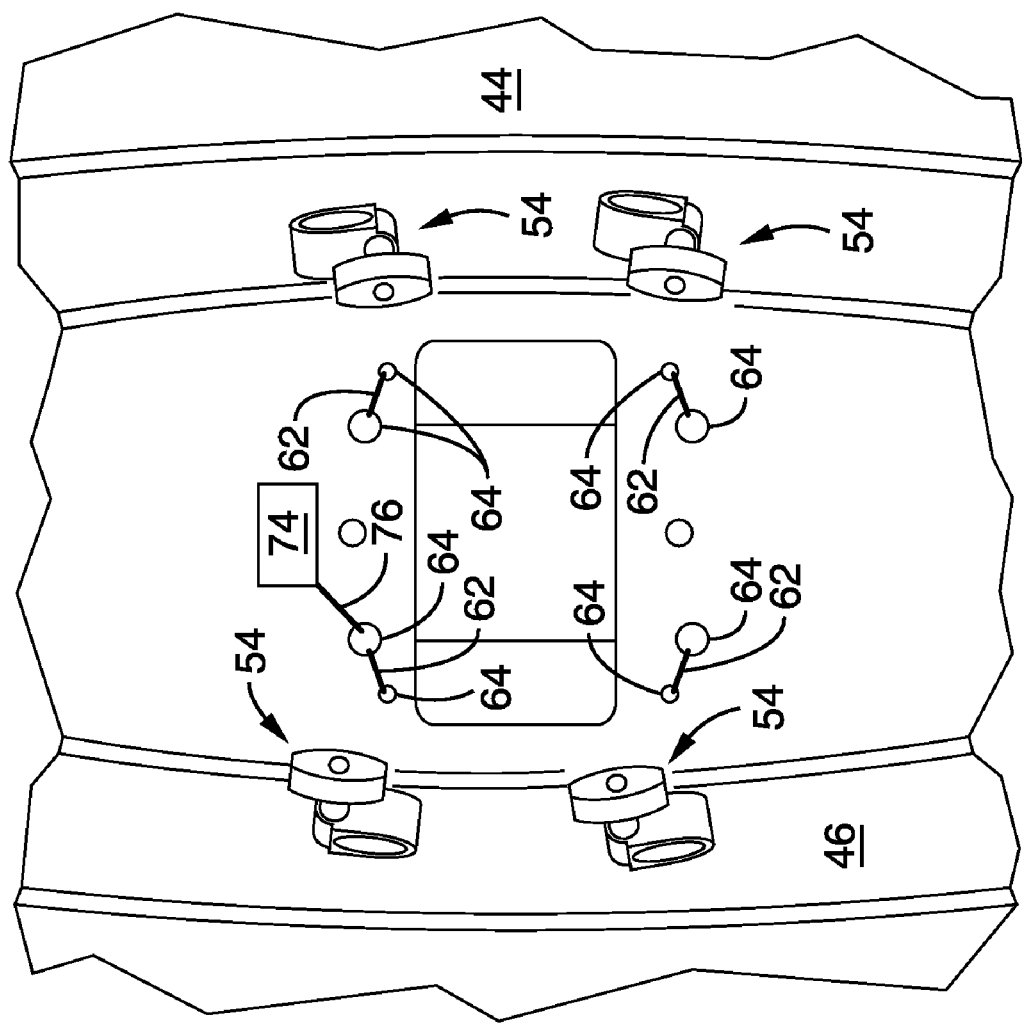

FIG. 15 is a view of the top of the platform of FIG. 14.

Figure 16:
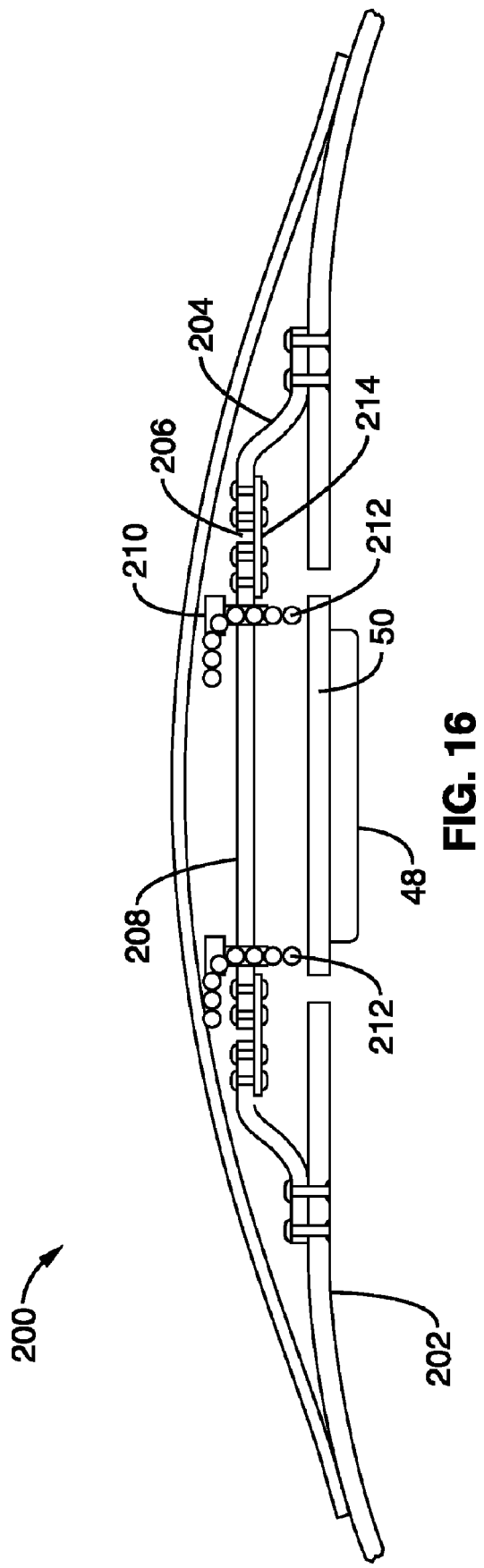

FIG. 16 is a side view of another embodiment of the platform of the present invention.

Figure 17:
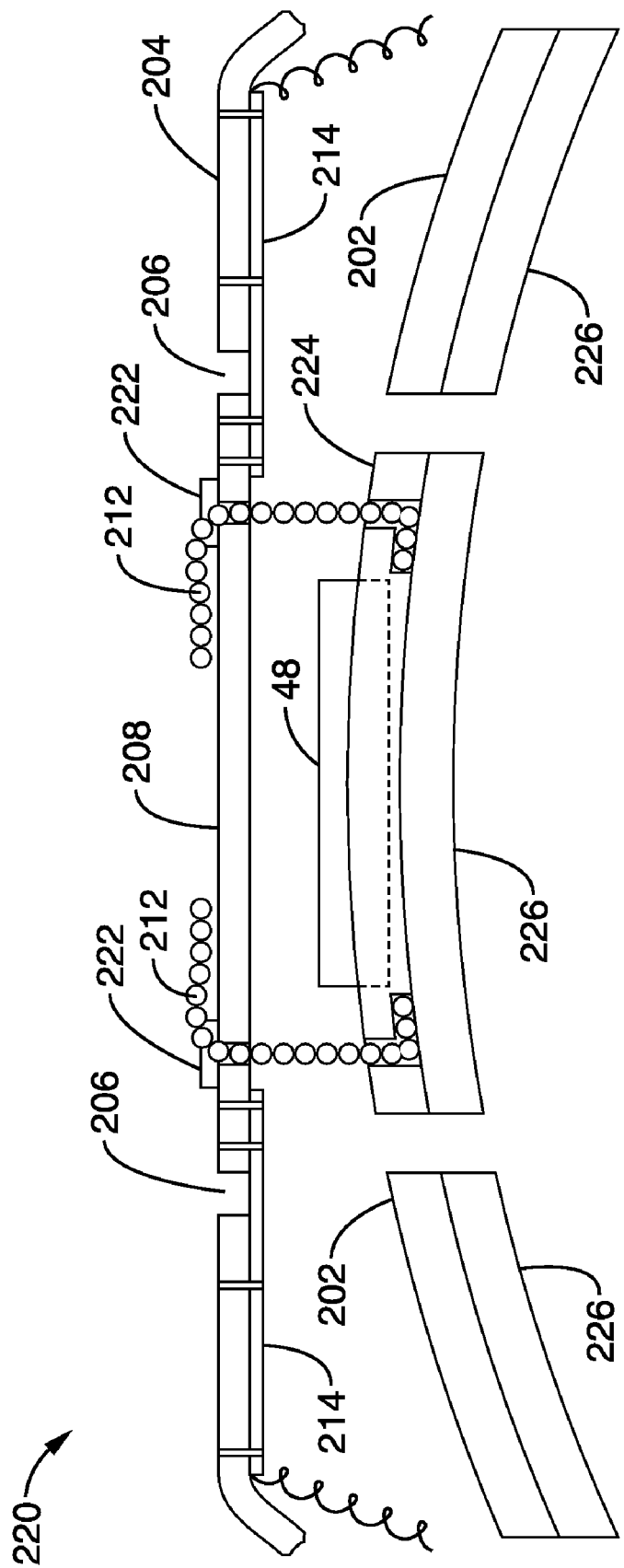

FIG. 17 is a side of another embodiment of the platform of the present invention.

Figure 18B:
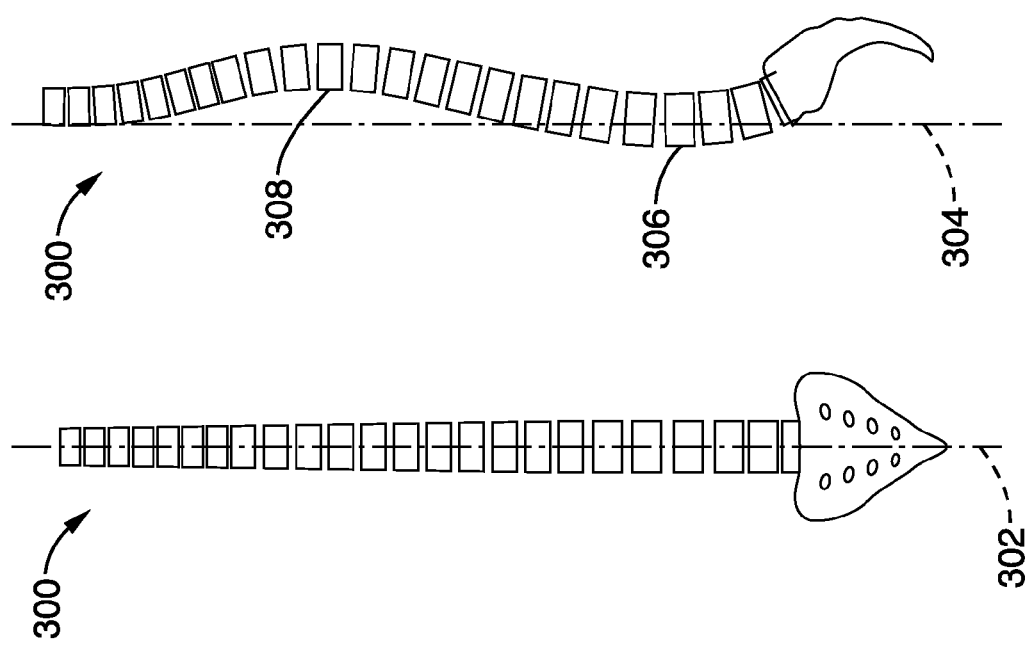
Figure 18A:
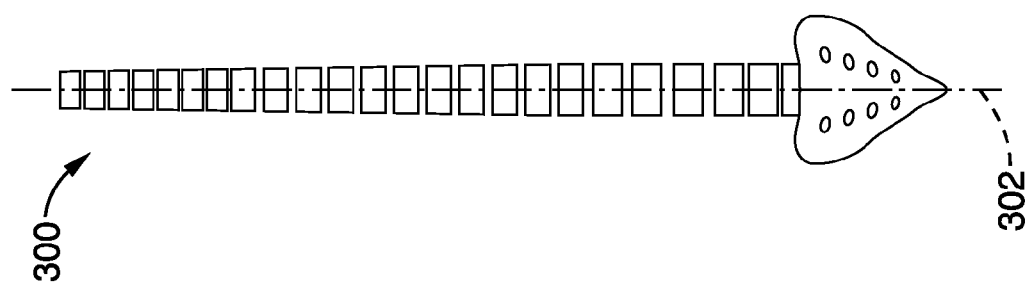

FIG. 18A is an anterior view of the human spine.

FIG. 18B is a lateral view of the human spine.

FIGS. 19A-D illustrate various abnormal curvatures of the spine due to scoliosis.

Figure 20:
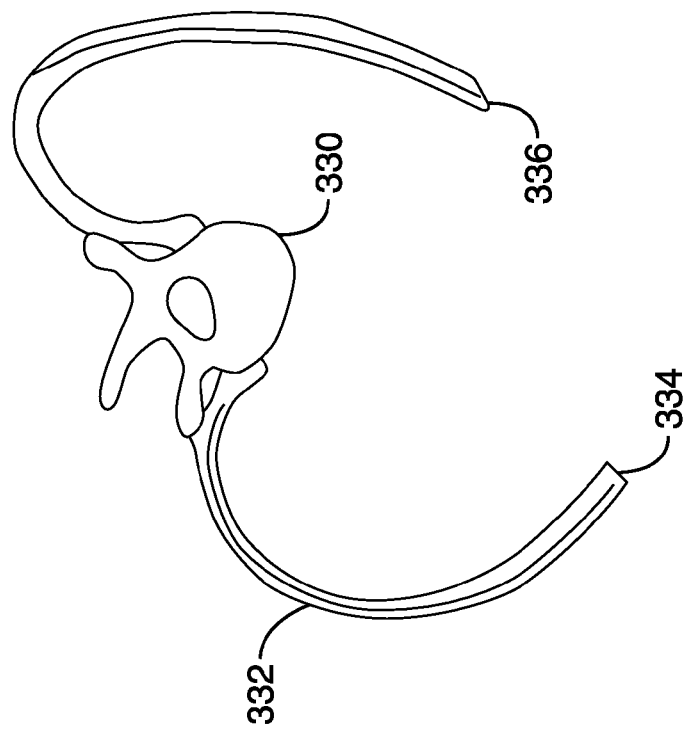

FIG. 20 illustrates abnormal rotation of the vertebrae of the spine as a result of scoliosis.

Figure 21:
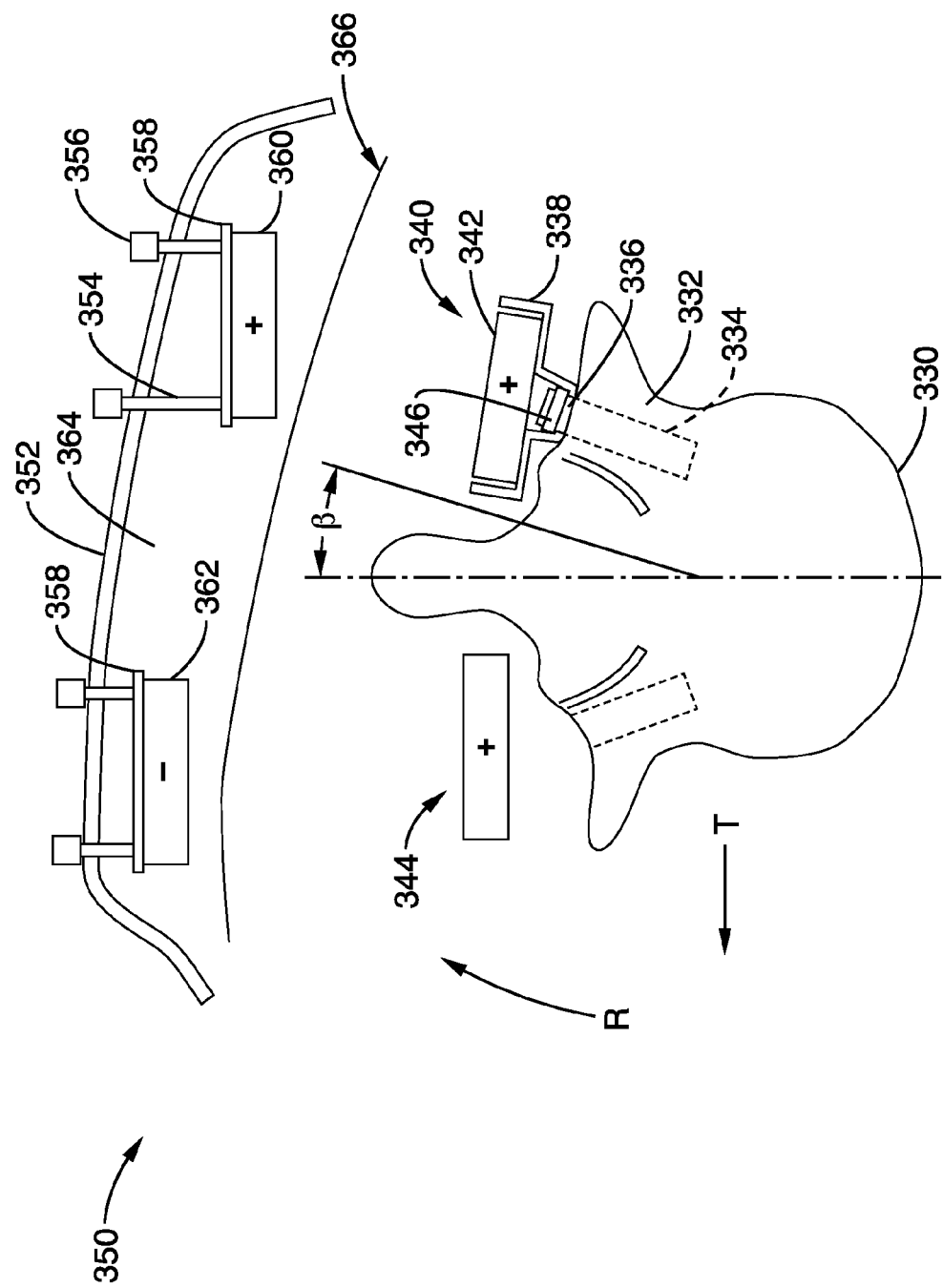

FIG. 21 illustrates another embodiment of the invention for treating scoliosis.

Figure 22:
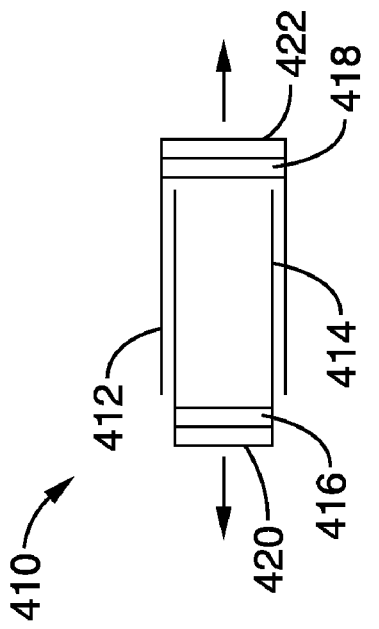

FIG. 22 illustrates an alternative embodiment for delivering a pulsed magnetic field to a body member.

Figure 23:
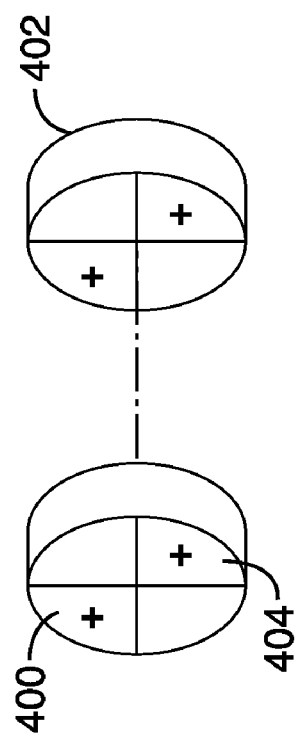

FIG. 23 is a schematic view of an alternative embodiment for delivering a repulsive force to a body member.

Figure 24:
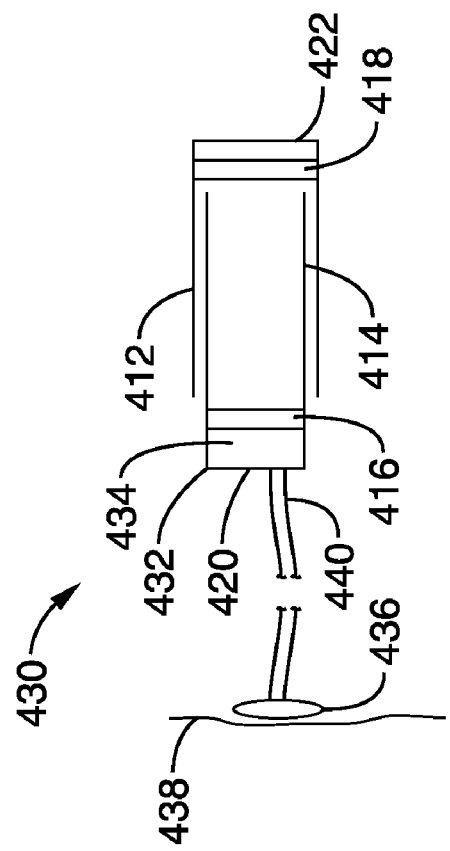

FIG. 24 is a schematic view of the device of FIG. 23 with a fluid pump.

Figure 25:
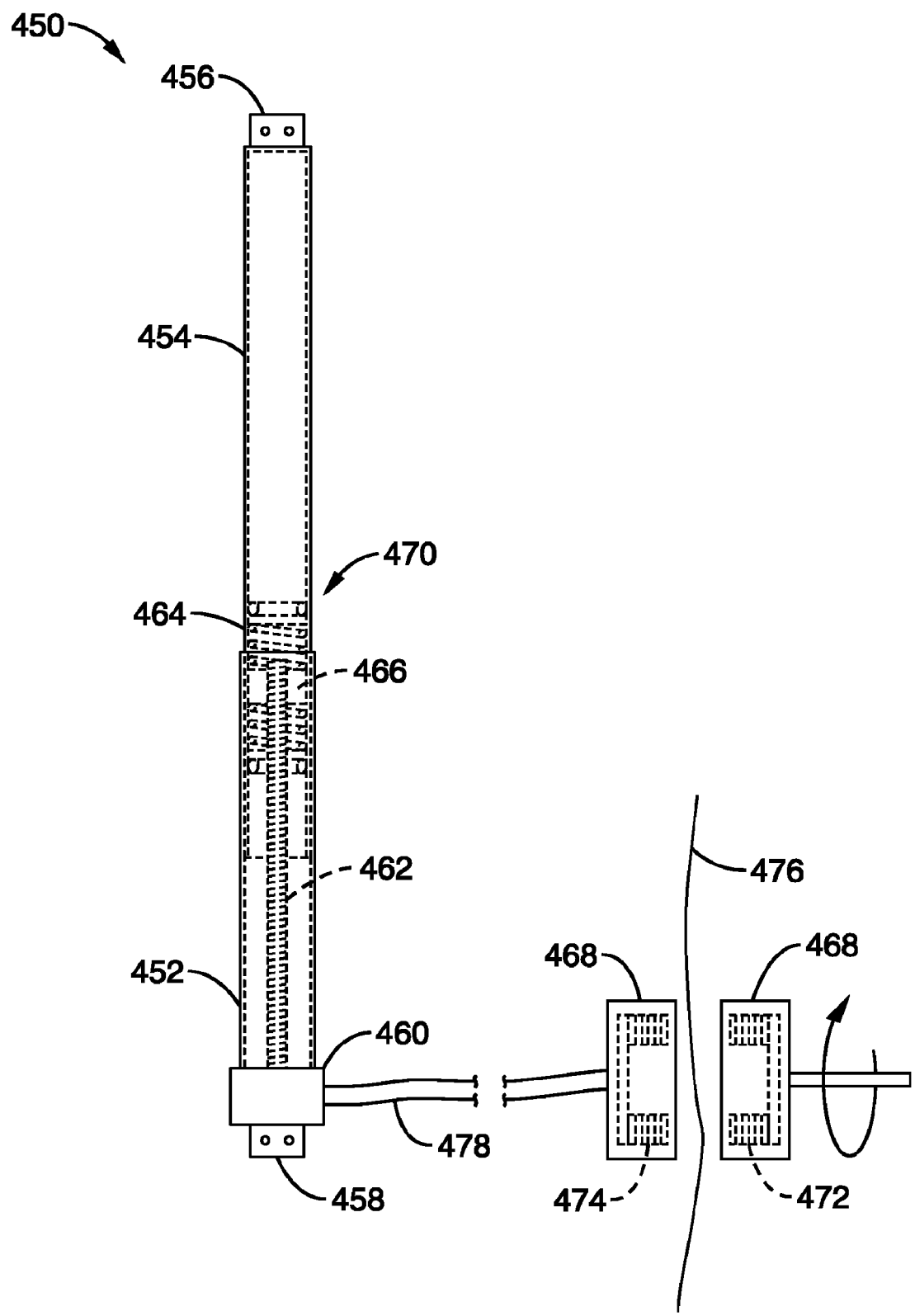

FIG. 25 illustrates an alternative embodiment of a repulsion device incorporating a mechanical jackscrew.

Figure 26:
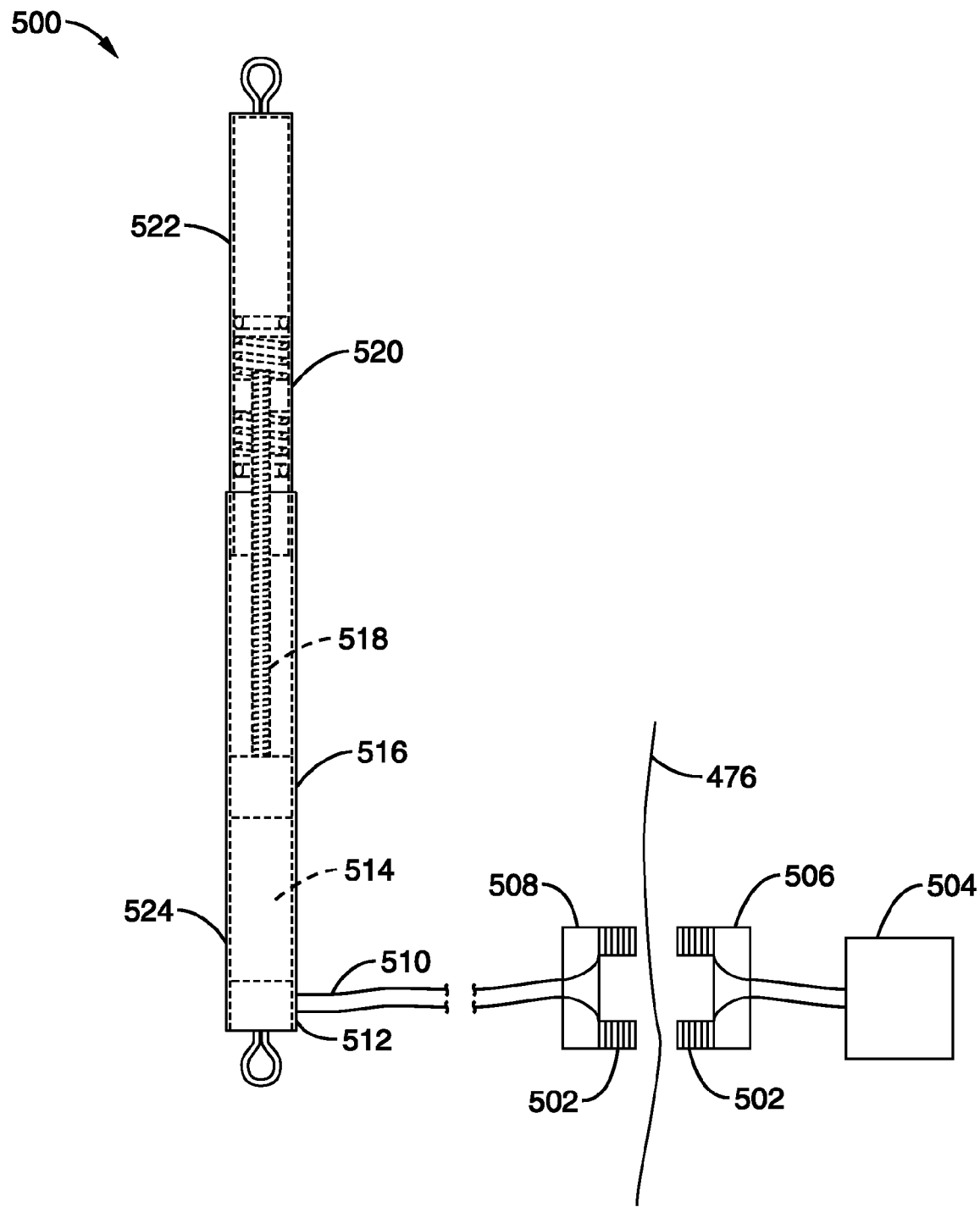

FIG. 26 illustrates an alternative embodiment of a repulsion device incorporating an electric jackscrew.

Figure 27:
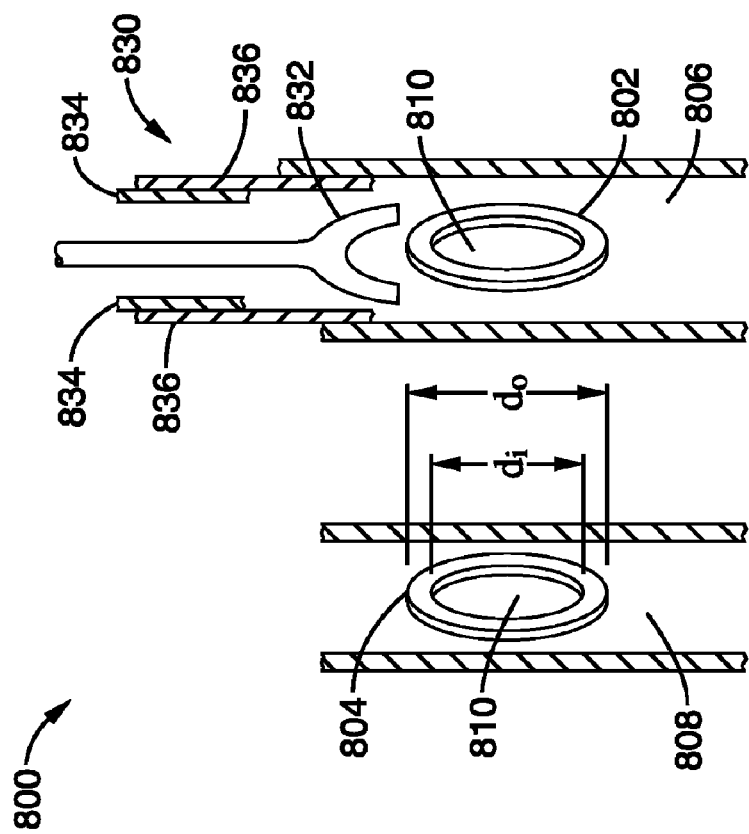

FIG. 27 is a schematic diagram for a system for performing auto-anastomosis between two internal organs using magnetic ring implants in accordance with the present invention.

Figure 28:
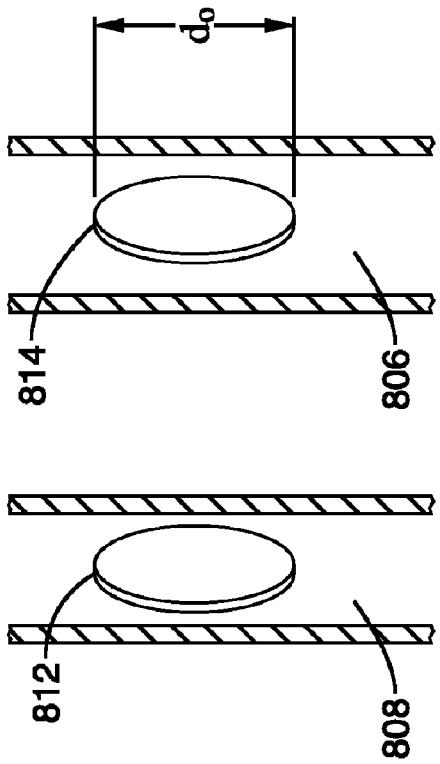

FIG. 28 is a schematic diagram for a system for performing auto-anastomosis between two internal organs using magnetic disc implants.

Figure 29:
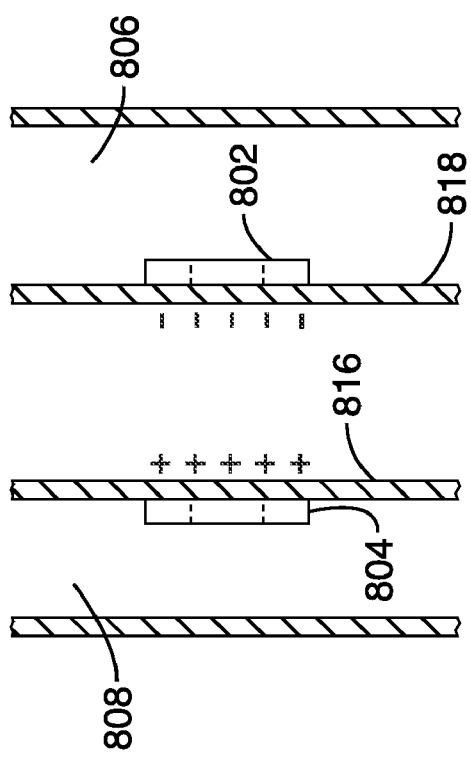

FIG. 29 is another view of the system of FIG. 27 showing the magnetic implants concentrically aligned.

Figure 30:
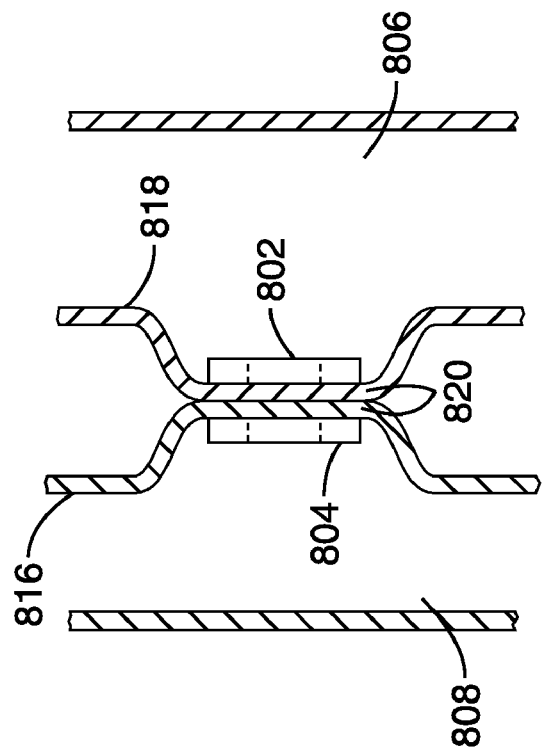

FIG. 30 shows the system of FIG. 27 with the magnets collapsing the visceral walls.

Figure 31:
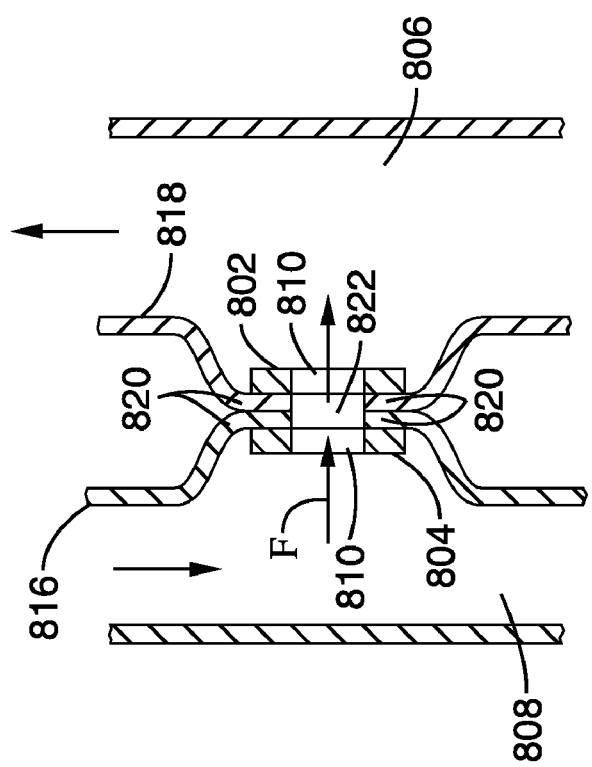

FIG. 31 is a view of the system shown in FIG. 27 with the tissue between the magnets cut out.

Figure 32:
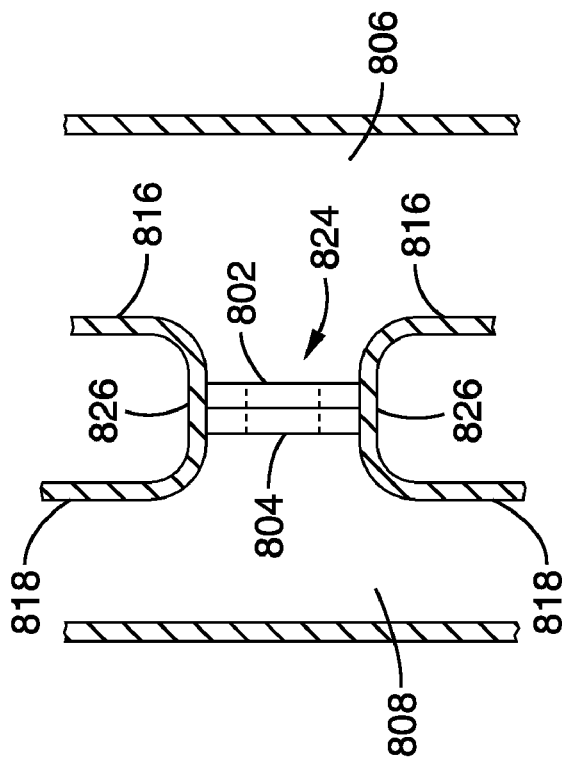

FIG. 32. illustrates the system of FIG. 27 after the tissue between the magnets has necrosed and fallen out, with accompanying anastomosis and fistula.

Figure 33:
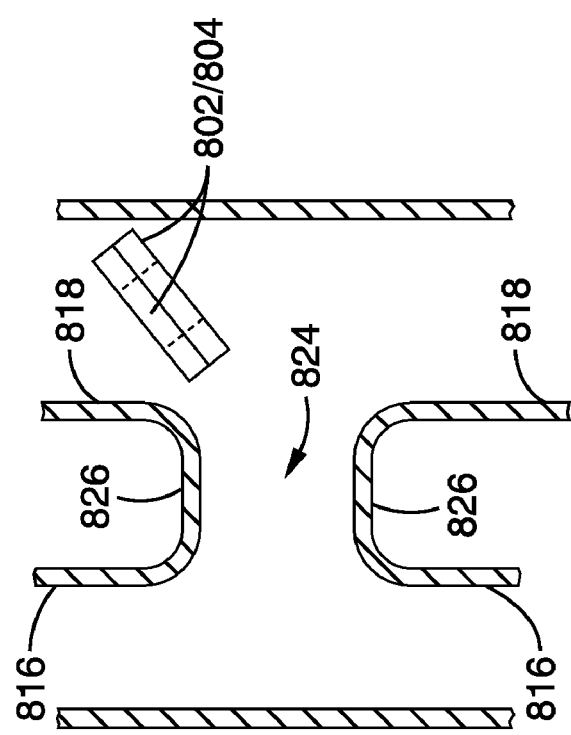

FIG. 33 illustrates the system of FIG. 27 after the magnets have fallen out of the fistula.

Figure 34:
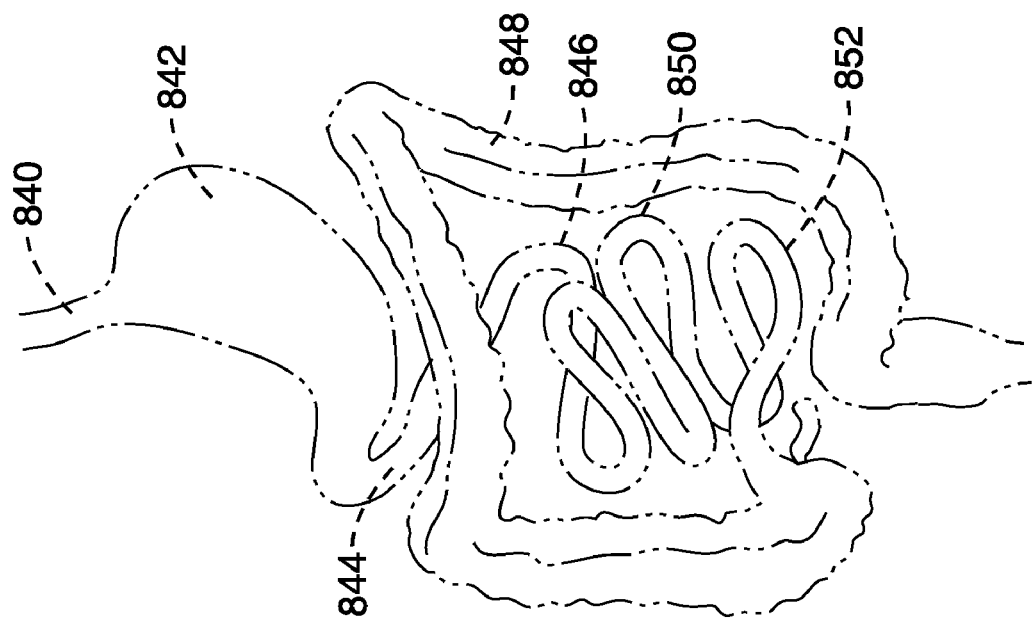

FIG. 34 illustrates an exemplary gastrointestinal tract.

Figure 35:
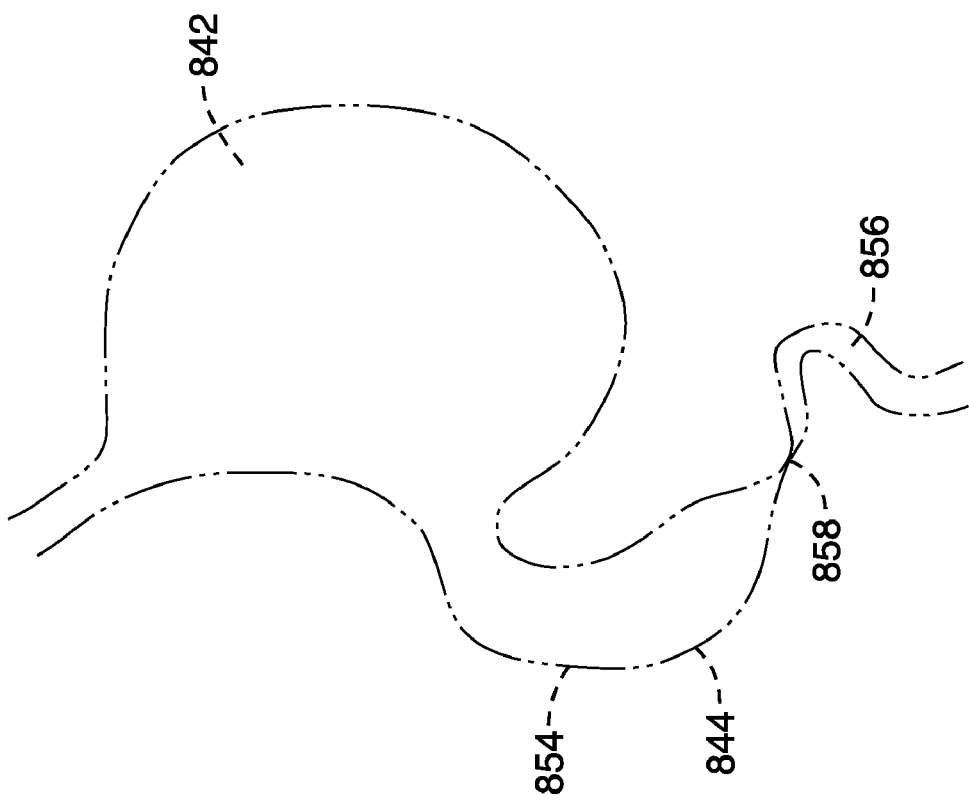

FIG. 35 illustrates a patient with duodenal atresia.

Figure 36:
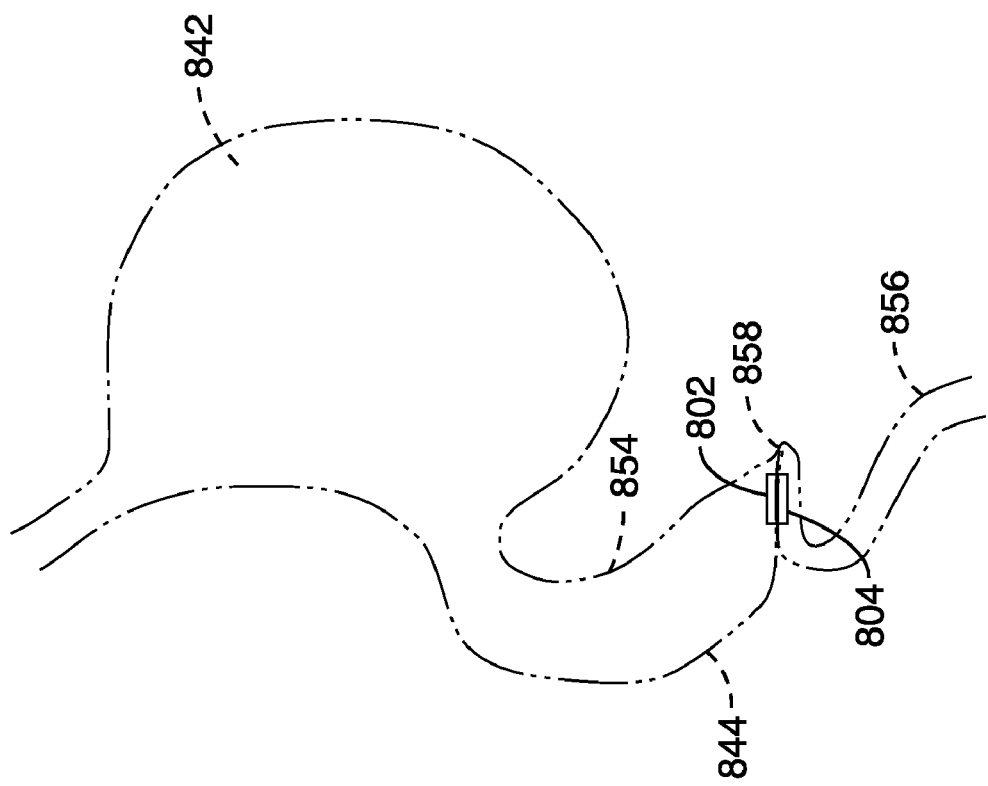

FIG. 36 illustrates a schematic diagram of the system of the present invention used to treat the duodenal atresial.

Figure 37:
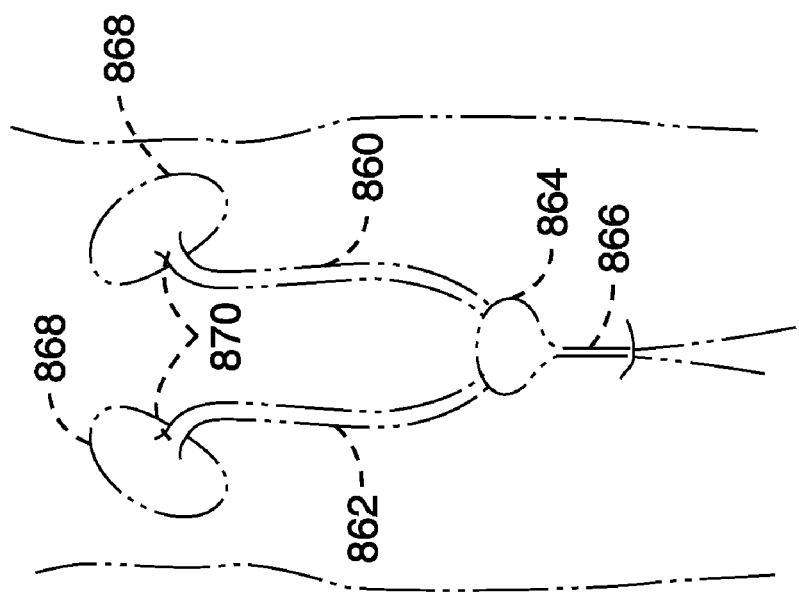

FIG. 37 illustrates an exemplary urinary tract.

Figure 38:
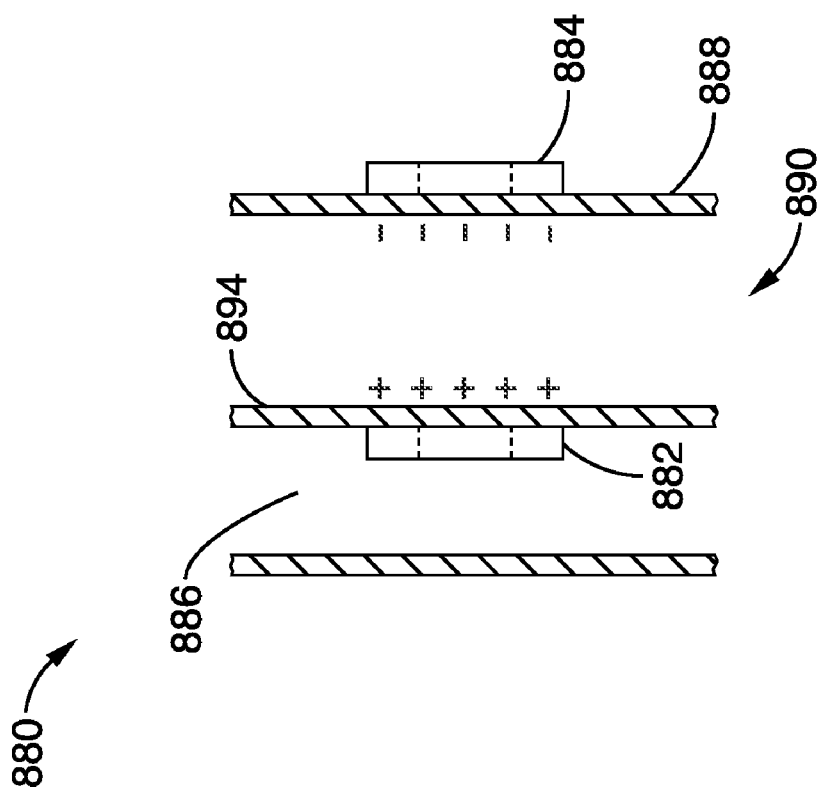

FIG. 38 shows a schematic diagram of a system for creating an ostomy using an internal magnet and external magnet in accordance with the present invention.

Figure 39:
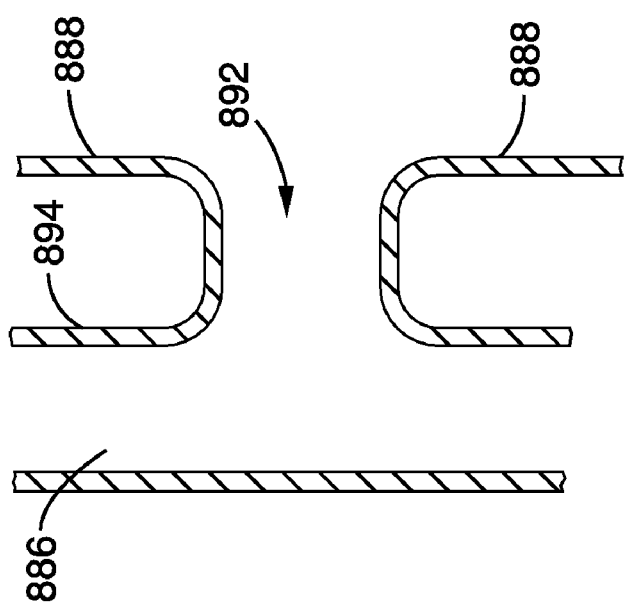

FIG. 39 illustrates a stoma in the abdominal wall created after implementation of the system of FIG. 38.

Figure 40:
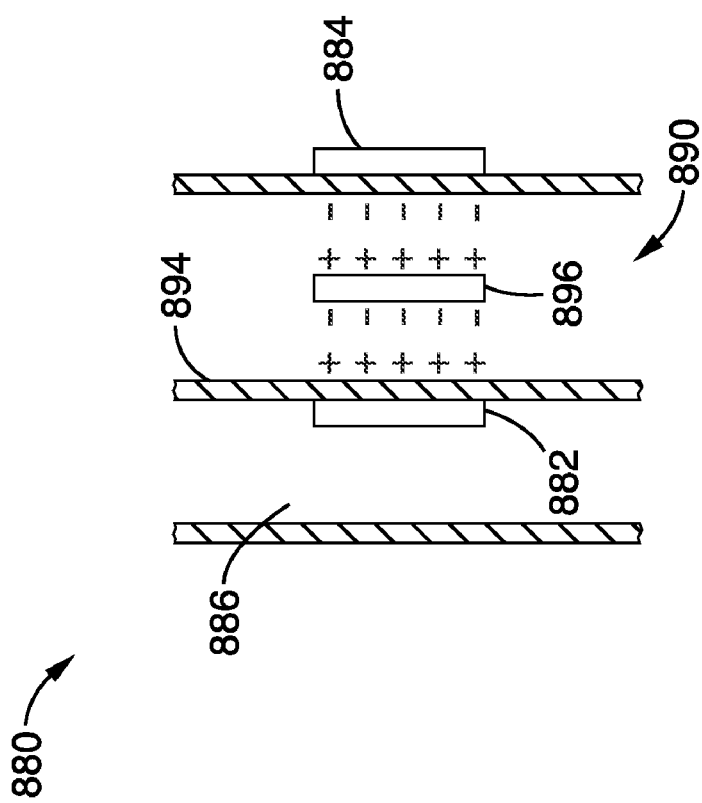

FIG. 40 illustrates the system of FIG. 38 using an intermediate internal magnet.

Figure 41:
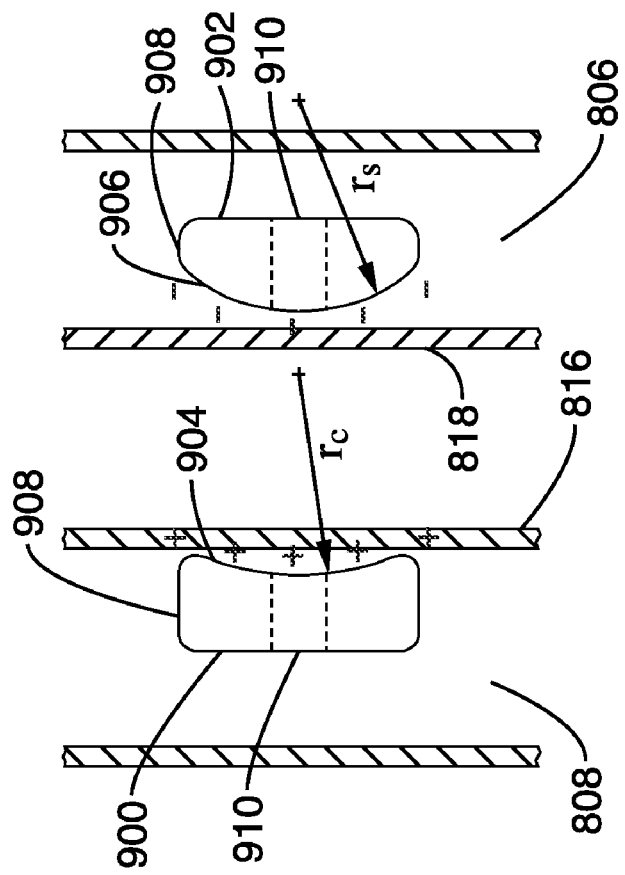

FIG. 41 illustrates two curvilinear magnets disposed opposite one another within two lumen segments inside a patient.

Figure 1:
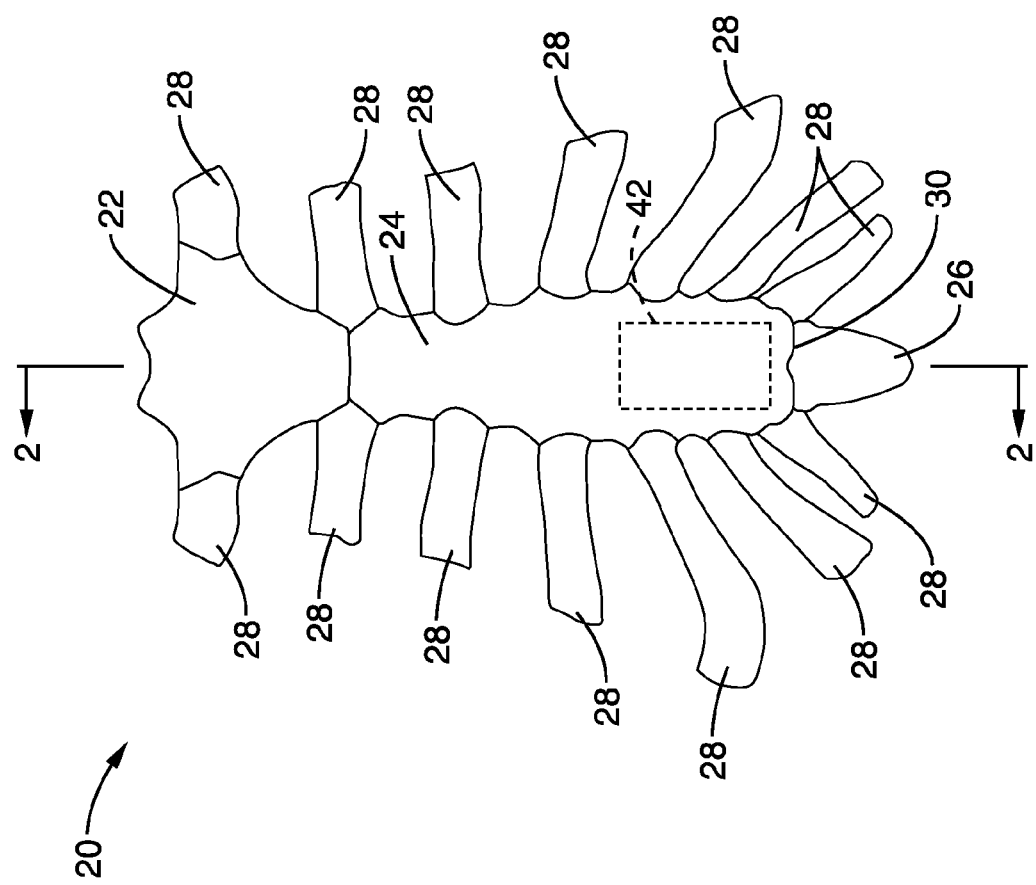
FIG. 1 is a schematic view of a human sternum with an implant according to the present invention installed under the sternum.
Figure 42:
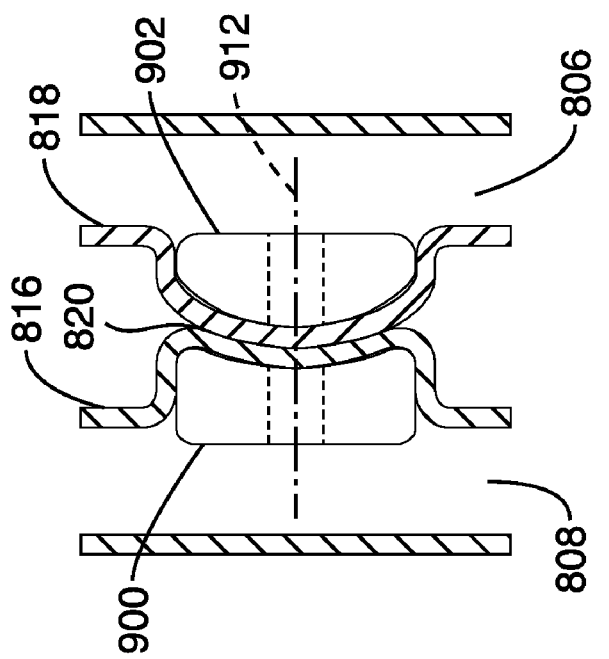

FIG. 42 shows the magnets of FIG. 1 compressing the walls of the two lumen segments.

Figure 43:
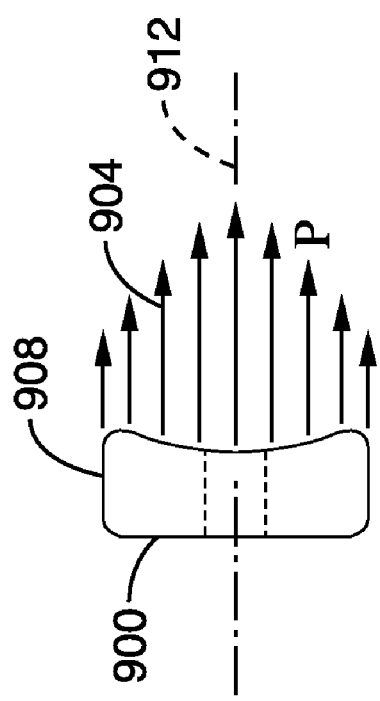

FIG. 43 illustrates a diagram of an exemplary non-uniform loading resulting from the curved surface of the magnet.

Figure 44:
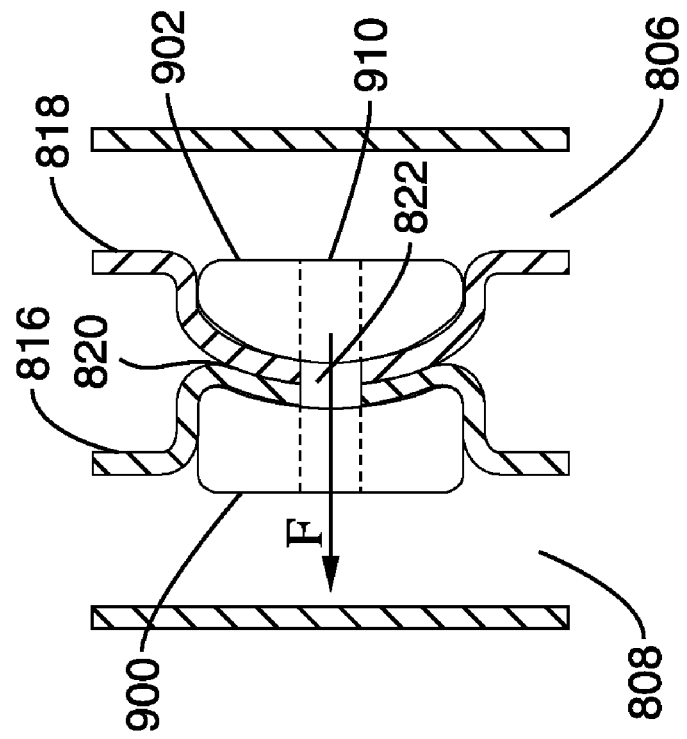

FIG. 44 shows a temporary aperture generated in the lumen tissue in accordance with the present invention.

Figure 45:
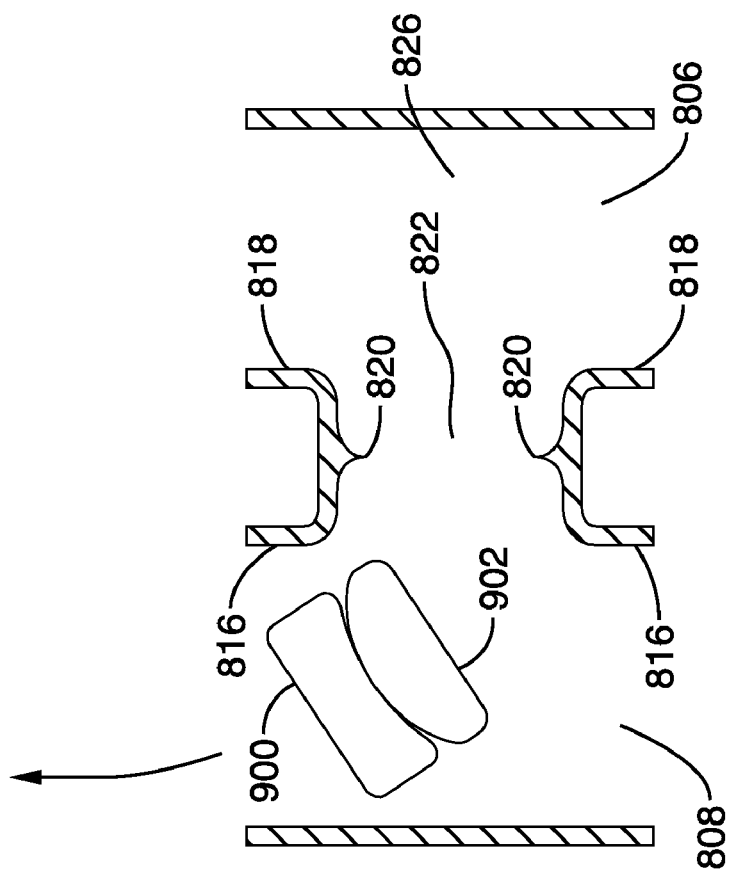

FIG. 45 illustrates a fistula created by the magnets of FIG. 1 in accordance with the present invention.

Figure 46:
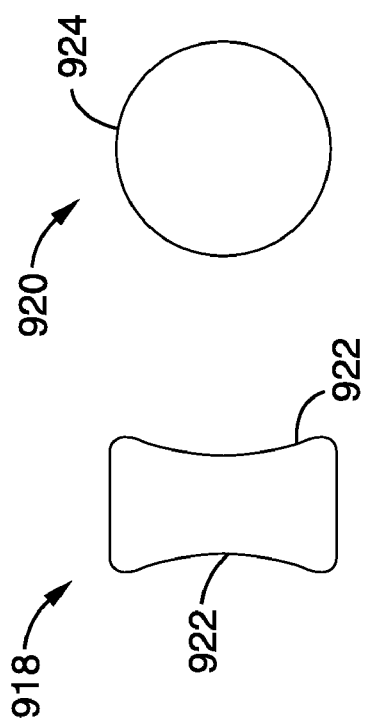

FIG. 46 illustrates an alternative embodiment of the magnets of FIG. 1 having additional curvilinear surfaces.

Figure 47:
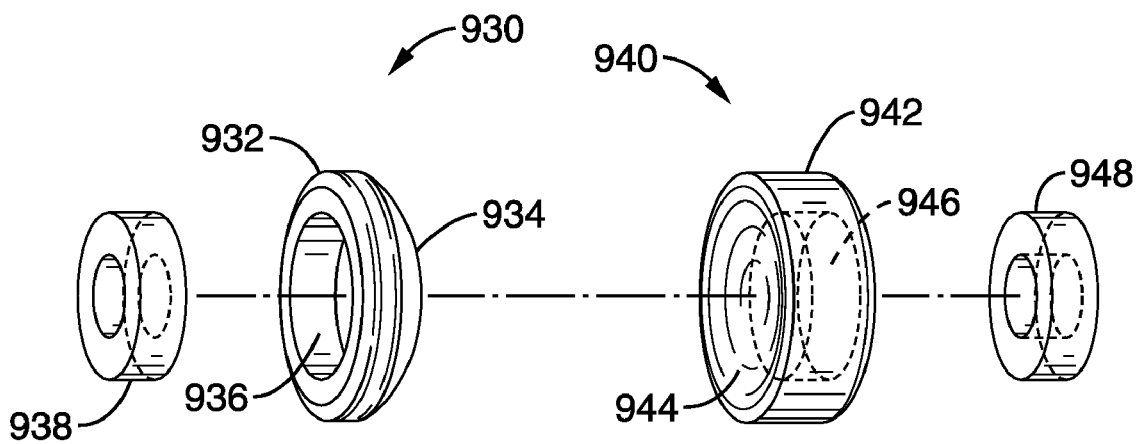

FIG. 47 is an expanded view of curvilinear magnet assemblies in accordance with the present invention.

Figure 48:
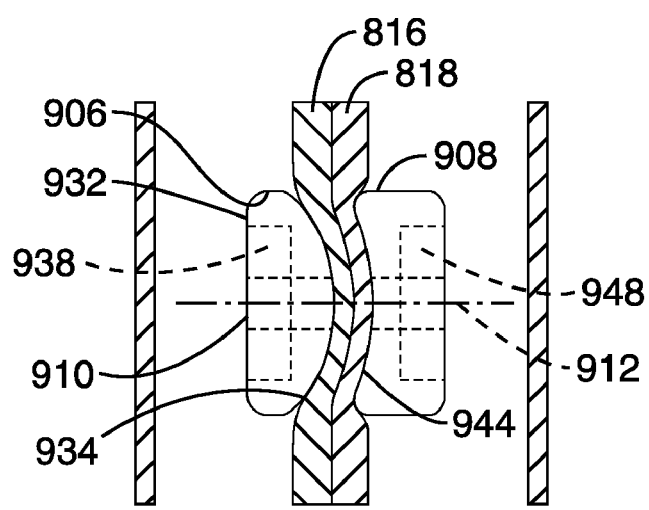

FIG. 48 is a schematic view of the curvilinear magnet assemblies of FIG. 47 positioned at a treatment site in a patient's body.

Figure 49:
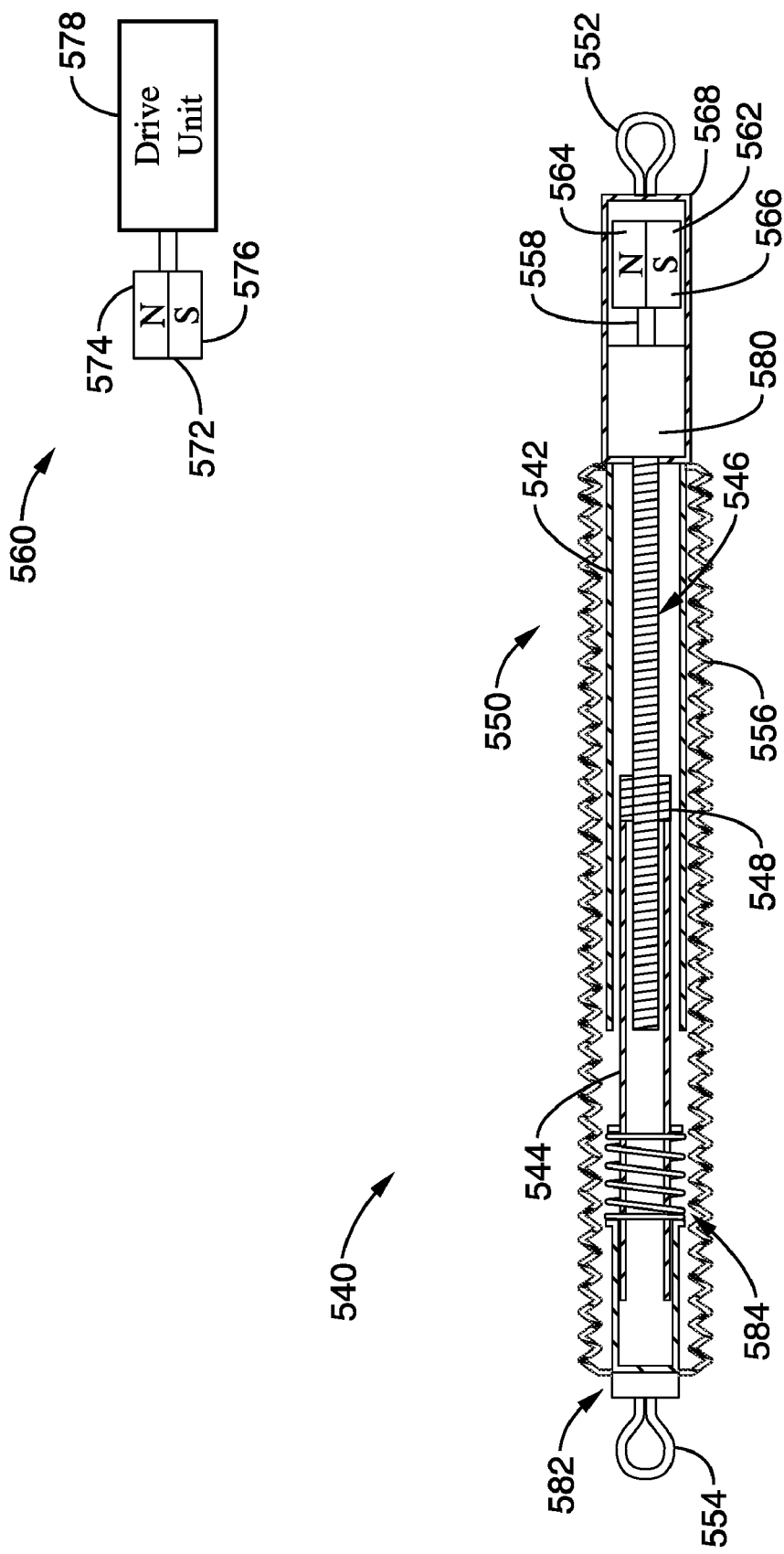

FIG. 49 is a view of an internal jackscrew assembly in accordance with the present invention.

FIG. 50 shows an expanded view of an internal magnet assembly.

FIG. 51 illustrates a cross-sectional view of the internal magnet of FIG. 50.

FIG. 52 illustrates the internal magnet assembly of FIG. 50 installed on the sternum of a patient.

FIG. 53 is an expanded view of an external magnet mount in accordance with the present invention.

FIG. 54 is an expanded view of an external magnet configured to be used with the mount of FIG. 53.

Figure 55:
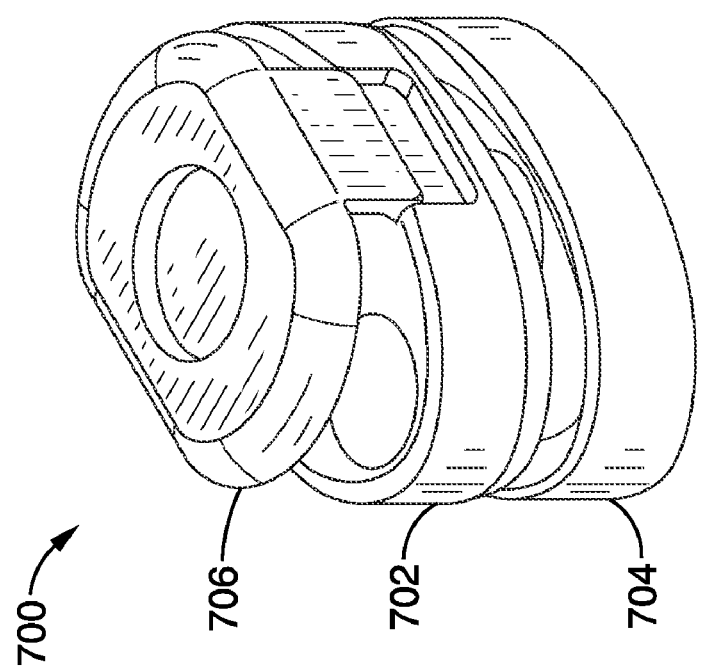

FIG. 55 is a perspective view of an internal magnet assembly for performing an auto-anastomosis in accordance with the present invention.

Figure 56:
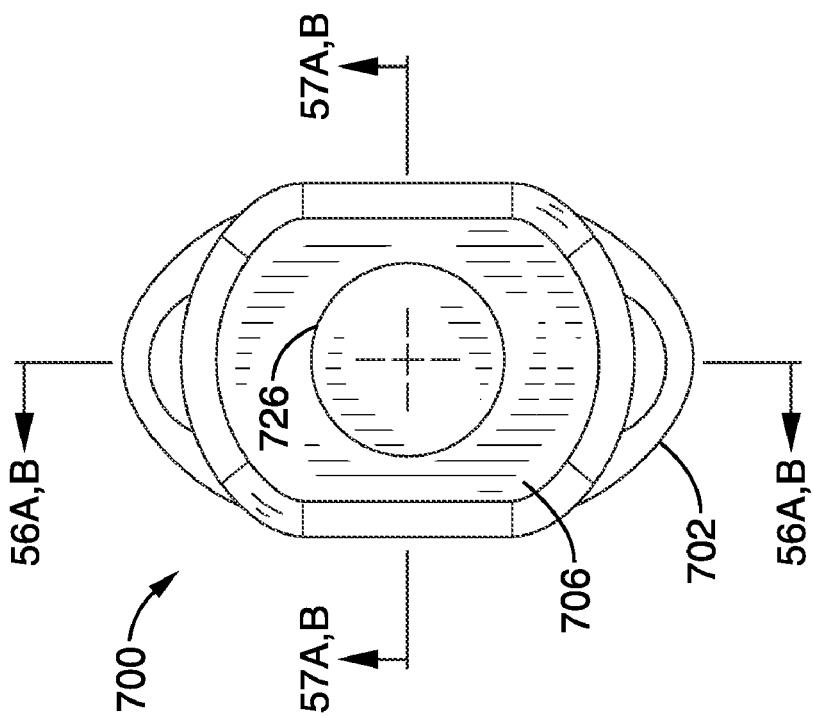

FIG. 56 is a top view of the internal magnet assembly of FIG. 55.

FIGS. 57A-B illustrate cross-sectional views of the internal magnet assembly of FIG. 55 taken across the long axis of the magnetic members, with FIG. 57A illustrating the pre-cut orientation and FIG. 57B illustrating the post-cut orientation.

FIGS. 58A-B illustrate cross-sectional views of the internal magnet assembly of FIG. 55 taken across the short axis of the magnetic members, with FIG. 58A illustrating the pre-cut orientation and FIG. 58B illustrating the post-cut orientation.

FIGS. 59A-B illustrate cross-sectional views of the internal magnet assembly of FIG. 55 taken across the short axis of the magnetic members while implanted on opposing walls of two adjacent viscera, with FIG. 59A illustrating the pre-cut orientation and FIG. 59B illustrating the post-cut orientation.

Figure 60:
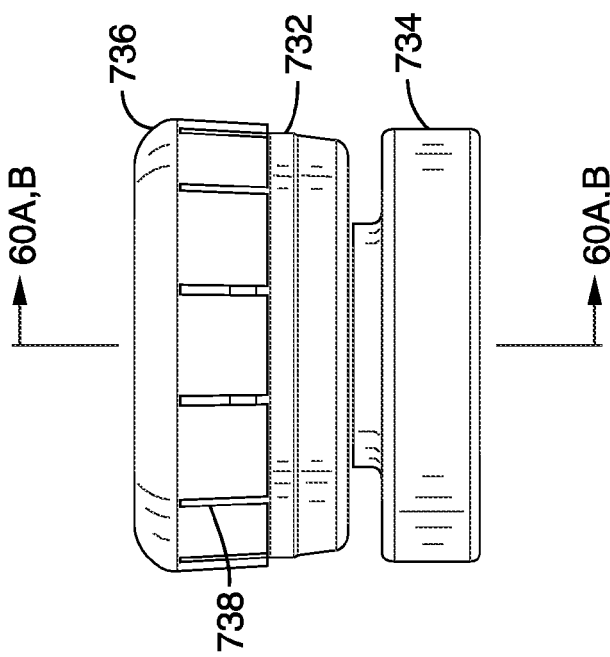

FIG. 60 is a side view of an alternative internal magnet assembly for performing an auto-anastomosis in accordance with the present invention.

Figure 61A:
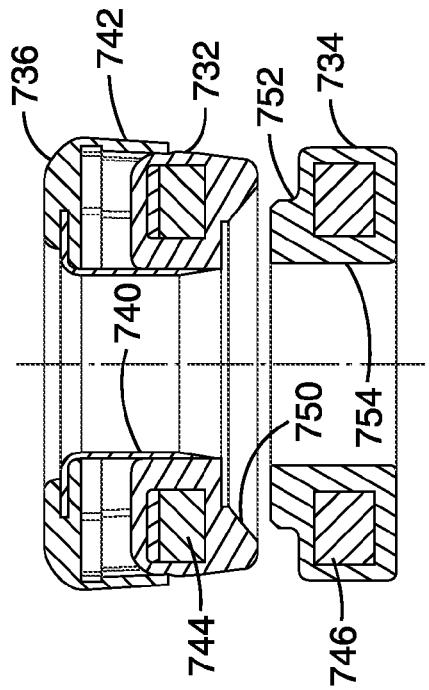
Figure 61B:
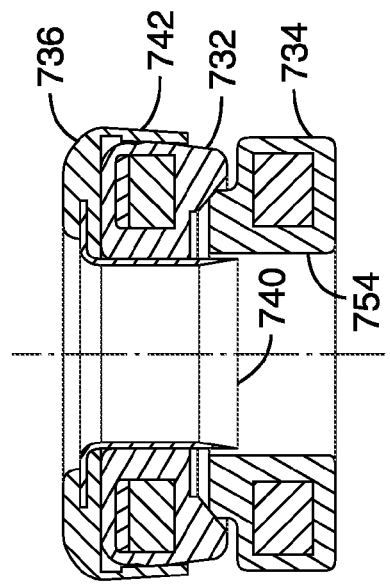

FIGS. 61A-B illustrate cross-sectional views of the internal magnet assembly of FIG. 60, with FIG. 61A illustrating the pre-cut orientation and FIG. 61B illustrating the post-cut orientation.

Figure 62:
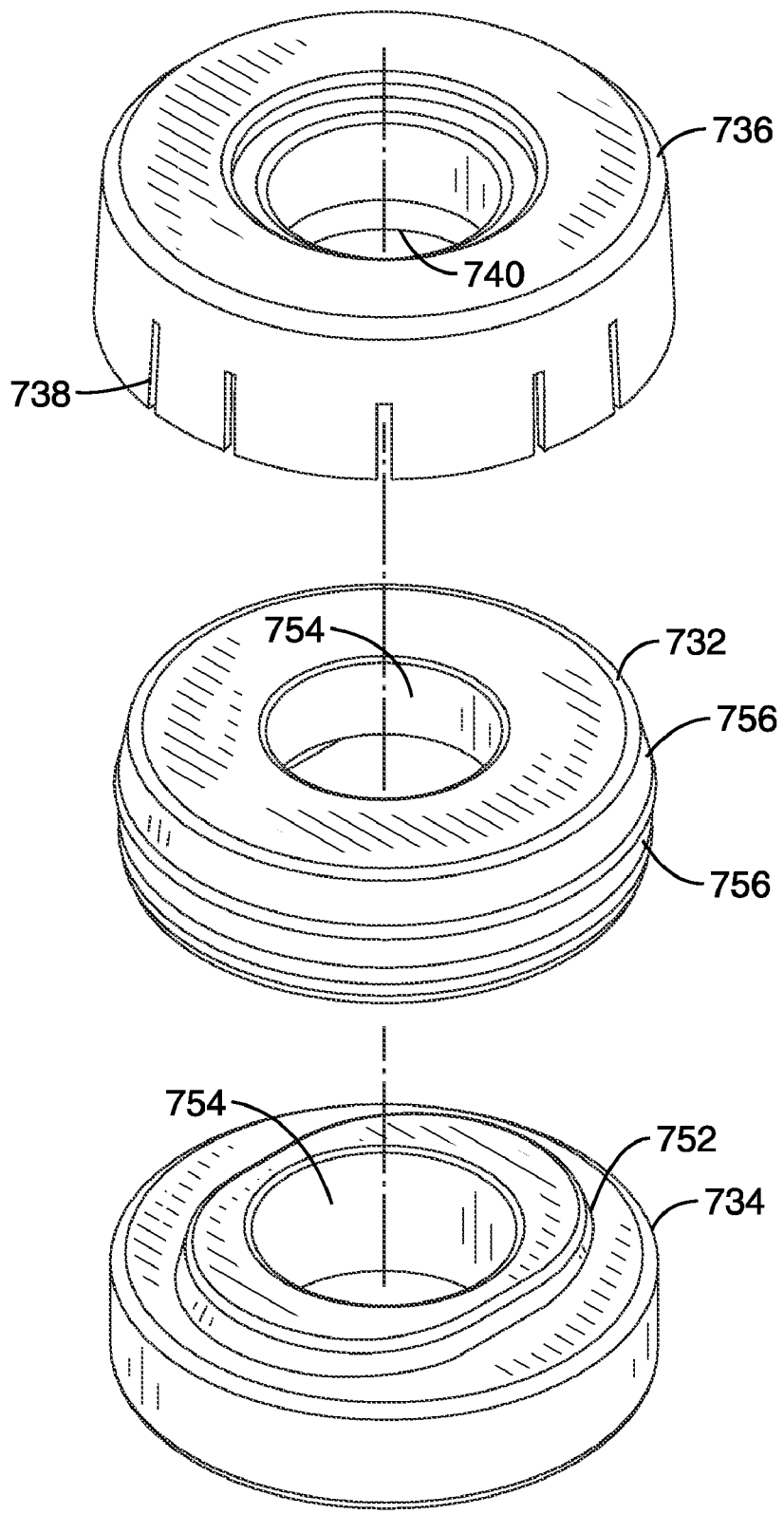

FIG. 62 is an upper-perspective, exploded view of the internal magnet assembly of FIG. 60.

Figure 63:
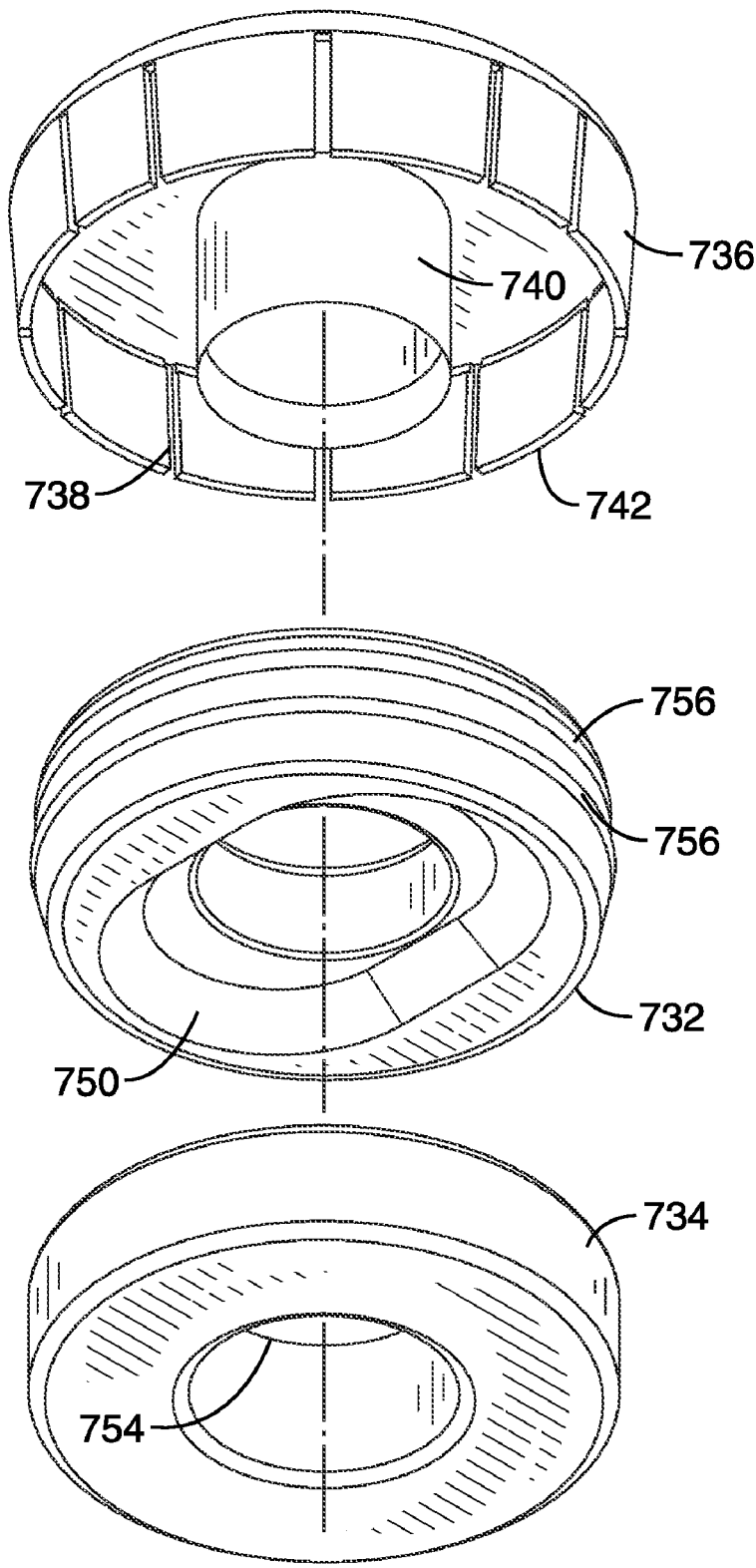

FIG. 63 is a lower-perspective, exploded view of the internal magnet assembly of FIG. 60.

Figure 64:
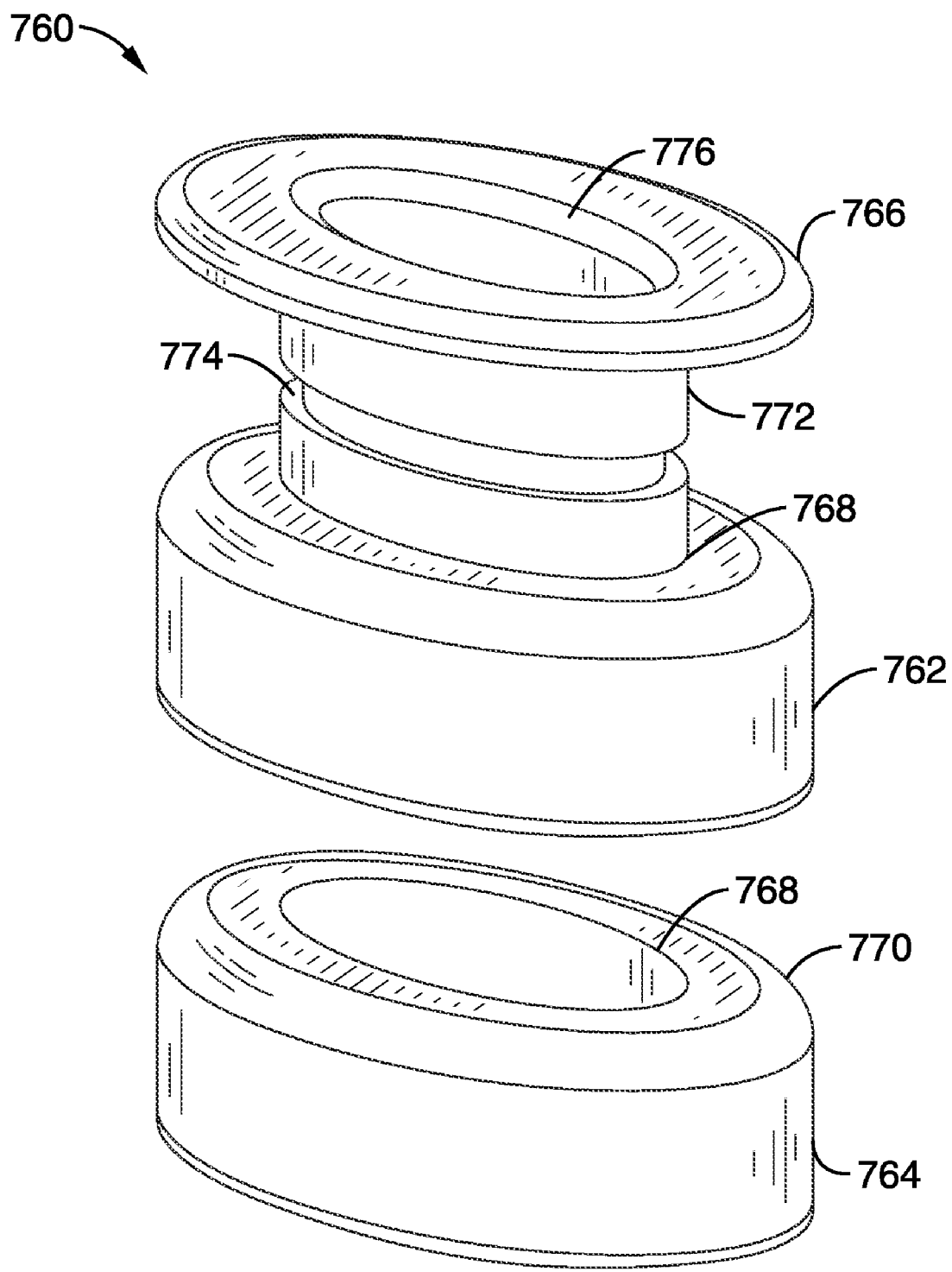

FIG. 64 is an upper-perspective, exploded view of another embodiment of an internal magnet assembly for performing an auto-anastomosis in accordance with the present invention.

Figure 65:
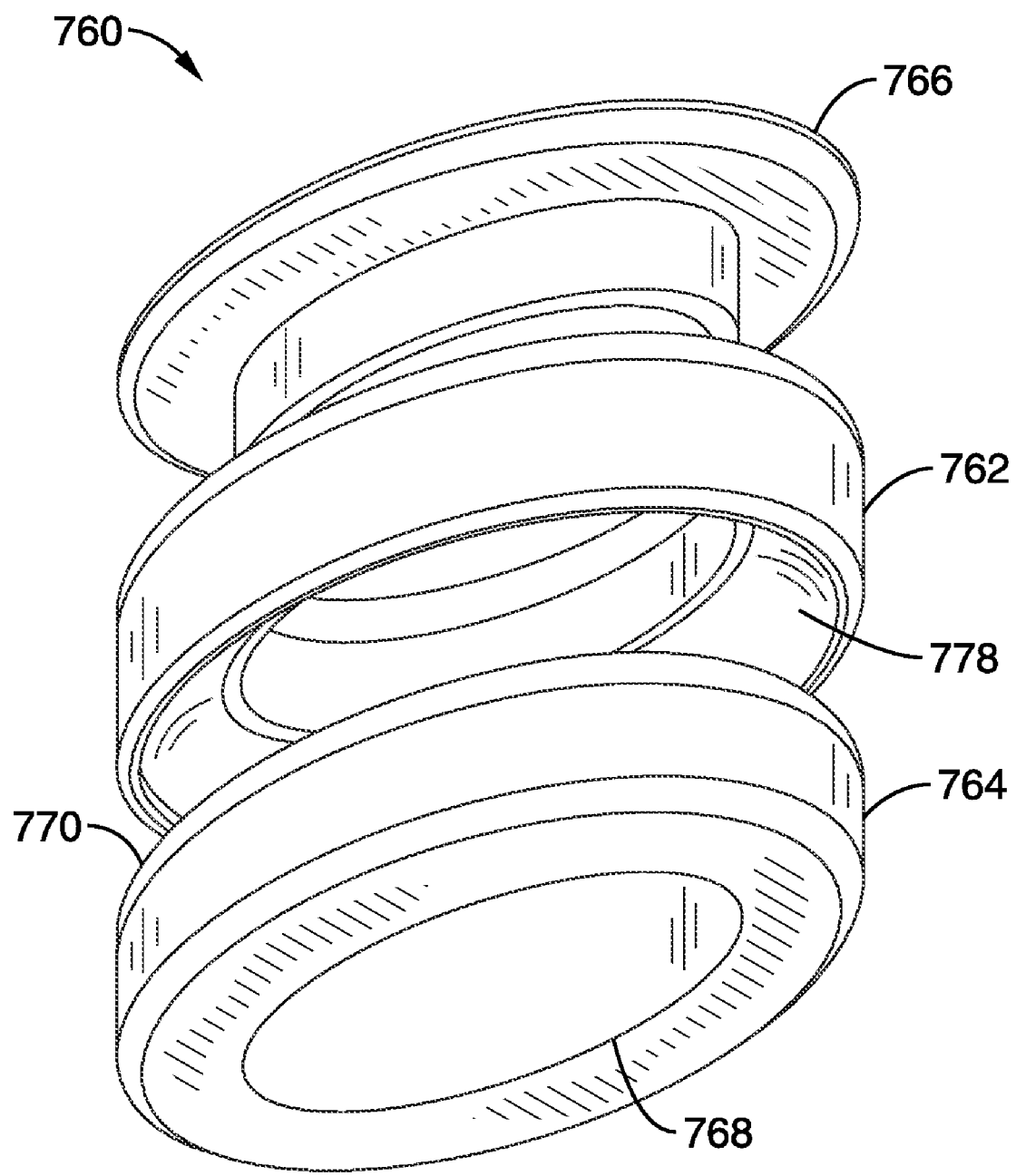

FIG. 65 is a lower-perspective, exploded view of the internal magnet assembly of FIG. 64.

Figure 66A:
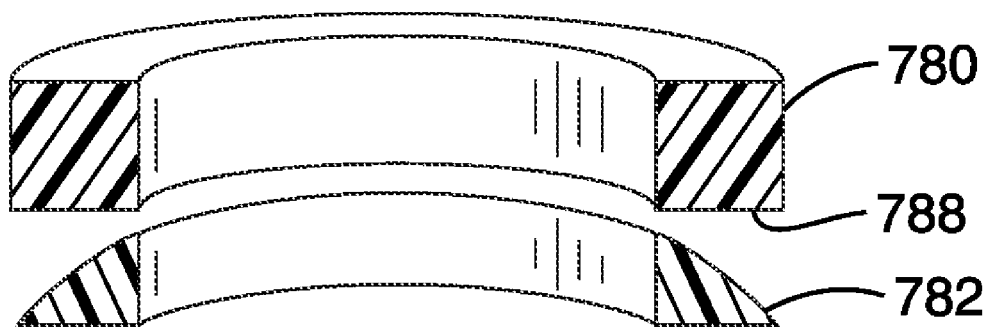
Figure 66B:
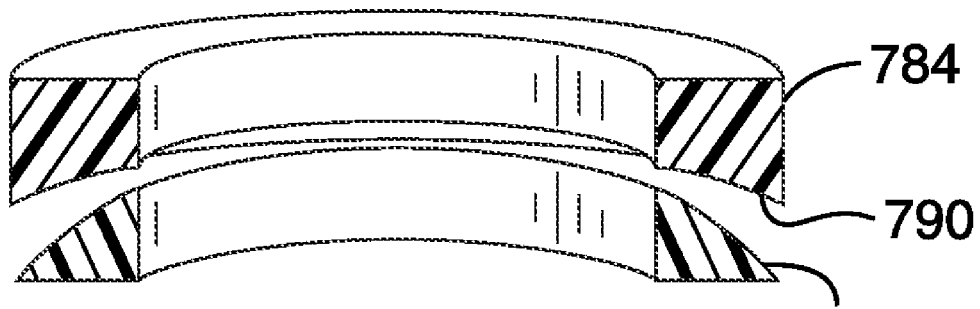
Figure 66C:
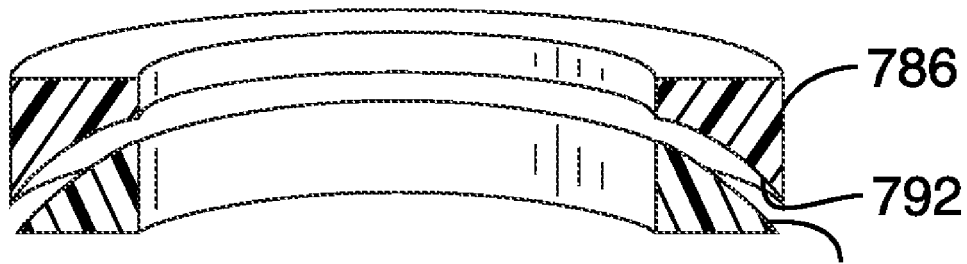

FIGS. 66A-C illustrate separate embodiments of mating surface variations that may be used in an internal magnet assembly for performing an auto-anastomosis in accordance with the present invention.

Figure 67:
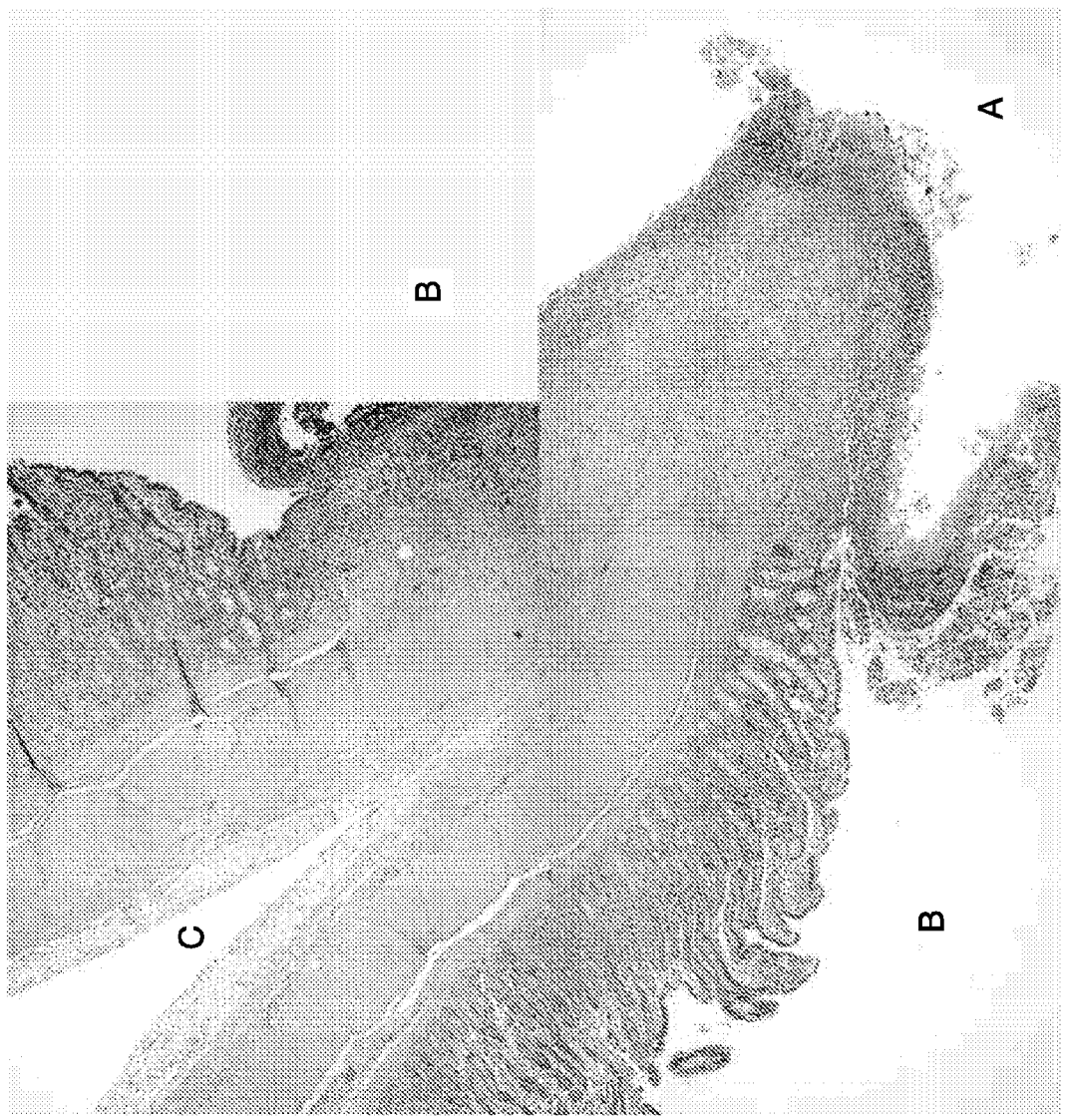

FIG. 67 illustrates a tissue sample of an auto-anastomosis performed under the system and methods of the present invention.

DETAILED DESCRIPTION OF THE INVENTION

Referring more specifically to the drawings, for illustrative purposes the present invention is embodied in the apparatus and methods generally shown in FIG. 1 through FIG. 17 and FIGS. 21-26 and 27-67. It will be appreciated that the apparatus may vary as to configuration and as to details of the parts, and that the methods may vary as to the specific steps and sequence, without departing from the basic concepts as disclosed herein.

The present invention utilizes a system in which a small magnet is implanted in cooperation with an internal body member to apply a corrective force to the body member by virtue of its attraction to an adjustable magnet in an external device that is comfortable and cosmetically pleasing.

Small rare earth metal magnets can produce considerable force and can be manipulated in terms of size, shape and position. This force can be used to alter growth and development of skeletal structure and soft tissue. The biology of tissue response to force has been well studied. Clinical application of this powerful biologic principle has been limited by the difficulties of applying force through external bracing or through internal pins manipulated by external devices (e.g., bone lengthening through distraction osteogenesis). Magnetic force fields can be used to apply force to implanted magnets attached to an internal structure without violating the skin and soft tissue. The magnetic force field can be manipulated externally to adjust the direction, strength and speed at which the deformity is corrected.

1. Pectus Excavetum

FIGS. 1-16 illustrate a preferred embodiment of the invention relating to the correction of pectus excavetum. FIG. 1 illustrates a schematic, anterior view of a human sternum 20. The sternum 20 is an elongated, flatted bone, forming the middle portion of the anterior wall of the thorax. The sternum 20 generally consists of three parts: the manubrium 22, which at its upper end supports the clavicles (not shown); the body or gladiolis 24, which interfaces at its upper end with the lower end of the manubrium 22, and the xiphoid process 26, which interfaces at its upper end with the lower end of the gladiolis 24 at junction 30. The margins of sternum 20 articulate with the first of seven pairs of ribs 28.

Figure 2:
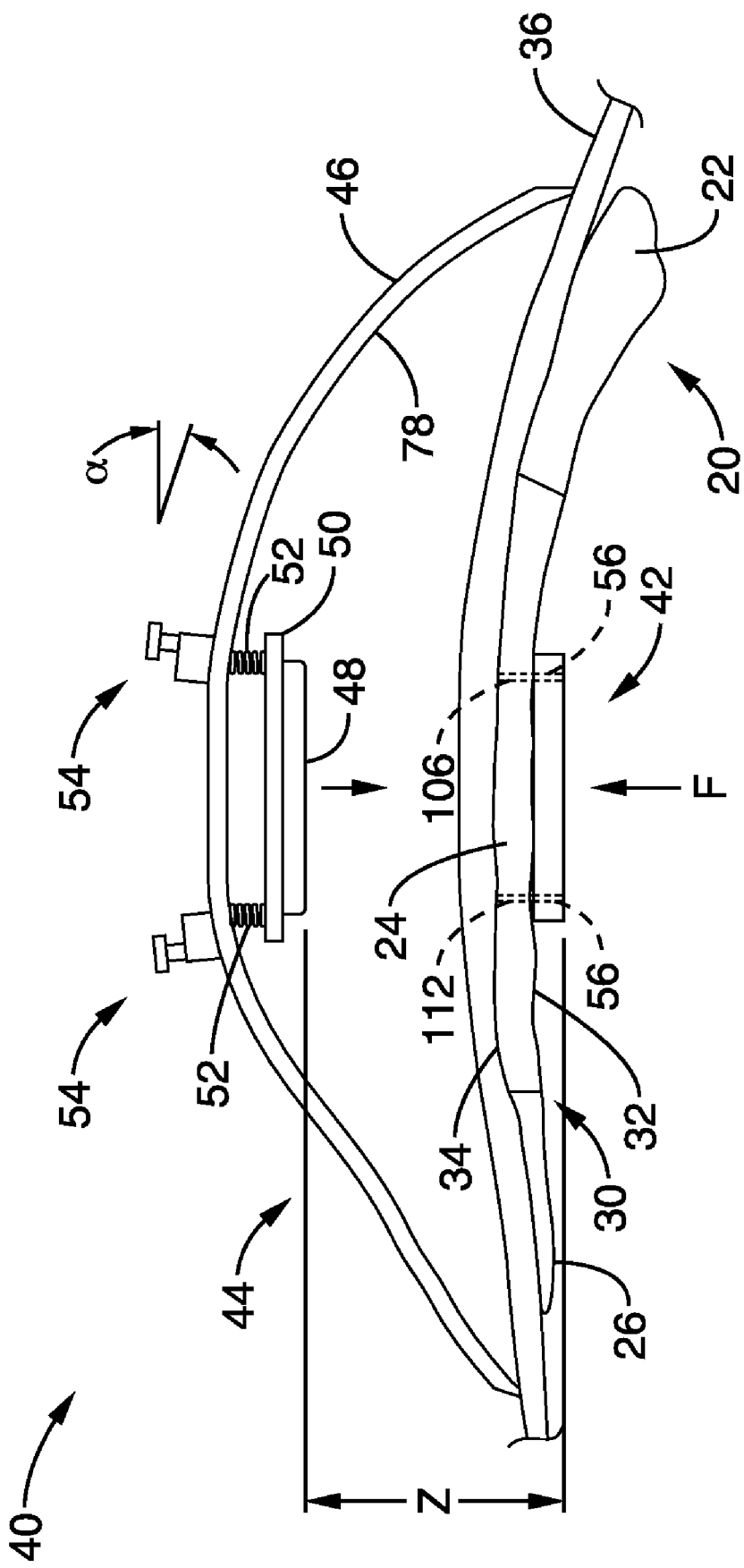
FIG. 2 is a cross-sectional schematic view of the platform of the present invention installed over a patient's chest and an implant installed under the sternum.

As shown in FIG. 1 and illustrated as a cross-sectional view of a corrected patient's chest in FIG. 2, a magnetic substernal implant 42 may be installed on the posterior surface 32 the body 24 of the sternum 20, just above the xiphoid process 26. Illustrated in greater detail in FIG. 3, the implant 42 preferably comprises a rare earth magnet 90, or an array of rare earth magnets housed in casing 92. The casing 92 may comprise any biocompatible material such as medical grade epoxy, titanium or suitable material used in the art. Casing 92 preferably has mounting holes 56 for fixation at each corner. The casing 92 may also have a plurality of protrusions 94 to enhance the attachment of the implant 42 with the sternum 20.

The magnetic implant 42 is sized to fit comfortably behind the sternum. An exemplary implant may 3 inches long, 2½ inches wide and 3/16 thick. However, the size of the implant may vary according to patient anatomy.

FIG. 2 and FIGS. 5-13 illustrate an exemplary method of surgically installing the implant 42. A 3 cm substernal transverse incision 58 is made through the patient's skin 36. The ziphoid process 26 is then separated from the lower sternum body 24 and a pocket is bluntly dissected behind the posterior surface 32 of the sternum, as illustrated in FIG. 6.

The implant 42 is attached to the posterior surface of the sternum with sutury passed through the holes 112 in the sternum illustrated in FIG. 2. Using laparoscopic or arthroscopic visualization, a drill guide 100 is inserted and positioned over the proximal end of the sternum body 24, as shown in FIGS. 7 and 8. A small stab wound is made into skin 36, and the drill sleeve 102 is inserted through the guide 100. The sternum 20 is then drilled under direct visualization to bore one or more distal bores 106 from the anterior surface 34 of the sternum through to the posterior surface 32. Distal bores 106 preferably line up with the corresponding mounting holes 56 in casing 92.

Referring now to FIG. 9, a distal suture 108 is looped through one of the mount holes 56 of casing 92. The distal suture 108 preferably comprises a heavy braided suture commonly used in the art, e.g. #2 or #5 ticron. The suture is then fed under the sternum 20 and a suture retriever 110, such as a Hewson type, is used to pull the distal suture 108 through the corresponding distal bore 106 in the sternum body 24 and the anterior skin stab wound. The process is repeated for the second corner of the distal end of the casing 92.

Referring now to FIG. 10, the proximal end 114 of skin 36 and subcutaneous tissues from the anterior sternum proximal to the sterno-xiphoid junction 58 are pulled back to expose the proximal end of the sternum body 24. The drill guide 100 is moved transversely along the sternum body 24 to the exposed portion of the sternum under proximal end 114. Once sufficient exposure is obtained, one or more proximal bores 112 are drilled under direct vision through the sternum anteriorly-to-posteriorly, thus providing anchoring points for all corners of the casing 92.

Now referring to FIGS. 11 and 12, a proximal suture 116 is looped through one of the mount holes 56 on the proximal end of casing 92. The suture is then fed under the sternum 20 and suture retriever 110 is used to pull both ends of the proximal suture 116 through the corresponding proximal bore 112 in the sternum body 24. The process is repeated for the second corner of the proximal end of the casing 92.

As seen in FIG. 12, both sets of proximal and distal sutures 116, 108 are pulled to guide the implant 42 up behind the sternum 20 and maintain the apposition of the casing 92 to the sternum 20 with traction on the sutures.

Referring now to FIG. 13, the proximal sutures 116 are tied down firmly over the sternal bone bridge to secure the implant 20 to the proximal surface 32 of the sternum. Under direct vision, the process is repeated for the distal sutures 108.

Although FIGS. 9-13 illustrate a preferred embodiment using suture to fasten the implant 42 to the sternum 20, it is appreciated that any number of different fastening means commonly known in the art may be used to secure the implant 42. For example, bolts (not shown) may be passed through bores 106, 112, threaded into threaded mounting holes 56 of casing 92 and torqued down to secure the implant 42 to the posterior surface 32 of the sternum 20. Alternatively, the implant may be fastened to either the posterior or anterior sides of the sternum via cables that wrap around the sternum. In this configuration, since the implant is closer to the platform, the internal magnetic member may be any magnetically responsive material, such as an iron plate with biocompatible coating (e.g. titanium).

Surgical placement generally requires a brief outpatient general anesthesia. The procedure takes about 30 minutes and requires minimal post-operative analgesia.

FIGS. 2 and 14-17 illustrate several embodiments of an external magnet platform of the present invention for treating pectus excavatum. FIGS. 14 and 15 show an embodiment having a platform 40 configured to be worn over a patient's chest. Platform 40 comprises a chest plate 44 sized according to the patient's anatomy. Generally, a mold is made of the individual's chest deformity. From this the desired end point position of the sternum and chest wall shape are molded to create the chest plate 44. FIG. 14 is a bottom view of platform 40, showing the underside 78 of chest plate 44. In addition to being contoured to comfortably rest on the patient's chest, the underside 78 of the chest plate is cut away to create cavity 68 that allows the chest to expand outward as a result of treatment.

In a first configuration, an external magnet 48 is hung from the underside 78 of the chest plate 44 by a plurality of adjustment cables 62. External magnet 48 is preferably a rare earth magnet, or array of rare earth magnets. The external magnet has an adjustable stage, or mounting plate 50, which has a plurality of holes 70 to secure cables 62. As illustrated in FIGS. 14 and 15, the magnet 48 is hung with 4 cables. However, other configurations, such as a three cable design (not shown), may also be used. The cables 62 are coupled to the chest plate via adjustment members 54. Cables 62 lead from the magnet plate 50 out to the exterior surface 46 and back through to the underside of the chest plate via through holes 64 to terminate at adjustment member 54. One or more biasing springs 52 may be imposed between the chest plate 44 and the magnet 48, creating a tensile force on cables 62 so that the magnet is biased to the furthest orientation away from the chest plate 44 that is allowed from the cables' length.

By turning adjustment member 54 from the top of the chest plate illustrated in FIG. 15, the cable 62 may be shortened, thereby advancing one corner of the magnet plate 50 upward toward the chest plate 44. By rotating the adjustment member in the opposite direction, the cable is extended, thereby advancing one corner of the magnet plate 50 toward from the patient's chest and away from the chest plate 44. When all the adjustment members are moved the same increment, the magnet will translate toward or away from the patient's chest in the Z axis (see FIGS. 2 and 14). The magnet may also be rotated angle θ about the X or Y axis by manipulating the adjustment members 54 to lengthen or shorten one or more cables 62 with respect to the remaining cables.

The external magnet 48 and the implant magnet 90 are configured so that their opposite poles face each other, thereby generating an attractive force between the two magnets. By manipulating the distance of the external magnet 48 from the chest plate 44 in the Z direction, the amount of force applied to the internal magnet can be incrementally tuned or adjusted. By manipulating the orientation of the external magnet 48 with respect to the chest plate 44 in the X and Y directions, the direction of force applied to the internal magnet can be incrementally adjusted.

The chest plate 44 is preferably comprised of a rigid material, such as a rigid thermoplastic or polymer or steel reinforced polymer that does not deform as a result of the magnetic forces, allowing external magnet 48 to remain stationary with respect to the patient's chest. As a result of the constant force applied from the external magnet 48, the implant 42 imposes a corrective outward force F on the posterior surface 32 of the sternum 20. This outward force incrementally repositions/deforms the sternum 20 to move outward from the patient's chest cavity. By adjusting the angle of the external magnet in the X and Y directions, the force generated on the implant 42 may be directed to orient the sternum in the X and Y axes as well to correct asymmetric lesions.

An initial adjustment of the platform is made after the implant is placed in the outpatient surgical procedure. When the sternum 20 and implant 42 move toward the external magnet 48, the force generated between the magnets increases. If this force becomes too great and becomes uncomfortable for the patient, the magnet may be retracted toward the chest plate 44, thereby returning the magnetic force to the optimum comfort level for the patient. This process may be repeated for a number of intermediary steps, until the sternum 20 is gradually repositioned and/or deformed toward the desired final position and orientation.

The platform 40 may also include a strain gauge 74, or other force measuring means, to accurately determine the force being generated by the magnets. Strain gauge 74 may be connected via lead wires 76 to various points on the magnet plate 50 so that the pressure on each quadrant of the magnet may be accurately assessed. Strain gauge 74 may also comprise an LCD display (not shown) so that the patient or physician may readily assess whether the external magnet 48 is properly oriented, and adjust the magnet if need be.

The platform 40 is held in place by the magnetic pull between the two magnets, and in addition may be secured in place with a loose elastic band (not shown) around the chest. The principal force holding the platform 40 in place is the magnetic field itself. The patient may adjust the platform 40 to comfort and thus ensure against pressure damage to soft tissue. The patient may be taught to how to manipulate the external magnet 48 up and down to adjust and balance the force pulling the sternum 20 outward.

To provide extra comfort to the patient, and prevent the any unwanted manipulation of the adjustment members, a cover, such as that shown in FIG. 16, may be provided to cover the chest plate while the platform is being worn.

A preferred embodiment of the invention incorporating a bridged platform 200 is illustrated in FIGS. 16 and 17. Platform 200 has a chest plate 202 having a support 204 with opening 206 at it center. Chest plate 202 and support 204 may be separate pieces fastened together as shown in FIG. 16, or one integrated piece (not shown). Load member 208 is positioned in the opening 206 of support 204, and is bridged by a plurality of thin beam force sensors 214.

Load member 208 has a plurality of adjustment members 210 that retain magnet plate 50 and magnet 48 via a hanging means 212. Adjustment member 210 comprises an in-line screw, such as a jack-screw, lead screw, ball screw, or the like, which is hollowed out to support hanging means 212. As shown in FIGS. 16 and 17, hanging means 212 comprises a ball chain, but may also comprise a cable, wire, or the like. Alternatively, adjustment members 210 may comprise extended screws (not shown) that terminate a ball joint in magnet plate 50.

Adjustment members 210 may be manipulated to lower or raise the magnet 48, or adjust the angle of the magnet, as described in the embodiment of FIGS. 14 and 15. By turning screw 210 clockwise, one quadrant of the external magnet 48 may be precisely lowered to change the angle of the external magnet 48 with respect to the patient's chest, thereby changing the direction of the force applied to the implant 42. By turning all the screws the same clockwise increment, the magnet is lowered to generate a larger attractive force on the implant. Correspondingly, counter-clockwise rotation raises the external magnet to lower the attractive force on the implant 42.

When the platform is placed against the patient's chest, the attractive force between the implant 42 and the external magnet generates a load on load member 208. This load is sensed at all four quadrants by the thin beam force sensors 214. Readings from the sensors 214 are received by a force measuring means, such as the strain gauge 74 illustrated in FIG. 15, to provide accurate data on the force applied at each quadrant of the external magnet. This enables the treating physician or patient to accurately assess corrective the force being applied to the sternum, and modify the force if not at the desired level.

FIG. 17 illustrates an alternative embodiment having a platform 220 wherein the adjustment member comprises a clasp 222 for incrementally adjusting the extended length of ball chain 212, which is attached to each corner of the external magnet cradle 224. By changing the position at which the clasp 222 engages the ball chain 212 (similar to adjusting a necklace of bracelet), the height at any one quadrant of the magnet 48 may be changed with respect to the patient's chest to vary the force or direction of the corrective magnetic field. Chest plate 202 and cradle 204 may also have a layer of padding 226 to provide further comfort for the patient.

Over time, the steady gradual force applied to the sternum stretches the ligaments connecting the sternum 20 to the ribs. The sternum 20 itself may also deform as a result of the magnetic forces. The result is a reoriented and/or repositioned sternum without the characteristic depression of the pectus excavatum deformity.

As the sternum 20 moves closer to the external magnet 48, the patient or physician will typically readjust the position of external magnet 48 farther up into the chest plate. This is easily accomplished by adjusting the length of the four ball chains that suspend the magnet cradle 224.

FIGS. 50-52 illustrates another preferred embodiment of internal magnet assembly 600 configured to be mounted such that the internal magnetic implant is located on the anterior surface of the sternum 20. As shown in FIGS. 50 and 51, a sealed magnet assembly 602 comprises a hermetically sealed casing 608 that holds a magnet 604 and magnet retention cup 606 inside housing cover 610. The housing cover 608 may be laser welded to the housing 608 for proper seal. The housing cover 608 also is configured to receive a threaded post 612 that is sized to pass through a hole 628 drilled in the sternum 20, as illustrated in FIG. 52.

Referring to FIG. 52, a lower fixation assembly 620 is configured to be positioned at the posterior surface 32 of sternum 20. The lower fixation assembly 620 has a plate 622 and female threaded post that is configured to receive male threaded post 612 from the sealed magnet assembly 602. Plate 622 comprises a plurality of fixation points 624 that fixedly engage the bone of posterior surface 32 of the sternum 20. When the threaded post 612 of the sealed magnet assembly 602 is threaded into the receiving post 626 of the plate assembly 620, a compressive force is generated between the lower surface of the magnet housing 608 and plate 622, driving fixation points 624 into the bone mass of the sternum. Thus, in this configuration, the internal magnet assembly 600 is rigidly attached to the sternum 600 so that it may evenly distribute the load generated from the attractive force generated between it and the externally mounted magnet.

A washer-shaped spacer 614 may optionally be used to be positioned between the magnet housing 608 and upper sternum surface 34. Spacer 614 has a through hole for post 612, and may be sized accordingly to affect a desired height of the magnet above the sternum 20. The spacer 614 may also be formed of a semi-compliant material that conforms to the non-planar and irregular upper surface 34 of the sternum 20.

One or more suture hoops 630 may also be fixed (e.g. laser welded or otherwise fastened) to the magnet housing cover 608.

FIG. 53 illustrates another preferred embodiment of an external magnet platform assembly 640 for treating pectus excavatum or like deformities. The assembly 640 comprises a platform or chest plate 644 configured to be worn over a patient's chest and sized according to the patient's anatomy. The chest plate 644 may be made from a plastic-injection mold corresponding to the individual's chest deformity. The chest plate 644 is generally triangular shaped, with an upper arm 648 positioned upward, and two lateral arms 650 and 652 that arch around a portion of the patient's chest.

The chest plate 644 upper surface 654 has a recess 646 configured to receive external magnet assembly 664, with a through hole 656 so that external magnet housing 664 may be hung from the chest plate 644 and over the patient's chest. The underside 678 of the chest plate 644 is arched to create a cavity that allows the chest to expand outward as a result of treatment. The recess 646 is has a depression 658 configured to house a sensor 662. The sensor sits in the depression 658 so that a portion of the sensor rests above the housing floor, and forms a three-point contact along with protrusions 660 when the external magnet assembly 642 is placed in the recess 646. Thus, any downward force generated on the magnet assembly 642 is registered on the sensor 662, and a history of the applied force may be logged by memory associated with the sensor 662.

FIG. 54 illustrates a perspective expanded view of the external magnet assembly 664. Assembly 664 comprises a plate 668 and female threaded receiving post 670. Plate 668, in addition to supporting the external magnet 676, may be configured to also function as a magnetic shielding. External magnet 676 is housed in magnet housing 674 that has a threaded portion 672 configured to be received by post 670. The housing 676 may be a series of housings having incrementally variable height H. The height H may be chosen by the patient or physician to vary the force applied on the patient's sternum (e.g. a longer magnet housing would place the external magnet 676 closer to the internal magnet implanted on the patient's sternum, resulting in a larger applied loading to the sternum). The magnet may also be variably positioned within each housing 676 for micro-adjustment of the applied force.

Referring back to FIG. 53, a data-logging or storage device 680 may be coupled to the sensor 662 and mounted to the chest plate 644. The data logger 680 may be configured to receive sensor data of periodic measurements and store the data for later download and access.

It is appreciated that portions of the above embodiments may be used interchangeably with other embodiments where applicable. For example, any of the internal magnet configurations may be interchangeably used with the external magnet platforms to apply force to the internal body member of interest.

2. Scoliosis

FIGS. 18A and 18B illustrate the curvature of a normal spine 300. The spine is relatively straight in the sagittal plane 302 and has a double curve in the coronal plane 304. As shown below, the thoracic section 308 of the spine is convex posteriorly and the lumbar section 306 of the spine is convex anteriorly. Normally there should be no lateral curvature of the spine about the saggital plane 302.

Figure 19B:
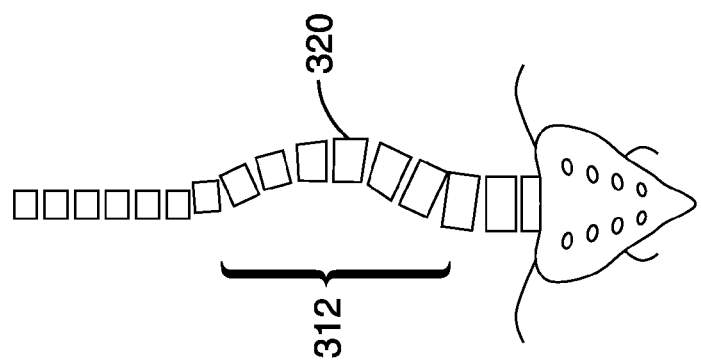
Figure 19A:
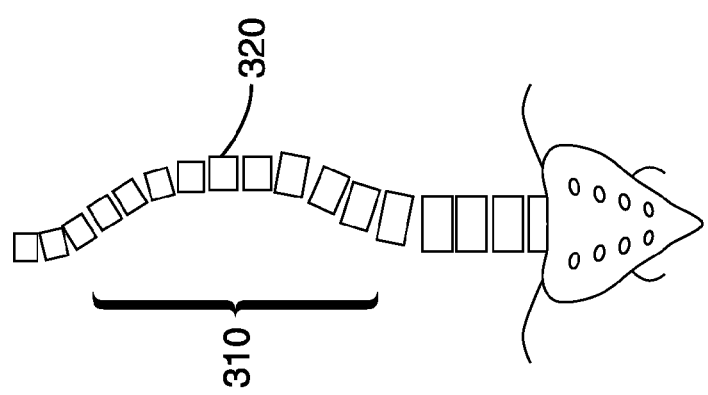
Figure 19D:
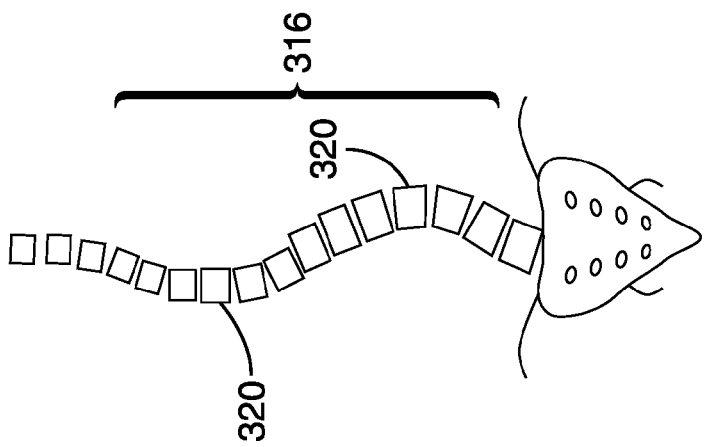
Figure 19C:
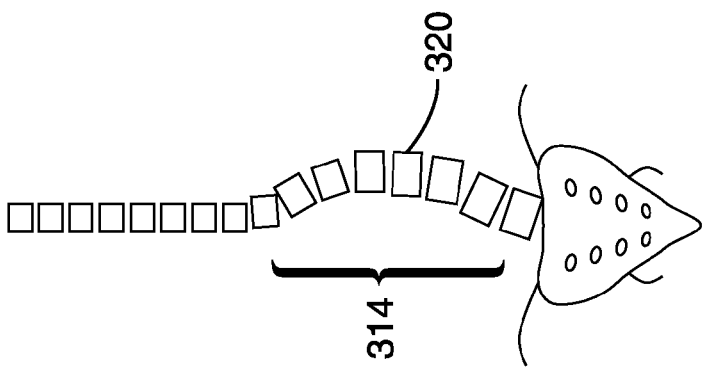

Scoliosis is a deformity that generally comprises by both lateral curvature and vertebral rotation. FIGS. 19A-D illustrate various forms of abnormal lateral curvature of the spine. FIG. 19A shows abnormal thoracic curvature 310. FIG. 19B shows abnormal thoracolumbar curvature 312. FIG. 19C shows abnormal lumbar curvature 314. Finally, some cases involve a double curvature of the spine, as shown in FIG. 19D shows abnormal thoracic curvature.

FIG. 20 illustrates rotation of the spine and corresponding effect on the rib cage 332 s a result of scoliosis. As the disease progresses, the vertebrae 330 and spinous processes in the area of the major curve rotate toward the concavity of the curve. As the vertebral bodies rotate, the spinous processes deviate more and more to the concave side and the ribs follow the rotation of the vertebrae. The posterior ribs on the convex side 336 are pushed posteriorly, causing narrowing of the thoracic cage and the characteristic rib hump seen in thoracic scoliosis. The anterior ribs on the concave side 334 are pushed laterally and anteriorly.

Now referring to FIG. 21, a schematic view of external platform 350 is illustrated with implant 340 installed on vertebrae 330 of the spine. Vertebrae 330 is preferably located at the apex 320 of the abnormal curvature shown in FIGS. 19A-D. In a preferred embodiment implant 340 is anchored to vertebrae 330 via a bone screw 336. Screw 336 may be threaded into a bore 334 in the pedicle 332 of the vertebrae according to commonly used procedures for a variety of spinal conditions, including degenerative disc disease and scoliosis. Examples of such systems are disclosed in U.S. Pat. Nos. 6,648,915; 6,010,503; 5,946,760; 5,863,293; 4,653,481, etc., the entire disclosures of which are incorporated herein by reference.

Once pedicle screw 336 is installed, internal magnet 342 may be fastened to screw 336 via magnet casing 338 and nut 346. Following the same procedure, a second internal magnet 344 may also be installed on the pedicle on the opposite side of implant 340.

After installation of implant 340, external platform 350 may be placed on the patient's back 366 adjacent to the installed implant. Platform may be retained to the torso of the patient by a strap the circles the patient's waist or chest at the elevation of the implanted vertebrae 330. Platform 350 comprises a support 352 that adjustably holds first external magnet 360. First external magnet 360 is hung inside recess 364 by a plurality rods 354, which are fastened to external mounting plate 358 housing magnet 360. The angle and height of magnet 360 may be incrementally adjusted by adjustment member 356.

As illustrated in FIG. 21, external magnet 360 and internal magnet 342 may be positioned with facing positive poles (or facing negative poles) to generate a repulsive force between the platform 350 and the implant 340. The resulting magnetic force creates a rotational moment R on the vertebrae 330 to incrementally reorient the vertebrae 330 and diminish the abnormal rotation angle β. As vertebrae 330 rotates to a more normal orientation, the rest of the vertebrae of the spine follow.

If a second internal magnet 344 is installed opposite internal magnet 342, a second external magnet 362 may be positioned opposite internal magnet 344. As shown in FIG. 1, the opposing magnets may be positioned to generate an attractive force, thereby increasing the magnitude of the rotational moment R on the vertebrae.

In addition to effecting rotation of the spine, platform 350 may be oriented to correct for lateral curvature of the spine. By placing the platform 350 to the line up to the left of the implants, as shown in FIG. 21, a translational force T is created on the vertebrae 330 as a result of the attractive force between the second external magnet 362 and second internal magnet 344. In this configuration, external magnet 360 may be removed to increase the attractive force. The platform 350 may be incrementally repositioned to continue translation of the vertebrae 330.

3. Other Applications

Variations of the above embodiments could be use to gradually correct a variety of deformities. For example, pectus carinatum (a deformity of the chest involving a sternal protrusion) may be treated with the embodiments shown in FIGS. 14-17 and orienting the magnets to apply a repulsive rather than attractive force.

In another alternative embodiment, which may be beneficial for soft tissue deformities, a magnetic force discontinuously applied in order to accommodate blood flow to the tissue. For example, the force may be applied for a period of time (e.g. a minute) and then taken off for another period of time (applied in a pulsed fashion) in order to let blood flow back to the tissue being "reformed". In one embodiment illustrated in FIG. 22, a pulsed force field is generated by rotation of the external magnet 402 with respect to fixed internal magnet 402. The magnets may have magnetized quadrants 404 that repel/attract or become neutral upon a 90 degree rotation with respect to each other to achieve tension alternating with relaxation. In an alternative embodiment, the external magnet is moved closer and then farther from the internal magnet by rotating it on a cam (not shown).

In addition to magnetic force fields configured to manipulate body members by attraction of two magnets (e.g. the device above for repair of pectus excavatum), the magnets may be configured to provide a repulsive force (e.g. a magnetic Elizeroff to lengthen bone). In the embodiment illustrated in FIG. 23, internal repulsion device 410 comprises first member 414 partially encased in second member 412, wherein first member 414 is allowed to slide inside second member 412. Each member has a corresponding internal magnet 416, 418 which are configured to repel each other, thus forcing first member 414 to separate from second member 412 to form a "magnetic spring" to distance anatomy located on ends 420 and 422. The repulsive force may be varied by adjusting the position of magnets 418 and 416 away from ends 420 and 422.

Repulsion device 410 may be used in a variety of applications where gradual force may be applied to reposition or deform one or more body members. For example, device 410 may be disposed such that ends 420 and 422 are attached to two separate locations of a bone to lengthen or alter the shape of the bone.

In an alternative embodiment illustrated in FIG. 24, repulsion device 430 may be used having reservoir 434 and pump 436. Pump 436 may be positioned underneath the patient's skin 438, such that fluid may be directed through lead line 440 to reservoir 434 in second chamber 432. The pump may be used to increase the volume of reservoir 434, thereby distancing magnet 416 away from end 420 to incrementally increase the repulsive force between 416 and 418.

In another alternative embodiment illustrated in FIG. 25, repulsion device 450 comprises a mechanical jackscrew 470. The device has a first member 452 and second member 454 that apply a repulsive force to attachment points 456 and 458 that may be attached to one or more body members. Rotary magnet coupling 468 has an internal magnet 474 under the patient's skin 476 and a corresponding external magnet 472.

The magnets are polarized such that rotation of the external magnet 472 causes a proportional rotation in external magnet 474, which in turn rotates flexible shaft 478. Rotation of flexible shaft 478 is transferred to rotation of screw 462 located on first member 452 via worm gear 460. Nut 466 is attached to second member 454 and is threaded to screw 462 such that rotation of screw 462 causes the first member 452 to separate from 454. Additional force and separation may be achieved by further rotation of external magnet 474. Springs 464 may optionally be employed to create an additional preload between the first and second members.

FIG. 26 illustrates another alternative embodiment of a repulsion device 500 having an electric jackscrew. Control box 504 controls rotation of magnetic coupling 502. A signal is sent via wire 510 to electronics 512 to control electric motor 514, which drives rotation of screw 518 through gear reduction 516. Thus, a repulsive force may be incrementally applied to separate first member 524 from second member 522.

FIG. 49 illustrates yet another embodiment of a repulsion system 540. The system 540 includes a magnetically coupled implantable jackscrew assembly 550 that is magnetically driven by an external drive assembly 560. The jackscrew assembly 550 comprises a first member 542 and second member 544 housed within a hermetically sealed bellows 556. The first and second members 542, 544 are coupled to allow linear motion with respect to each other to apply a repulsive force to respective attachment points 552 and 554 that may be attached to one or more body members or body member locations. For example attachment point 552 may be coupled to a first vertebral body, and attachment point 554 may be coupled to a second vertebral body to allow incremental distraction of the spine segments.

The first member 542 is coupled to an internal drive coupling or rotor 562 that is radially magnetized (may also be axially magnetized in an alternative embodiment) into semi-cylindrical halves 564 and 566. The internal rotor 662 is coupled to drive shaft 558 inside end cap 568.

The external drive assembly 560 has an external drive magnet or rotor 572, also being radially magnetized into semi-cylindrical halves 574 and 576. The external rotor 772 is coupled to a high speed rotational unit 578 (e.g. hand drill or the like) that is capable of rotating magnet 572 at high rpm. The internal and external rotors are polarized such that, when the external drive assembly 560 is positioned with the external rotor 572 at an external location above the patient's skin from the internal rotor 562, rotation of the external rotor 572 causes a proportional rotation in internal rotor 562, which in turn rotates shaft 558. Shaft 558 is coupled to gear reduction unit 580 that facilitates a high ratio gear reduction (e.g. 256:1 or 500:1) to worm gear screw 546. Gear reduction unit 580 allows high speed micro-motion control of the jackscrew assembly 550 via a small input or rotational force from the external rotor 752. The gear reduction unit 580 may comprise a commercially available unit such as Spur Gearhead GS12A or Micro Harmonic Drive MHD 8, both from Maxon Precision Motors, Inc., Fall River, Mass.

Female screw thread or nut 548 is attached to second member 544 and is threaded to screw 546 such that rotation of screw 546 causes the first member 542 to separate or converge with respect to second member from 544. Additional force and separation may be achieved by further rotation of external magnet 572.

The second member 544 may optionally be spring loaded with biasing member 584 to create an additional preload between the first and second members. Biasing member 584 may provide a shock absorption component to the assembly for withstanding loading between first and second body members disposed on attachment points 552 and 554. Initial loading to separate attachment points 554 and 552 may soak up some or all of the travel of biasing member 584, depending on the spring rate. However, as the body members associated with attachments points 554 and 552 are gradually manipulated, the travel of biasing member 584 is restored.

FIG. 49 depicts a linear coil-spring design for biasing member 584, however it is contemplated that an elastomer or magnetic repulsion spring (as shown in FIG. 23) may also be used.

The jackscrew assembly 550 may also comprise a force measurement transducer 582 that measures the force applied to the attachment points 552, 554. Transducer 582 is configured to take readings of the applied force over time, and may be configured to store them locally on a memory chip or the like, or transmit force data to an external receiving unit via a wireless remote transmission such as RFID, IR or the like. Transducer 582 may also comprise deformable silicon pressure sensing device, such as the Micro Electro Mechanical Systems (MEMS) implant currently be developed by OrthoMEMS, Inc. for orthopedic sensing.

4. Fistula and Auto-Anastomosis

In many situations, it is desirable to have two segments of hollow viscera to be brought in continuity by creating a fistula between them. Strategic placement of magnets in accordance with the present invention may be used to create an auto-anastomosis, essentially a fistula, in a minimally invasive way.

The method of the present invention for performing an auto-anastomosis or a fistula would be to have one magnet in each of the two hollow viscera and let them collapse. Because the strength of attraction between the two magnets increases the closer they are together, the magnets can apply enough force over time to cause necrosis of the tissue between. If the timing is correct, the tissue just outside the crushed tissue will essentially heal together, creating a fistula. The magnet pair would then fall out into the lumen and could be retrieved or passed.

Referring to FIG. 27, a method and system 800 for performing a side-to-side anastomosis in two hollow viscera is described. According the method of the present invention, a first magnetic implant 802 is positioned in a first organ segment 806 at a region or location where anastomosis and fistula is desired.

Delivery of the magnet to the desired location in the body may be facilitated through open surgery or through a number of minimally invasive approaches. For example, standard techniques such as laparoscopy, thorascopy, fetoscopy and the like may be employed, depending on the desired location and/or procedure. In some procedures, delivery may be achieved without open surgery, e.g. via gastrointestinal or urinary tract endoscopy.

FIG. 27 illustrates delivery to a location in organ segment 806 by use of a catheter 830. Catheter 830 may have a variety of configurations currently available in the art for delivery of an implant or other device through a lumen. For example, catheter 830 may have a catheter tube 834 housing remotely retractable grippers 832. The grippers 832 may hold the magnet 802 inside retractable sheath 836 while the catheter 830 is delivered to the desired location in the lumen. The sheath 836 may then be retracted to allow the magnet 802 to be released at the location.

After placement of the first magnet, second magnetic implant 804 is delivered to a second organ section 808 in proximity to first section 806. It is appreciated that organ segments 806/808 may be separate locations in the same organ, such as two sections of bowel that are separated by an obstruction or atresia, or separate but adjacent organs, such as between a ureter and bladder, or arterial-venous fistula.

As shown in FIG. 27, implants 802 and 804 are generally ring-shaped having a centrally located aperture 810. Alternatively, implants 812 and 814, shown in FIG. 28, may be used that are disc shaped. Implants 812 and 814 may be used in situations where an obstruction can be temporarily tolerated until the fistula is created (explained in more detail below). The implants are generally comprised of a magnetically charged material. A coating or hermetically sealed casing, such as titanium or epoxy, may encapsulate the implants to ensure biocompatibility. The outside diameter $d_o$ of the implant may vary according to the size of the desired fistula. Accordingly, the inside diameter $d_i$ may vary depending on the size of the temporary passage (described in further detail below). It is also appreciated that the implant may be configured to have one of a number of shapes depending on the application, e.g. the outer and inner edges may be elliptical, or other shape to accommodate the desired fistula.

Referring now to FIG. 29, the implants 802, 804 are placed with opposite poles facing each other at the desired location for the fistula. This creates an attractive force between the magnets 802 and 804, and the interior walls 816 and 818 between the magnets. The attractive force also acts to concentrically align magnets 802 and 804 along the same axis.

As illustrated in FIG. 30, the attractive force of the magnets 802 and 804 draws the inner walls 816 and 818 together until they contact each other. A compressive force is generated on the tissue 820 of walls 816 and 818 between the magnets. This compressive force gradually increases as the magnets get closer to each other Referring now to FIG. 31 In situations where a temporary passage for the contents of the viscera is desired or required (e.g. an obstruction downstream from the implant location) a cutout 822 may be performed in the tissue 820 of walls 816 and 818. The cutout may be circular to generally match the shape of hole 810 of the magnets. As shown in FIG. 31, cutout 822 and holes 810 in the magnets allow flow F of the contents of the viscera to be immediately restored to essentially bypass any downstream obstruction. Cutout 822 may be made non-invasively via a cutting tool (not shown) disposed at the location via and catheter 830 (shown in FIG. 27).

Alternatively, disc-shaped magnets 812 and 814 may be used where obstruction (or other condition) of the viscera is tolerable for the period it takes to achieve auto-anastomosis. In this case, no cutout is made in walls 820.

In either case, the compressive force placed on the tissue 820 trapped between the magnets causes necrosis of the tissue 820. As shown in FIG. 32, the tissue eventually falls out over a period of time (usually within days), and the walls 816 and 818 heal, or fuse together to form a fistula 826 around the perimeter of the magnets 802/804.

Finally in FIG. 33, the magnets 802/804 and necrosed tissue between them (if any), fall out from the fistula 826 and may either be retrieved, or simply pass out of the patient's system through the newly anastomosed lumen.

The above described method and system for auto-anastomosis may be performed on any hollow viscera, lumen, organ, etc. in the body where anastomosis and/or fistula are conventionally performed. For example the system 800 may be used for side-to-side anastomosis in the vascular system, e.g. an arterial-venous fistula for vascular access.

However, the methods and system 800 are ideally suited in regions of the body that are more susceptible to necrosis under high pressure, such as the gastrointestinal and urinary tracts.

Referring to FIG. 34 of the gastrointestinal tract, the system 800 may be used to achieve anastomosis in the esophagus 840, down to the stomach 842, small intestine 846 and colon 848. For example, the anastomosis may be performed in bariatric procedures such as gastric bypass.

In addition, system 800 may be used for palliative procedures for bowel stenosis or obstruction, i.e. intestinal atresia. Intestinal atresia may occur in a number of places in the gastrointestinal tract, e.g. the duodenum 844, jejunum 850 and ileum 852 of the small intestine 846, and colon 848. An anastomosis/fistula may be readily performed in this regions given the characteristics of the bowel, and the ease of placing segments of these organs adjacent to each other to bypass an obstruction. In certain types of jejunoileal atresia, where significant portions of the small intestine are missing, the present invention may be configured to stretch the separated intestinal lumens prior to anastomosis, similar to the system disclosed in co-pending U.S. application Ser. No. 11/222,517, incorporated herein by reference in its entirety.

FIG. 35 illustrates a schematic diagram of a patient having duodenal atresia. The duodenum 844 has a blockage 858 separating an upper portion 854 from a lower portion 856 of the duodenum.

Referring now to FIG. 36, magnetic implants 802 and 804 are delivered separately to each side of the blockage or atresia 858. This may be achieved via separate catheters, similar to catheter assembly 830, into the adjacent regions. For example, magnet 802 may be delivered via a catheter through the mouth and esophagus, or via laparoscopy. Magnet 804 may also be delivered via laparoscopy, or via endoscope. The magnets are positioned, and the segments 854 and/or 856 are maneuvered so that the magnets align adjacent to each other across the tissue of each segment. The auto-anastomosis process, as depicted in FIGS. 30-33, occurs over a period of time until a fistula is achieved and the magnets dislodge to be retrieved or pass out of the system.

Referring now to FIG. 37, system 800 may also be implemented to perform an anastomosis/fistula in the organs of the urinary tract, including urethra 866, bladder 864, and ureters 860. For example, implants 802 and 804 may be delivered to appropriate locations to create a fistula between a ureter and the bladder, or in the renal pelvis 870.

Referring now to FIGS. 38-39, system 880 may be implemented to create an ostomy. As shown in FIG. 38, a magnetic implant 882 may be delivered to a desired location in the organ 886 to be treated, e.g. the colon for a colostomy, small intestine for an illeostomy, or ureter for a urostomy. The implant 882 may be delivered via catheter 830 either by endoscope or laparoscope. An external magnet 884 is then placed over the patient's skin 888 adjacent the internal magnet 882, with opposite polarities facing each other so that an attractive force is generated between the magnets.

The attractive force between magnets 882 and 884 generates a compressive force on the tissue in between them, e.g. visceral wall 894, abdominal wall 890, and skin 888. This compressive force causes the tissues to necrose, and eventually anastomose until the magnets and tissue fall out, creating a fistula and stoma 892 through the visceral wall, abdominal wall and skin, as illustrated in FIG. 39. A plastic pouch, e.g. colostomy bag, is then attached to the skin 888 around stoma 892.

As shown in FIG. 40, the system may also include one or more intermediate internal magnets 896 to better facilitate necrosis of the abdominal wall 890. For example, the first implant 882 may be inserted into the desired organ 886, and a second implant 896 may be implanted in the abdominal wall between the skin 888 and visceral wall 8894. The polarities of magnets 882, 894 and 884 are aligned so that all three magnets attract toward each other. This has the effect of shortening the distance between magnets, thereby increasing the compressive force between them to facilitate necrosis and auto-anastomosis. Two or more intermediate internal magnets may also be used where necessary.

All magnetic members or implants heretofore disclosed may have magnetic, ferromagnetic, or electromagnetic properties and may include one or more materials, e.g. magnetic or non-magnetic.

Referring now to FIG. 41, magnetic implants 900 and 902 incorporating curvilinear surfaces may be positioned at two sections of a lumen or two adjacent lumens. These implants may be used to generate a variable force across a section of tissue, as described in further detail below. Implants 900 and 902 may be solid, or have a central lumen 910 to be used in situations where an obstruction can be temporarily tolerated until the fistula is created.

The implants 900, 902 are placed with opposite poles facing each other at the desired location in lumen sections 806, 808 for generating the fistula.

This creates an attractive force between the magnets 900 and 902, and the interior walls 816 and 818 between the magnets. The attractive force also acts to concentrically align magnets 900 and 902 along the same axis 912.

As illustrated in FIG. 42, the attractive force of the magnets 900 and 902 draws the inner walls 816 and 818 together until they contact each other. A compressive force is generated on the tissue 820 of walls 816 and 818 between the magnets. This compressive force gradually increases as the magnets get closer to each other.

As shown in FIG. 41, the first magnet 900 comprises a concave or cupped surface 904 having a radius $r_c$, while the second magnet 902 of opposite polarity, comprises a convex or spherical surface 906 having a radius $r_s$. In a preferred embodiment, the cupped surface 904 has a larger radius $r_c$ than the radius $r_s$, of the convex surface 906 of magnet 902, i.e. $r_c > r_s$.

The differing radii of magnets 900 and 902 results in a non-uniform force distribution P across the surfaces of the magnets. As illustrated in FIG. 43 (showing only magnet 900 for clarity), the force distribution P across the magnet surface 904 is highest along the central axis 912, where the magnets are at their closest. Moving radially outward toward the perimeter of the magnet, the force becomes increasingly smaller, until reaching the smallest force at the perimeter 908, where the magnets 900 and 902 are furthest from each other.

The non-uniform stress distribution as shown in FIGS. 41-43 is advantageous for auto-anastomosis of tissue. The larger force along central axis 912 can be configured to be strong enough to generate necrosis of tissue 820 in that region. Correspondingly, the smaller force at the perimeter will be just large enough to fuse the tissue 820 on the periphery, while still promoting growth. Thus, the tissue in the center is necrosed to generate the aperture, while the tissue in the periphery is still live, facilitating a robust fusion between walls 816 and 818.

Referring now to FIG. 44 the necrosed tissue at the center of the compressed tissue 820 falls out, forming a temporary passage 822 for the contents of the viscera to flow from lumen section 806 through of hole 910 of the magnets, to lumen 808. As described above with respect to FIG. 31, a cutout may be performed where the contents of the viscera are to be immediately restored to essentially bypass any downstream obstruction.

As shown in FIG. 45, more of the centrally-located tissue eventually falls out over a period of time (usually within days), allowing the magnets 900, and 902 to pass the fistula and pass out the body or be retrieved. The walls 816 and 818 heal and fuse together at 820 a fistula 826.

The magnets 900 and 902 are shown in FIGS. 41-45 above as having one curvilinear surface each. However, as shown in FIG. 46, magnet 918 may have two concave surfaces 922, and magnet 920 may have a generally spherical outer surface 924 to form a sphere. In this configuration, the opposing-charged magnets will be assured to line up properly to the correct surface.

FIG. 47 illustrates an exploded view of a convex magnet assembly 930 and concave magnet assembly 940. The convex magnet assembly comprises a ring magnet 938 that is configured to be inserted into recess 936 in casing 932. The casing 932 comprises a convex or spherical surface 934 that may be a non-magnetic material, such as Teflon, or other polymer. Concave magnet assembly 940 comprises a corresponding ring magnet 948 of opposite polarity, which is configured to be inserted into recess 946 of casing 942. The casing has a cupped or concave surface 944 that preferably has a larger radius than spherical surface 934.

FIG. 48 illustrates magnet assemblies 930 and 940 installed in opposing lumen sections. The attractive force of magnets 938 and 948 compress the tissue of walls 816 and 818 disposed between the magnet casings 932, 942. Although the magnets generate a constant force across their circumference, the varying radii of cupped surface 944 and spherical surface 934 compress the tissue of walls 816 and 818 non-uniformly across the circumference of the assemblies. As shown in FIG. 48, the tissue at the central axis 912 is more compressed than at the periphery 908. Thus, the tissue in the center is necrosed to generate the aperture, while the tissue in the periphery is still live, facilitating a robust fusion between walls 816 and 818.

The above described method and system for auto-anastomosis may be performed on any hollow viscera, lumen, organ, etc. in the body where anastomosis and/or fistula are conventionally performed. For example the system 800 may be used for side-to-side anastomosis in the vascular system, e.g. an arterial-venous fistula for vascular access, or gastrointestinal and urinary tracts.

FIGS. 55-65 illustrate an auto-anastomosis system utilizing a 3-piece design with cutting mechanism. The 3-piece system may be implemented to perform an anastomosis within two adjacent lumens in the body.

FIGS. 55-58B show a first embodiment of the 3-piece auto-anastomosis system 700 of the present invention. The system 700 comprises a first magnetic member 702, a second magnetic member 704, and cylindrical cutting member 706 slideably coupled to first magnet 702. As shown in the perspective view of FIG. 55 and top view of FIG. 56, the magnets 702, 704 and cutter 706 have a substantially elliptical or oblong shape with a length L generally greater than the width W.

The elliptical, oval or oblong shape of the above elements allows the magnets 702,704 to be inserted and delivered along a portion of a lumen with a minimum profile to aid delivery of the magnets to the target anastomosis site. Once the magnets 702,704 are properly located, they may then be oriented so that their polarities generate an attractive force between them as desired to perform the anastomosis.

FIGS. 57A and 57B illustrate a cross-sectional view of the system 700 along the long axis or length of the magnets 702, 704 and cutting member 706, while FIGS. 58A and 58B illustrate a cross-sectional view of the system 700 along the short axis or width of the magnets illustrates. The magnets preferably have a spherical interface such that the first magnet 702 has a convex lower surface 718 the second magnet 704 has a concave or cupped upper surface 716, wherein the interface surfaces 716 and 718 have a radius corresponding to one another.

The first magnet 702 comprises a housing 720 with a recess sized to receive a ring magnet 712 and a cap 722 that encapsulates the ring magnet 712 in the housing 720. Correspondingly, second magnet 704 also comprises a housing with a recess sized to receive a ring magnet 714 and a cap that encapsulates the ring magnet 714 in the housing. The casing or housing 720 for each magnet 702, 704 preferably comprises a non-magnetic material, such as Teflon, or other polymer. Ring magnet 714 generally has a polarity opposite the ring magnet 712 so that an attractive force is generated when the magnets are positioned as shown in FIGS. 55-58B.

Each of the magnets 702 and 704 has a through-hole 724 that is centrally located and having an axis that is substantially concentric when the magnets 702 and 704 are positioned for anastomosis. The through hole 724 for the upper magnet has in inner diameter Di that is sized to be equal to or slightly larger than the outer diameter Dc of the tubular cutting blade 708 of cutting member 706. Thus, the cutting member 706 has a slidable engagement with the first magnet 702 axially down the thru-hole 724. The inner diameter Di of hole 724 of the second magnet 704 may be larger than the hole 724 of the first magnet 702 so that the cutting blade 708 is allowed into the hole 724 of the second magnet 704 even when not aligned exactly coincident with first magnet 702.

Cutting member 706 comprises a tab 710 disposed at the upper end of the cutting blade 708. The tab serves to stop motion of the cutter at the top end of the first magnet 702, and also to retain the cutting member 706 and blade 708 within the through-hole 724. As seen in FIGS. 58A and 58B, the tab 706 comprises a set of downward extending arms 728 that engage the side walls of the magnet 702. The housing 720 has a slot 730 that allows the arms 728 to slide downward (FIG. 58B) while the blade 708 moves downward for cutting. The arms 728 are configured to hold the cutting element 706 in the upper position shown in FIGS. 57A and 58A, wherein the cutting blade 708 is kept enclosed within hole 724 so that no tissue is cut during delivery of magnet 702.

FIGS. 59A and 59B illustrate the system 700 installed within the body of a patient to perform an auto-anastomosis procedure. Referring to FIG. 59A, the first magnet 712 is delivered to a location within lumen wall 701 with the convex surface 718 adjacent the lumen wall 701. The second magnet 702 is positioned in an adjacent lumen with cup surface 716 facing wall 703 and lined up to be concentric with magnet 702.

The cutting member 706 is then manually engaged to slide along the axis of through-hole 24 from the first upper position in FIG. 59A to the second lower position in FIG. 59B. The blade 708 of the cutting member 706 slices through tissue 701 and 703. A circular cutout is generated with tissue 705 passing out of the area, thus forming a passageway between hole 726 in cutter between lumen 701 and 703.

FIGS. 60-63 illustrate a second embodiment of a 3-piece auto-anastomosis system 750 in accordance with the present invention. The system 750 comprises a first magnetic member 732, a second magnetic member 734, and cylindrical cutting member 736 slideably coupled to first magnetic member 732. As shown in FIGS. 62 and 63, the magnetic members 732, 734 and cutter 736 have a substantially circular shape. However, an elliptical shape similar to the system 700 of FIGS. 55-58B may also be used.

Referring to FIGS. 61A and 61B, the magnetic members 732, 734 comprise opposite polarity magnets 744, 746 that are encapsulated or housed in a biocompatible casing.

Cutting member 736 comprises a tubular blade 740 coupled to U-shaped cap 742 with a plurality of slots 738 that allow the cap to be snugly positioned on the first magnetic member 732. The cap 72 secures in one of a plurality of grooves 756 (see FIG. 62) on the side of the first magnetic member 732.

When retained in the upper groove, the cap 736 secures the cutting member 736 in a pre-cut, stowed orientation that shields the blade 740 from cutting tissue during transport, as shown in FIG. 61A.

When the magnetic members 732, 734 are positioned at the treatment site(region), the blade 740 may be reciprocated downward into central bore 754 of the first magnetic member 732 to the cutting orientation shown in FIG. 61B.

As illustrated in FIGS. 62 and 63, the magnetic members 732 and 734 may have mating surfaces that comprise elliptical cup 758 and cone 725. This configuration forms an elliptical anastomosis at the treatment site.

FIGS. 64 and 65 illustrate another embodiment of 3-piece auto-anastomosis system 760 of the present invention. The system 760 comprises a first magnetic member 762, a second magnetic member 764, and elliptical cutting member 766 slideably coupled to first magnetic member 762. The magnetic members 762, 764 and cutter 766 have a substantially elliptical or oblong shape that is rounded to allow for easy transport down a body lumen.

The elliptical shape of the above elements allows the magnetic members 762, 764 to be inserted and delivered along a portion of a lumen with a minimum profile to aid delivery of the magnets to the target anastomosis site. Once the magnetic members 762, 764 are properly located, they may then be oriented so that their polarities generate an attractive force between them as desired to perform the anastomosis.

The magnetic members 762, 764 each comprise an elliptical bore that closely matches the outer surface of cutting blade 774. The bore 768 on the second magnetic member 764 may be widened to allow for misalignment of the magnetic members prior to and during cutting of the tissue. The blade 772 may also have a groove 744 that interfaces with internal notches (not shown) in magnetic member 762 to hold the blade 772 in pre-cut and post-cut orientations.

As illustrated in FIGS. 64 and 65, the magnetic members 762 and 764 have mating surfaces comprising a convex surface 770 and concave surface 778 that serve to align the magnets and promote the desired compression of tissue.

FIGS. 66A-C illustrate three separate embodiments of the mating surfaces of the magnetic members that vary the compressive force distributed across the tissue. As shown in FIG. 66A-C, the lower magnet 782 has a curvilinear surface that is substantially spherical, and with a constant radius.

In FIG. 66A, upper magnetic member 780 has a planar interfacing surface 788. This creates a non-uniform compressive force distribution across the tissue, with the load increasing radially inward toward the through hole in the magnets.

In FIG. 66b, upper magnetic member 784 has a curvilinear interfacing surface 790, yet with a larger radius than the radius of the lower magnetic member 782. This also creates a non-uniform compressive force distribution across the tissue, with the load increasing radially inward toward the through-hole in the magnets. However, the gradient in pressure from perimeter to through-hole in this variation will be less than that in FIG. 66A. In other words, FIGS. 55-65 and 66b show a system for auto-anastomosing a region of the body with a first implant comprising a body, a first magnet with a first magnetic polarity, a first through-hole, and a terminal annulus defining a convex mating surface, and wherein said convex mating surface has a first radius and a second implant comprising a body, a second magnet with a second magnetic polarity opposite from said first magnetic polarity, a second through-hole, and a terminal annulus defining a concave mating surface, wherein said concave mating surface extends within the body of said second implant, and wherein said concave mating surface has a second radius, wherein said second radius is greater than said first radius, wherein while said convex mating surface faces said concave mating surface, a magnetic mating of said surfaces causes the terminal annulus of the first implant to extend within the body of the second implant and apply a non-uniform compressive force across two adjacent structures disposed in between said two mating surfaces, wherein said non-uniform compressive force is capable of forming an anastomosis between said two adjacent structures.

In FIG. 66c, upper magnetic member 780 has a curvilinear interfacing surface 792 that matches the radius of the lower magnetic member 782. This creates a uniform compressive force distribution across the tissue, with the load being constant from perimeter to through-hole.

It is appreciated that any of the variations shown in FIG. 66A-B may be used interchangeably with the magnet assemblies shown in FIGS. 55-65 or FIGS. 41-48. In addition, various aspects or feature of the different embodiments shown in FIGS. 55-65 may be used interchangeably with each other, where applicable.

Experiment #1 a. Test Setup

Two-component magnetic compression devices were manufactured from polytetrafluoroethylene stock. One component (magnetic member) was milled to a convex mucosal (active) surface with a one inch radius of curvature. A doughnut-shaped, axially magnetized neodymium-iron-boron magnet was affixed to the anti-mucosal surface. The complementary component was designed with varying concavity: radii of curvature either infinite (similar to the embodiment shown in FIG. 66A) or one inch (similar to the embodiment shown in FIG. 66A FIG. 66C). An identical toroid magnet was snapped on the anti-mucosal surface of this component as well. Separation distance between the two magnets without interposed tissue was 5 mm. The device pair with a flat component is referred to as the 'gradient' device due to its non-uniform, wedge-shaped profile at the compression rim (FIG. 66A). The other pair had matching surface curvature and is titled the 'uniform' device in reference to the constant separation of mating surfaces (FIG. 66C).

Devices were designed such that surface fields of approximately 3000 Gauss (G) were observed. Preliminary experimentation had revealed that combinations of 3000 G/6000 G and 6000 G/6000 G uniformly caused necrosis and perforation within 48 hours independent of device geometry.

Young adult pigs (Sus scrofa) were placed under general anesthesia and administered intravenous cefazolin. Laparotomy was performed with creation of a stapled side-to-side small intestinal anastomosis and placement of a pair of magnemosis devices in the bypassed limb of small intestine. In a subset of animals, a hand-sewn anastomosis was created in this limb as well. Hand-sewn anastomoses were performed in 2 layers: a full-thickness running suture of absorbable monofilament for the inner layer and an outer layer of interrupted seromuscular silk sutures. Mesenteric defects were closed to prevent internal herniation. The 'omega loop' of small bowel thus created was affixed to the anterior abdominal wall with two interrupted seromuscular pex sutures. The abdomen was irrigated with warm saline and the fascia closed with running monofilament suture.

Skin was reapproximated with staples and the animals were aroused from their anesthetic and extubated. Oral intake was limited to water overnight and an unrestricted diet resumed on the first postoperative morning. Animals were housed in a vivarium postoperatively, penned in pairs without any special care or needs.

At one, two, or three weeks postoperatively, animals were euthanized by central venous injection and underwent laparotomy. The abdomen was explored for evidence of peritonitis, abscess, or contained leak. Anastomoses were harvested and preserved in warm saline for testing within one hour. Native segments of small and large intestine were also harvested and preserved for testing. The anastomoses created by magnetic devices were grossly inspected to determine patency of the lumen. The device was disengaged from the anastomosis with care taken not to affect the anastomoses.

Each anastomosis was evaluated by suturing the ends closed around two noncompliant catheters. One of these catheters was connected to a syringe for instillation of radiographic contrast mixed with visual dye. The other was connected to a calibrated pressure-measuring circuit. Isovolumic mixture of visual dye and aqueous radiographic contrast was injected into the anastomotic lumen while monitoring pressure changes. Radiographs were obtained at 1 and 7 mmHg. Failure pressures of the anastomoses were measured by visualization of dye extravasation or drop in measured pressure—whichever occurred first. Dye was further injected until visible evidence of anastomotic failure and the maximum pressure was recorded.

After mechanical failure of each anastomosis, it was cut in sections and fixed in 10% formalin for subsequent mounting on slides and staining by hematoxylin and eosin. Descriptive statistics, analysis of variance (ANOVA), and student's t-test were employed to evaluate the data. All relevant p values are two-tailed, and heteroscedasticity was assumed.

b. Results

Sixteen pigs underwent successful operation. There were no episodes of intestinal obstruction or intolerance of food. No animal suffered peritonitis or frank anastomotic leak, though exploration of one stapled anastomosis at 2 weeks revealed a contained leak. Severe inflammation around 2 other stapled anastomoses led to injury during exploration so these were not suitable for radiographic or mechanical analysis. Two animals developed superficial incisional infections but there were no fascial dehiscences or deep abscesses. One animal died on postoperative day 2 due to upper gastrointestinal hemorrhage but necropsy revealed no association between this event and the enteric anastomoses. Thus, 32 total anastomoses remained for analysis (See Table 1).

Anastomoses from magnetic devices formed more rapidly with the gradient device (3/3 patent at 1 week, 3/3 patent at 2 weeks) than the uniform device (1/3 patent at 1 week, 2/2 patent at 2 weeks). Two anastomoses created by uniform compression devices still had the compressed central plug in situ at one week. Devices appeared to readily pass through completed anastomotic channels, and were found in the large intestine or in the animals' stool between 7 and 14 days. No device in transit caused evidence of obstruction, as gauged by feeding behavior, stooling frequency, and caliber of intestine proximal to the device. No animal had visible evidence of anorectal trauma, and veterinarians were unaware of discomfort experienced by the animals as a consequence of stooling out the device.

There was no significant difference between burst pressures of the anastomoses formed by the various techniques (p values from ANOVA were 0.28, 0.23, 0.61 for 1, 2, 3 weeks, respectively). Of note, several magnetic anastomoses did not achieve failure because a leak developed in unaffected intestine. In these cases, burst pressure of the intestine itself was recorded as the burst pressure of the anastomosis. This occurred for the gradient magnet anastomosis once each at one, two, and three weeks. It did not occur for the uniform magnet, handsuture, or staple anastomoses. This was interpreted as a trend toward superior strength of anastomoses formed by gradient compression.

Relative dilation of anastomoses when insufflated from 1 to 7 mmHg is listed in Table 2. Also listed is extent of relative stenoses in the magnetic anastomoses. The latter evaluation was not applicable to hand-sutured and stapled anastomoses since the uniformity of anastomosis size could not be guaranteed; anastomoses harvested at different time points (hence from different pigs) could not be compared.

FIG. 67 shows a cross-section of an anastomotic ring formed by magnetic gradient compression at one week. (A) is the new anastomotic channel, (B) are the original intestinal lumina, and (C) is the serosal surface. Histologic continuity of the intestinal wall is evident. (Hematoxylin & eosin, 5× magnification). Histologic evaluation of magnetic anastomoses revealed that along the newly formed tunnel connecting the two original limbs of intestine, there was continuity of serosal, submucosal, and mucosal layers without ischemia or necrosis. Uniform magnamoses with central plugs still attached demonstrated mild evidence of ischemia, but these pedunculated segments of tissue appeared somewhat viable. Gradient magnamoses lacked persistent viable tissue within the new lumen. General inflammation was greater in stapled and hand-sewn anastomoses than either magnetic anastomosis at all three time points.

c. Discussion

The tests demonstrate the feasibility and benefits of performing sutureless compression anastomoses using the magnetic implants of the present invention. Neither leaks nor appreciable stenosis were observed, even despite the centimeter-scale devices employed in these initial trials.

Between the two topologic designs, trends were observed toward superiority of the gradient compression device. This was indicated by the more rapid completion of the anastomoses with gradient compression and the persistence of viable pedunculated tissue plugs in some of the anastomoses created by uniform compression.

In general, to form an anastomosis by translumen compression, there should be sufficient compression to affect ischemia with central necrosis such that a new channel is formed rather than an ulcer or fistula. However, pressure must be controlled so that the surrounding non-compressed tissue has time to remodel and form a competent ring around the new anastomotic channel.

The tests showed the ability to control the ischemic process by adjusting the magnitude of compression and topology of the mated surfaces. Magnets with surface fields greater than 3000 Gauss uniformly led to perforation without anastomosis. The radial compression gradient exerted greatest effect toward the center, but left a rim of tissue under intermediate pressure which remodeled with histologic continuity.

The absence of embedded foreign bodies suggests unimpeded and more rapid remodeling/healing with less surrounding adhesive reaction. This was grossly observed during our operations, but not objectively measured. Furthermore, the absence of fiber or wire foreign bodies allows these anastomoses to expand dynamically with fluctuations of pressure, potentially decreasing the likelihood of anastomotic obstruction.

Some of the unique aspects of the magnemosis device of the present invention are the specifically designed topology and application of a calibrated field. Self-orientation of the magnetic members and independence of physical contact facilitate deployment from a distant site, and laparoscopic, endoscopic, and transluminal (natural orifice) approaches are all possible.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Table One. Characteristics of Animals and Anastomoses

|  | One Week | Two Weeks | Three Weeks | Total |
|---|---|---|---|---|
| Number of pigs | 6 | 5 | 4 | 15[a] |
| Initial pig size (kg)[b] | 40.5 (4.3) | 40.2 (1.5) | 42.2 (4.3) | — |
| Anastomosis maturity (days)[b] | 6.2 (0.4) | 12.6 (1.5) | 22.5 (0.6) | — |
| Deaths | — | — | — | 1[a] |
| Anastomoses Analyzed | | | | |
| Magnet - Gradient | 3 | 3 | 2 | 8 |
| Magnet - Uniform | 3 | 2 | 2 | 7 |
| Staple | 5 | 3 | 4 | 12[c] |
| Hand-suture | 3 | 0 | 2 | 5 |
| Total | 14 | 8 | 10 | 32 |

[a]One animal died on postoperative day 2 from an unrelated upper gastrointestinal hemorrhage.
[b]Mean (standard deviation).
[c]Of 15 stapled anastomoses, 3 were not analyzed (1 had leaked and 2 were damaged on exploration).

TABLE 2

Table Two. Dynamic Characteristics of Anastomoses

|  | Magnet-Gradient | Magnet-Uniform | Stapled | Hand-Sutured | p |
|---|---|---|---|---|---|
| Relative Dilation with Pressure[a] | 49% (32%) | 38% (17%) | 2% (8%) | −2% (8%) | 0.001[b] |
| Relative Stenosis[c] | 2% (11%) | −3% (13%) | N/A | N/A | 0.93[d] |

[a]Mean (standard deviation) increase in diameter (7 mmHg vs 1 mmHg).
[b]Magnetic anastomoses together vs stapled and hand-sutured anastomoses together.
[c]Mean (standard deviation) decrease in diameter (week 3 vs week 1).
[d]Gradient vs uniform magnetic anastomoses.

What is claimed is:

1. A system for auto-anastomosing a region of the body, comprising:

a. a first implant comprising: a body, a first magnet with a first magnetic polarity, a first through-hole, and a terminal annulus defining a convex mating surface, and wherein said convex mating surface has a first radius and b. a second implant comprising: a body, a second magnet with a second magnetic polarity opposite from said first magnetic polarity, a second through-hole, and a terminal annulus defining a concave mating surface, wherein said concave mating surface extends within the body of said second implant, and wherein said concave mating surface has a second radius, wherein said second radius is greater than said first radius, wherein while said convex mating surface faces said concave mating surface, a magnetic mating of said surfaces causes the terminal annulus of the first implant to extend within the body of the second implant and apply a non-uniform compressive force across two adjacent structures disposed in between said two mating surfaces, wherein said non-uniform compressive force is capable of forming an anastomosis between said two adjacent structures.

2. The system for auto-anastomosing a region of the body of claim 1, wherein said non-uniform compressive force across said two adjacent structures increases radially inward toward said first and second through-holes.

3. The system for auto-anastomosing a region of the body of claim 1, wherein said non-uniform compressive force is strong enough to generate a necrosis tissue region of said two adjacent structures.

4. The system for auto-anastomosing a region of the body of claim 3, wherein said necrosis tissue region departs from said two adjacent structures to form a flow passage.

5. The system for auto-anastomosing a region of the body of claim 4, wherein said flow passage forms a fistula, wherein said fistula passes said implants there through.

6. The system for auto-anastomosing a region of the body of claim 1, wherein said non-uniform compressive force comprises a force at the perimeter of said implants that is strong enough to fuse said two adjacent structures while still promoting tissue growth within said two fused structures.

7. The system for auto-anastomosing a region of the body of claim 1, wherein said convex mating surface is a single convex mating surface.

8. The system for auto-anastomosing a region of the body of claim 1, wherein said concave mating surface is a single concave mating surface.

* * * * *